(12) United States Patent
Addepalli et al.

(10) Patent No.: US 7,615,627 B2
(45) Date of Patent: Nov. 10, 2009

(54) RNA INTERFERENCE MEDIATED INHIBITION OF AURORAKINASE B AND ITS COMBINATIONS AS ANTICANCER THERAPY

(75) Inventors: Murali Krishna Addepalli, Maharashtra (IN); Vidyadhar Eswar Chandra Gopavaram Reddy, Maharashtra (IN)

(73) Assignee: Reliance Life Sciences PVT. Ltd., Maharashtra (IN)

( * ) Notice: Subject to any disclaimer, the term of this patent is extended or adjusted under 35 U.S.C. 154(b) by 0 days.

(21) Appl. No.: 11/812,513

(22) Filed: Jun. 19, 2007

(65) Prior Publication Data

US 2008/0038189 A1 Feb. 14, 2008

(30) Foreign Application Priority Data

Jun. 21, 2006 (IN) .................. 974/MUM/2006

(51) Int. Cl.
*C07H 21/04* (2006.01)
*C07H 21/02* (2006.01)
*A61K 48/00* (2006.01)

(52) U.S. Cl. .................. 536/24.5; 536/23.1; 536/24.3; 514/44

(58) Field of Classification Search ................. None
See application file for complete search history.

(56) References Cited

U.S. PATENT DOCUMENTS 5,734,039 A * 3/1998 Calabretta et al. .......... 536/24.5
2005/0267065 A1 12/2005 Dean et al.

FOREIGN PATENT DOCUMENTS

| JP | 2005-278472 A | 10/2005 | |
|---|---|---|---|
| JP | 2005-320351 A | 11/2005 | |
| WO | WO 02/090514 A2 | 11/2002 | |
| WO | WO 2004/070062 A2 * | 8/2004 | ................. 435/6 |

OTHER PUBLICATIONS

Scrittori et al., A Small C-Terminal Sequence of Aurora B Is Responsible for Localization and Function, 2005, Molecular Biology of the Cell, vol. 216, pp. 292-305.*
Kang et al., Suppression of EGFR expression by antisense or small interference RNA inhibits U251 glioma cell growth in vitro and in vivo, 2006, Cancer Gene Therapy, 13, pp. 530-538.*
Chieffi et al., Aurora B Expression Directly Correlates With Prostate Cancer Malignancy and Influence Prostate Cell Proliferation, 2006, The Prostate, 66, pp. 326-333.*
Marciniak et al., Epidermal growth factor receptor-related peptide inhibits growth of PC-3 prostate cancer cells, 2004, Molecular Cancer Therapeutics, 3(12), pp. 1615-1621.*
Tuschl et al., The siRNA user guide, Aug. 26, 2001 (on-line), retrieved Jan. 31, 2002, pp. 1, 3 and 5, Max Planck Institute for Biophysical Chemistry.*

Holen et al., Positional effects of short interfering RNAs targeting the human coagulation trigger Tissue Factor, 2002, Nucleic Acids Research, vol. 30, No. 8, pp. 1757-1766.*
Manoharan, Oligonucleotide Conjugates as Potential Antisense Drugs with Improved Uptake, Biodistribution, Targeted Delivery, and Mechanism of Action, 2002, Antisense & Nucleic Acid Drug Development, 12, pp. 103-128.*
Briassouli et al., "Aurora-A Regulation of Nuclear Factor-kB Signaling by Phosphorylation of IkBα" Cancer Res., Feb. 2007, 67(4), pp. 1689-1695.
Yang et al, "Aurora-A Kinase Regulates Telomerase Activity Through c-Myc in Human Ovarian and Breast Epithelial Cells", Cancer Res., 2004, 64, pp. 463-467.
Soncini et al. "PHA-680632, a Novel Aurora Kinase Inhibitor with Potent Antitumoral Activity", Clin. Cancer Res., 2006, 12(13), pp. 4080-4089.
Livak et al., "Analysis of Relative Gene Expression Data Using Real Time Quantitative PCR and the $2^{\Delta\Delta C_T}$ Method," Methods, 2001, 25, pp. 402-408.
Srikantan et al., "HEPSIN" Inhibits Cell Growth/Invasion in Prostate Cancer Cells, Cancer Res., 2002, 62, pp. 6812-6816.
Yarrow et al., "A high-Throughput Cell Migration Assay Using Scratch Wound Healing, A Comparison of Image-Based Readout Methods", BMC Biotechnology, 2004, 4(21), pp. 1-9.
Klein et al., "A New Quantitative Test Method for Cell Proliferation Based on Detection of the Ki-67 Protein", J Material. Sci: Materials in Med., 2000, 11, pp. 125-132.
Du Manoir et al., "Detection of complete and partial chromosome gains and losses by comparative genomic in situ hybridization", Human Genetics, 1993, 90, pp. 590-610.
Kim et al., "Synthetic dsRNA Dicer-substrates Enhance RNAi Potency and Efficacy", Nature Biotechnology, 2005, 23, pp. 222-226.
Weinstat-Saslow et al., "Angiogenesis and Colonization in the Tumor Metastatic Process: Basic and Applied Advances", FASEB Journal, 1994, 8, pp. 401-407.
Lee et al., "Targeting Aurora Kinases for the Treatment of Prostate Cancer", Cancer Res., May 2006, 66, pp. 4996-5002.
Chieffi et al., "Aurora B Expression Directly Correlates with Prostate Cancer Malignancy and Influence Prostate Cell Proliferation", Prostate, 2006, 66, pp. 326-333.
Rojanala et al., "The Mitotic Serine Kinase, Aurora-2, is a potential target for drug development in human pancreatic cancer", Mol. Cancer Ther., 2004, 66, pp. 451-457.

(Continued)

*Primary Examiner*—Amy Bowman
(74) *Attorney, Agent, or Firm*—Foley & Lardner LLP

(57) ABSTRACT

This invention relates to the use of short nucleic acid molecules that modulate Aurora-B kinase (AurkB) expression. The invention includes compounds, compositions and methods useful for the modulation of expression and activity of genes involved in the AurkB pathway. In one embodiment, the present invention provides short nucleic acid molecules, such as siRNA, which can be used in treating, preventing, or inhibiting cancer, and any other proliferative disease, trait or condition, which respond to a reduction in AurkB expression in a cell or tissue. Such short nucleic acid molecules can be used alone or in combination with other treatments or therapies, including short nucleic acid molecules that modulate expression of EGFR.

10 Claims, 27 Drawing Sheets

OTHER PUBLICATIONS

Kurai et al., "Expression of Aurora Kinases A and B in Normal, Hyperplastic, and Malignant Human Endometrium: Aurora B As a Predictor for Poor Prognosis in Endometrial Carcinoma", Human Pathol., 2005, 36, pp. 1281-1288.

Zhou et al. "Genetic Variation in Human NPY Expression Affects Stress Response and Emotion" Nature, Apr. 2008, 452, pp. 997-1002.

Joshi et al., "P276-00, A Novel Cyclin-Dependent Inhibitor Induces G1-G2 Arrest, Shows Antitumor Activity on Cisplatin-Resistant Cells and Significant in Vivo Efficacy in Tumor Models", Mol. Can. Ther., Mar. 2007, 6(3), pp. 926-934.

Sasai et al., "Aurora-C kinase is a novel chromosomal passenger protein that can complement aurora-B kinase function in mitotic cells" Cell Motility and the Cytoskeleton, 2004, 59, pp. 249-263.

Hirota et al., "Aurora-A and an Interacting Activator, the LIM Protein Ajuba, Are Required for Mitotic Commitment in Human Cells," Cell, 2003, 114, pp. 585-598.

Dutertre et al., "Phosphorylation of CDC25B by Aurora-A at the Centrosome Contributes to the G2-M Transition," J. Cell. Sci., 2004, 117(12), pp. 2523-2531.

Carmena et al., "The Cellular Geography of Aurora Kinases", Nat. Rev. Mol. Cell Biol., 2003, 4, pp. 842-854.

Schumacher et al., "AIR -2 : An Aurora/Ipl1-related protein Kinase Associated with Chromosomes and Midbody Microtubules Is Required for Polar Body Extrusion and Cytokinesis in Caenorhabditis elegans Embryos" J. Cell. Biol., 1998, 143, pp. 1635-1646.

Terada et al., "AIM-1: a mammalian midbody-associated protein required for cytokinesis", EMBO J., 1998, 17, pp. 667-676.

Giet et al, "Drosophila Aurora B Kanse Is Required for Histone H3 Phosphorylation and Condensin Recruitment during Chromosome Condensation and to Organize the Central Spindle during Cytokinesis", J. Cell Biol., 2001, 152, pp. 669-681.

Giet et al., "Aurora kinases, aneuploidy and cancer, a coincidence or a real link?", Trends. Cell Biol. 2005, 5, pp. 241-250.

Duesberg et al., "Cancer Drug Resistance: The Central Role of the Karyotype," Drug Resist Updat., 2007, 10, pp. 51-58.

Keen et al., "Aurora-kinase Inhibitors As Anticancer Agents", Nature Rev., 2004, 4, pp. 927-936.

Ota et al., "Increased Mitotic Phosphorylation of Histone H3 Attributable to AIM-1/Aurora-B Overexpression Contributes to Chromosome Number Instability", Cancer Res., 2002, 62, pp. 5168-5177.

Vischioni et al., "Frequent overexpression of aurora B kinase, a novel drug target, in non-small cell lung carcinoma patients", Mol. Cancer Ther., 2006, 5, pp. 2905-2913.

Smith et al., "Overexpression of aurora B kinase (AURKB) in primary non-small cell lung carcinoma is frequent, generally driven from one allele, and correlates with the level of genetic instability", Br. J. Cancer, 2005, 93, pp. 719-729.

Liu et al., "Aurora-A Abrogation of p53 DNA Binding and Transactivation activity by Phosphorylation of Serine 215", J Biol Chem., 2004, 279, pp. 52175-52182.

Katayama et al., "Phosphorylation by aurora kinase A induces Mdm2-mediated destabilization and inhibition of p53", Nat. Genetics, 2004, 36, pp. 55-62.

Ouchi et al., "BRCA1 Phosphorylation by Aurora-A in the Regulation of G2 to M Transition", J Biol. Chem., 2004, 279, pp. 19643-19648.

Andrews, "Aurora kinases: shining lights on the therapeutic horizon?" Oncogene, 2005, 24, pp. 5005-5015.

Ditchfield et al., "Aurora B couples chromosome alignment with anaphase by targeting BubR1, Mad2 and Cenp-E to kinetochores", J. Cell Biol., 2003, 161, pp. 267-280.

Hauf et al., "The small molecule Hesperadin reveals a role for Aurora B in correcting kinetochore-microtubule attachment and in maintaining the spindle assembly checkpoint", J. Cell Biol., 2003, 161, pp. 281-294.

Harrington et al., "VX-680, A Potent and Selective Small-molecule Inhibitor of the Aurora kinases, suppresses tumor growth in vivo", Nat. Med., 2004, 10, pp. 262-267.

Bundy et al., "C/EBPbeta-2 confers EGF-independent growth and disrupts the normal acinar architecture of human mammary epithelial cells", Mol. Cancer, 2005, 4(43), pp. 1-17.

Rusch et al., "The epidermal growth factor receptor and its ligands as therapeutic targets in human tumors", Cytokine Growth Factor Rev., 1996, 7(2), pp. 133-141.

Salomon et al., "Epidermal growth factor related peptides and their receptors in human malignancies", Crit. Rev. Oncol. Hematol., 1995; 19, pp. 183-232.

Doroshow "Targeting EGFR in Non-Small Lung cancer", N. Engl. J. Med., 2005, 353(2), pp. 200-202.

Sui et al., "A DNA vector-based RNAi technology to suppress gene expression in mammalian cells", Proc. Natl. Acad. Sci., USA, 2002, 99, pp. 5515-5520.

Henschel., et al., "DEQOR: a web-based tool for the design and quality control of siRNAs", Nucleic Acids Res., 2004, 32, pp. W113-W120.

Ui-Tei et al., "Guidelines for the Selection of Highly Effective siRNA Sequences for Mammalian and Chick RNA Interference," Nucleic Acids Res., 2004, 32(3), pp. 936-948.

Elbashir et al., "Analysis of Gene Function in Somatic Mammalian Cells Using Small Interfering RNAs", Methods, 2002, 26(2), pp. 199-213.

Hornung et al., "Sequence-Specific Potent Induction of IFN-αby Short Interfering RNA in Plasmacytoid Dendritic Cells Through TLR7", Nature Medicine, 2005, 11, pp. 263-270.

Judge et al., "Sequence-dependent Stimulation of the Mammalian Innate Immune Response by Synthetic siRNA," Nat. Biotechnol., 2005, 23(4), pp. 457-462.

Sorrentino R. et al., "Aurora B overexpression associates with the thyroid carcinoma undifferentiated phenotype and is required for thyroid carcinoma cell proliferation." J. Clinical Endocrinology, 90(2), 2005, 90(2), pp. 928-935.

Tsuno et al., "Inhibition of Aurora-B function increases formation of multinucleated cells in p53 gene deficient cells and enhances antitumor effect of temozolomide in human glioma cells", J. Neurooncol., 2007, 83, pp. 249-258.

Fancelli et al., "Inhibitors of Aurora kinases for the treatment of cancer", Expert Opinion, 2005, 15(9), pp. 1169-1182.

Fu et al, "Targeting Aurora kinases in ovarian cancer", Expert Opinion, 2006, 10(1), pp. 77-85.

\* cited by examiner 50 kDa
41 kDa

170kDa
50kDa

Figure 39.
A.
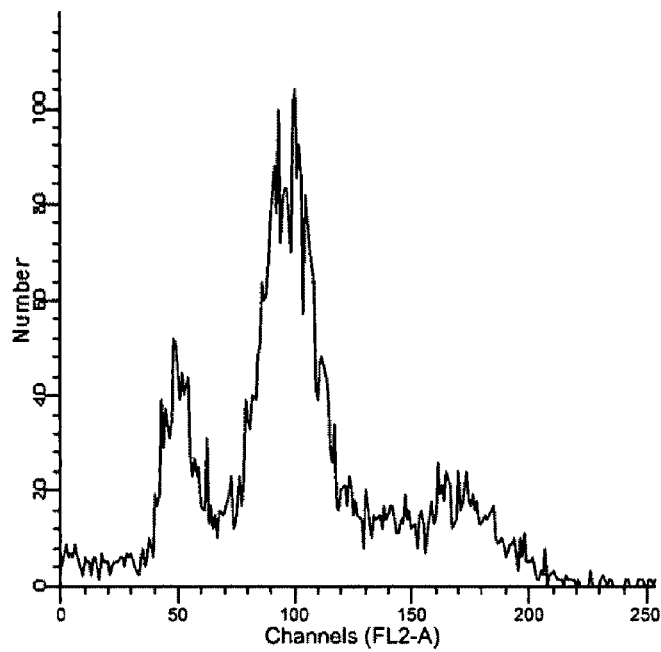
B.
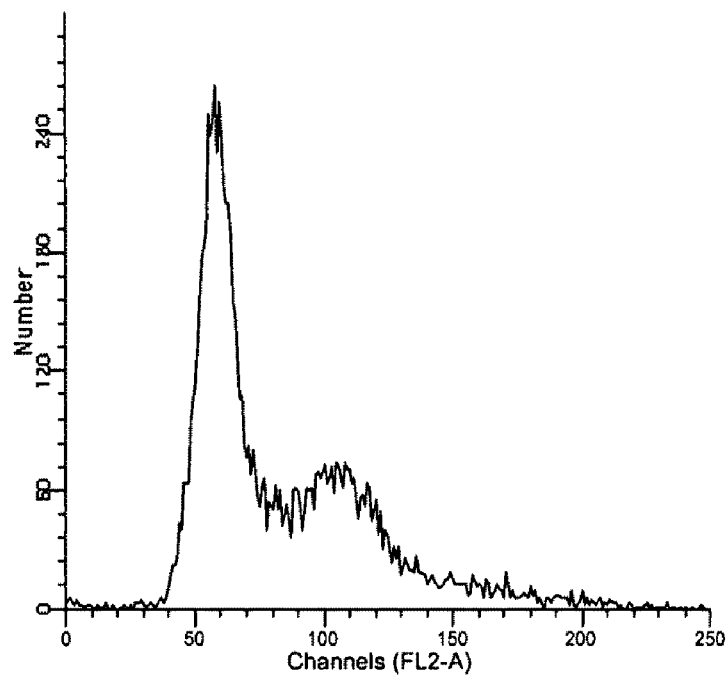

SEQUENCE LISTING

<160> NUMBER OF SEQ ID NOS: 22

<210> SEQ ID NO 1
<211> LENGTH: 19
<212> TYPE: DNA
<213> ORGANISM: Homo sapiens

<400> SEQUENCE: 1
ttgatgactt tgagattgg                                            19

<210> SEQ ID NO 2
<211> LENGTH: 20
<212> TYPE: DNA
<213> ORGANISM: Homo sapiens

<400> SEQUENCE: 2
ggaggaggat ctacttgatt                                           20

<210> SEQ ID NO 3
<211> LENGTH: 24
<212> TYPE: DNA
<213> ORGANISM: Homo sapiens

<400> SEQUENCE: 3

```
gaggatctac ttgattctag agta                                           24

<210> SEQ ID NO 4
<211> LENGTH: 19
<212> TYPE: RNA
<213> ORGANISM: Homo sapiens

<400> SEQUENCE: 4
aagaaaguuu gccaaggca                                                 19

<210> SEQ ID NO 5
<211> LENGTH: 21
<212> TYPE: DNA
<213> ORGANISM: Homo sapiens

<400> SEQUENCE: 5
gagtgcaacc agcaacaatt c                                              21

<210> SEQ ID NO 6
<211> LENGTH: 25
<212> TYPE: DNA
<213> ORGANISM: Homo sapiens

<400> SEQUENCE: 6
gcaacatctc cgaaagccaa caagg                                          25

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
uugaugacuu ugagauuggt t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
ccaaucucaa agucaucaat t                                              21

<210> SEQ ID NO 9
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
```
ggaggaggau cuacuugauu tt                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
aaucaaguag auccuccucc tt                                              22

<210> SEQ ID NO 11
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
ggaggaucua cuugauucua gagta                                           25

<210> SEQ ID NO 12
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uacucuagaa ucaaguagau ccuccuc                                         27

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
aagaaaguuu gccaaggcat t                                               21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
ugccuuggca aacuuucuut t                                               21

```
<210> SEQ ID NO 15
<211> LENGTH: 20
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
gagugcaacc agcaauuctt                                              20

<210> SEQ ID NO 16
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
gaauuguugc ugguugcacu ctt                                          23

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gcaacaucuc cgaaagccaa caagg                                        25

<210> SEQ ID NO 18
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccuuguuggc uuucggagau guugcuu                                      27

<210> SEQ ID NO 19
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
gagaguauca gggacuuguu ctt                                          23

<210> SEQ ID NO 20
<211> LENGTH: 23
<212> TYPE: DNA
<213> ORGANISM: Artificial Sequence
```

```
-continued

<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
gaacaagucc cugauacucu ctt                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
gacgcaucaa uaggccaaua ctt                                              23

<210> SEQ ID NO 22
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
guauuggccu auugaugcgu ctt                                              23
```

RNA INTERFERENCE MEDIATED INHIBITION OF AURORAKINASE B AND ITS COMBINATIONS AS ANTICANCER THERAPY

CROSS-REFERENCE TO RELATED PATENT APPLICATIONS

This application claims benefit of provisional Indian Application No. 974/MUM/2006, filed Jun. 21, 2006, which is hereby entirely incorporated by reference.

FIELD OF THE INVENTION

The present invention relates to use of short nucleic acid molecules, such as short interfering nucleic acid (siNA) molecules, for modulating gene and protein expression, including compounds, compositions and uses of small nucleic acid molecules to modulate Aurora B (AurkB) expression. The compounds and methods of the present invention have applications in cancer therapy either alone or in combination with other therapies.

BACKGROUND OF THE INVENTION

The Aurora kinases are a family of serine/threonine kinases. Aurora A and B kinase are associated with mitotic events of cell cycle, while Aurora C kinase is expressed only in testis (Sasai K, Katayama H, Stenoien D L, Fujii S, Honda R, Kimura M, et al, Aurora-C kinase is a novel chromosomal passenger protein that can complement Aurora-B kinase function in mitotic cells. *Cell Motil. Cytoskeleton*, 2004; 59:249-263). Aurora-A kinases, also called Aurora-2, STK6, ARK1 and Aurora/IPL-1 related kinase, associates with centrosomes and microtubules during mitosis. Aurora A kinase (hereinafter "Aurora A") localizes to centrosomes and regulates the association between cell cycle machinery and centrosomes (Hirota T, Kunitoku N, Sasayama T, Marumoto T, Zhang D, Nitta M. Aurora-A and an Interacting Activator, the LIM Protein Ajuba, Are Required for Mitotic Commitment in Human Cells. *Cell* 2003; 114: 585-598; Dutertre S, Cazales M, Quaranta M, Froment, C, Trabut, V, Dozier, C. et al. Phosphorylation of CDC25B by Aurora-A at the centrosome contributes to the G2-M transition. *J. Cell. Sci.* 2004; 117: 2523-2531).

Aurora B kinases, also known as Aurorakinase B, Aurora B, Aurora-1, and hereinafter "AurkB", localizes to the kinetochores from prophase to metaphase and to the central spindle and the midbody in cytokinesis (Carmena M. and Eamshaw W C. The cellular geography of aurora Kinases. *Nat. Rev. Mol. Cell. Biol* 2003; 4: 842-854). AurkB associates with chromosome passenger proteins, inner centromere protein (INCENP), Survivin and Borealin protein to form a quaternary chromosome passenger complex which, along with its sub complexes (AurkB and INCENP) are thought to be required for spindle check point, cytokinesis and phosphorylation of Histone H3, respectively. (Schumacher J M, Golden A, and Donovan P. AIR-2: An Aurora/Ipl1-related protein Kinase associated with chromosomes and midbody microtubules is required for polar body extrusion and cytokinesis in Caneorhabditis elegans embryos. *J. Cell. Biol.* 1998; 143: 1635-1646; Terada Y, Tatsuka M, Suzuki F, Yasuda Y, Fujita S, and Otsu M. AIM-1: a mammalian midbody-associated protein required for cytokinesis. *EMBO J.* 1998; 17: 667-676; Giet R and Glover D M. Drosophilia aurora B Kinase is required for histone H3 phosphorylation and condensing recruitment during chromosome condensation and to organize the central spindle during cytokinasis. *J. Cell Biol* 2001; 152: 669-682). AurkB phosphorylates MCAK and thus plays a vital role in regulation of bi-orientation during mitosis (Giet R, Petretti C and Prigent C. Aurora Kinases, aneuploidy and cancer, a coincidence or a real link? *Trends. Cell Biol.* 2005; 5: 241-250).

Any discrepancy in functioning of Aurora kinases can lead to mitotic catastrophe resulting in anueploidy or polyploidy, a hallmark of cancer. Indeed, chromosomal instability cause cancer and is clearly associated with cancer evolution and thus resistance to treatment (Duesberg P et al., "The chromosomal basis of cancer" *Cell Oncol.* 2005; 27(5-6):293-318; Duesberg P et al., "Cancer drug resistance: The central role of the karyotype." *Drug Resist Updat.* 2007 Mar. 26). Aurora kinases have been linked to the chromosomal instability. In addition, malfunctions of Aurora kinases are found in a number of cancers, such as non-small cell lung cancer, epidermal, prostate, colon, pancreatic, ovary, breast and oral cancers including all head and neck cancers. (Keen N. and Taylor S. Aurora-kinase inhibitors as anticancer agents. *Nature Rev* 2004; 4: 927-936). Inhibition of AurkB leads to improper segregation of sister chromatids and failure of cytokinesis. Over-expression of AurkB has been linked to cell proliferation and development of aggressive tumors leading to malignancy. (Ota T, Suto S, Katayama H, Han Z, Suzuki F, Maeda M et al. Increased mitotic phosphorylation of histone H3 attributable to AIM-1/Aurora-B over expression contributes to chromosome number instability. *Cancer Res* 2002; 62: 5168-5177; Vischioni B, Oudejans J J, Vos W, Rodriguez J A and Giaccone G. Frequent overexpression of aurora B Kinase, a novel drug target, in non-small cell lung carcinoma patients. *Mol. Cancer. Ther.* 2006; 5: 2905-2913; Smith S L, Bowers N L, Betticher D C, Gautschi O, Ratschiller D, Hoban P R. Overexpression of aurora B Kinase (AURKB) in primary non-small cell lung carcinoma is frequent, generally driven from one allele, and correlates with the level of genetic instability. *Br. J. Cancer* 2005; 19:719-29). Studies so far have not indicated whether the malfunctioning of Aurora is a cause or consequence of cancers. AurkB is intimately involved in preventing chromosomal instability. (Liu Q, Kaneko S, Yang L, Feldman R I, Nicosia S V, Chen J et al. Aurora-A Abrogation of p53 DNA binding and transactivation activity by phosphorylation of serine 215. *J Biol. Chem.* 2004; 279: 52175-52182; Katayama H, Sasai K, Kawai H, Yuan Z, Bondaruk J et al. BRCAI phosphorylation by aurora kinase A induces Mdm2-mediated destabilization and inhibition of p53. *Nat. Genetics* 2004; 36: 55-62; Ouchi M, Fujiuchi N, Sasai K, Katayama H, Minamishima Y A et al. BRCAI phosphorylation by Aurora-A in the regulation of G2 to M transition. *J. Biol. Chem.* 2004; 279:19643-19648). Survivin, part of AurkB complex, is a key protector against apoptosis and/or mitotic catastrophe (Andrews P D. Aurora Kinases: shining lights on the therapeutic horizon? *Oncogene* 2005; 24: 5005-5015). AurkB therefore appears to have a direct role in tumorigenesis.

Aurora inhibitors have been reported several authors (Ditchfield C, Johnson V L, Tighe A, Ellston R, Haworth C, Johnson T et al. Aurora B couples chromosome alignment with anaphase by targeting BubR1, Mad2 and Cenp-E to kinetochores. *J Cell Biol* 2004; 161: 267-280; Hauf S, Cole R W, Terra S, Zimmer C, Schnapp G, Walter R et al. The small molecule Hesperadin reveals a role for Aurora B in correcting kinetochore-microtubule attachment and in maintaining the spindle assembly checkpoint. *J Cell Biol* 2003; 161: 281-294 and Harrington E A, Bebbington D, Moore J, Rasmussen R K, Ajose-Adeogun A O, Nakayama, T. VX-680, a potent and selective small-molecule inhibitor of the Aurora kinases, suppresses tumor growth in vivo. *Nat. Med.* 2004; 10:262-267). These inhibitors include ZM447439 (by AstraZeneca) which shows inhibition of 13 other kinases apart from Aurora. AZD 1152 (AstraZeneca) has been shown to inhibit spindle aggregation at the time of mitosis and is being evaluated to determine its effect as a specific inhibitor of Aurora kinase and its impact on cell division in proliferating tumors. Hesperadin (by Boehringer Ingelheim) inhibits AurkB and 25 other kinases, but not Aurora A or C, and causes only polyploidy with no apparent loss to cell viability.

VX-680 (Vertex) inhibits all three Aurora and, in a panel of cancer cells, was found to inhibit proliferation, increase apoptosis induction, and induce tumor cell death. Merck is presently conducting three clinical studies of VX-680 in patients with hematologic cancers, recurrent or non-responsive solid tumors, or cancers for which standard therapy does not currently exist. In these studies, the safety and tolerability of VX-680 are being evaluated when administered as either a 24-hour continuous infusion or as a 5-day continuous infusion. Of the Aurora inhibitors in clinical trials, only VX-680 is highly specific for Aurora, but is associated with toxic bone marrow side effects, and the mechanism of tumor cell death is not completely understood (Giet R, Petretti C and Prigent C. Aurora Kinases, aneuploidy and cancer, a coincidence or a real link? *Trends. Cell Biol* 2005; 5: 241-250).

Additional Aurora inhibitors have been described. Japanese patent application JP 2005-278472 describes a peptide that inhibits activities of AurkB in the inner centromere protein, specifically bonding to the Aurora protein; and also describes a medicinal composition, screening methods, and kits. Japanese patent application JP 2005-320351 describes a process for preparing tri- and tetra-substituted pyrimidines, the use in preparing Aurora kinase inhibitors, and methods of treatment. US patent application 20050267065 describes compositions and methods for modulating the expression of AurkB, including using chemically modified nucleotides, including small interfering nucleotides. The use of chemically modified nucleotides poses a potential risk of unwanted side effects.

The epidermal growth factor receptor (EGFR, also known as ErbB-1, or HER1 in humans) is a protein tyrosine kinase. Activation of EGFR leads to transmission of proliferative signals to the nucleus and, via activation of transcription factors, leads to increased proliferation, increased migration, increased adhesion, increased angiogenesis and inhibition of programmed cell death pathways (Bundy, L., Wells, S., Sealy, L. "C/EBPbeta-2 confers EGF-independent growth and disrupts the normal acinar architecture of human mammary epithelial cells," *Mol. Cancer.* 2005; 4: 43). EGFR is over-expressed in a number of cancers such as head and neck squamous cell carcinoma (HNSCC), non-small cell lung carcinoma (NSCLC), prostate, gastric, epidermal and skin cancers. EGFR is expressed constitutively in many highly aggressive tumors (Rusch V, Mendelsohn J, Dmitrovsky E. "The epidermal growth factor receptor and its ligands as therapeutic targets in human tumors." *Cytokine Growth Factor Rev* 1996; 7: 133-41; Salomon D S, Brandt R, Ciardiello F, Normanno N. "Epidermal growth factor related peptides and their receptors in human malignancies." *Crit Rev Oncol Hematol* 1995; 19: 183-232) and tumors showing over expression of EGFR are often found to be resistant to chemotherapeutic drugs (James H. Doroshow "Targeting EGFR in Non-Small Lung cancer." *N. Engl. J. Med.* 2005; 353(2):200-2002).

EGFR inhibitors such as cetuximab, erbolitin, etc, are known. To enhance the tumoricidal affects of EGFR inhibitors, therapeutic treatments often include use of cytotoxic chemotherapeutic drugs such as cisplatin, foldfox, etc. However, in randomized clinical trials EGFR inhibitors when combined with cytotoxic chemotherapy, no advantage was demonstrated over standard chemotherapy alone (Sui G., Soohoo C., el Affar B., Gay F., Shi Y., Forrester W. C. & Shi Y. A DNA vector-based RNAi technology to suppress gene expression in mammalian cells. *Proc. Natl. Acad. Sci. USA* 2002; 99, 5515-5520). Accordingly, there is also a need for improved EGFR inhibitors.

Chemically synthesized short nucleic acid molecules, such as siNAs, can specifically and effectively direct homology-specific post transcriptional gene silencing, and therefore may be used as highly effective, selective and potent therapeutics, with minimal side effects. A molecule that specifically inhibits AurkB can block the mechanics of cell division, and therefore is very useful in combination therapy. Similarly, siNA may be used to block EGFR expression.

The present invention provides potent short nucleic acid molecules without any chemical modification having high stability and specificity for AurkB and or EGFR, and are useful as therapeutics alone, or in combination with other therapies for cancer.

SUMMARY OF THE INVENTION

The present invention provides short nucleic acid molecules for modulation of AurkB gene expression. In related embodiments, the present invention provides AurkB-targeting short nucleic acid molecules for the treatment of cancer, including cervical, prostrate, breast, lung and oral cancer. Such molecules may be used alone or in combination with other treatments for the management and treatment of cancer. In one embodiment, the AurkB-targeting short nucleic acid molecule is provided in combination with a short nucleic acid molecule that targets EGFR. In other embodiments, short nucleic acids of the present invention may be combined with conjugates such as lipids, polymers and monoclonal antibodies.

The present invention includes short nucleic acid molecules which are specifically targeted. In some embodiments, the short nucleic acid molecules are RNA, including siRNA. The present invention also includes advantageously stable and/or potent nucleic acid molecules for inhibition of AurkB and EGFR, and for the related treatment of cancer.

In some embodiments, the present invention provides siNAs having between 19 to 30 nucleotides, between 25 and 29 nucleotides, or having 27 nucleotides, where the sequence is designed for better stability and efficacy in knockdown (i.e., reduction) of AurkB gene expression. Such siNAs can be used alone or in combination with other therapies. The present invention provides stable compositions of siNA with or without conjugation with cholesterol. In related embodiments, the invention encompasses compounds, compositions and uses of 27-mer short interfering nucleic acid molecules in modulation of AurkB gene expression. The compounds of the present invention are useful in therapy of cancer either alone or in combination with other treatments or therapies.

In one embodiment the short nucleic acid molecules of the present invention is also a short interfering nucleic acid (siNA), a short interfering RNA (siRNA), a double stranded RNA (dsRNA), a micro RNA (μRNA), and/or a short hairpin RNA (shRNA) molecule. The short nucleic acid molecules can be unmodified or modified chemically. In the some embodiments the present invention relates to short interfering RNA having 27 nucleotides.

In one embodiment, the nucleic acid molecule of the present invention has between 19 to 30 nucleotides, between 25 and 29 nucleotides, or 27 nucleotides. In one embodiment, the nucleic acid molecule of the present invention comprises 19-30 nucleotides complementary to RNA having an AurkB nucleic acid sequence.

Nucleotides of the present invention can be chemically synthesized, expressed from a vector, or enzymatically synthesized.

In one embodiment, a siRNA molecule of the invention comprises a double stranded RNA wherein one strand of the RNA is complimentary to the RNA of AurkB. In another embodiment, a siRNA molecule of the invention comprises a double stranded RNA wherein one strand of the RNA comprises a portion of a sequence of RNA having AurkB sequence.

In one embodiment, the invention targets AurkB as set forth in GenBank Accession Number NM-004217. However, the present invention is not limited to nucleotides targeting one variant of AurkB, but also includes nucleotides that target AurkB-related molecules including single nucleotide polymorphisms of AurkB, AurkB homologs, and AurkB splice and transcript variants. The present invention also contemplates nucleotides that target genes involved in AurkB regulatory pathway as a means of regulating AurkB.

In other embodiments, the present invention provides compositions and methods used to regulate AurkB. AurkB may be regulated by a small nucleic acid molecule which targets AurkB directly, or by targeting molecules which regulate the AurkB pathway. Small nucleic acid molecule that target AurkB may be used alone, or in combination with other small nucleic acid molecules or small chemical molecules. In related embodiments, the targeting of AurkB is used to regulate cancer or disease states that respond to modulation of AurkB expression levels in the cell.

In some embodiments, chemically synthesized siNA of 27 nucleotides in length are used to reduce expression levels of AurkB either alone or in combination with other small nucleic acid molecules directed against genes that are involved in various cancers, such as EGFR. In some embodiments, small nucleic acid molecules disclosed in Tables 1 or 2 may be used alone or in combination for cancer therapy.

In further related embodiments, cancer regulation by siNA is suitable for cancer management and treatment. Thus, the present invention provides short nucleic acid molecules for treatment of cancer such as cervical, oral, lung, skin and prostate cancers.

In another embodiment, the present invention provides techniques for validating the efficacy of siNA using biomarkers of cancer. For example, present invention provides the efficacy testing using specific biomarkers of cancer such as PCNA and Ki-67 antigen expression.

In one embodiment, the present invention provides a combination of small nucleic acid molecule targeting AurkB and EGFR as a treatment for cancers. In some embodiments, suitable small nucleic acid molecules include those listed in Tables 1 and 2.

In one embodiment, the invention features a mammalian cell, for example a human cell, including a small nucleic acid molecule of the invention.

The present invention features a method of down-regulating AurkB activity in a cell, comprising contacting the cell with an enzymatic nucleic acid molecule or antisense nucleic acid molecule, or other nucleic acid molecule of the invention, under conditions suitable for down-regulating of Aurorakinase activity.

The present invention also features a method of treatment of a subject having a condition associated with elevated AurkB, comprising contacting cells of the subject with an enzymatic nucleic acid molecule or antisense nucleic acid molecule or other nucleic acid molecule of the invention under conditions suitable for the treatment.

The present invention features a method of down-regulating (also called "knocking down") Aurorakinase activity in a cell, comprising contacting the cell with an enzymatic nucleic acid molecule or antisense nucleic acid molecule or other nucleic acid molecule of the invention, under conditions suitable for down-regulating Aurorakinase activity.

In one embodiment, the present invention also features a method of treatment of a subject having a condition associated with the level of AurkB, comprising contacting cells of the subject with the enzymatic nucleic acid molecule or antisense nucleic acid molecule or other nucleic acid molecule of the invention, under conditions suitable for the treatment.

In one embodiment, a method of treatment of the invention comprises the use of one or more drug therapies under conditions suitable for said treatment.

The present invention also features a method for treatment of cancer, for example breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer, comprising administering to a subject an enzymatic nucleic acid molecule or antisense nucleic acid molecule or other nucleic acid molecule of the invention under conditions suitable for said treatment.

In another embodiment, other drug therapies contemplated by the invention include monoclonal antibodies, chemotherapy, or radiation therapy or a combination thereof.

The present invention features compositions comprising the enzymatic nucleic acid and/or antisense nucleic acid molecules of the invention in a pharmaceutically acceptable carrier.

The invention also features a method of administering to a cell, such as mammalian cell (e.g., a human cell) a nucleic acid of the invention. Such a cell can be in culture or in a mammal, such as a human. The method of administering comprises contacting the cell with the enzymatic nucleic acid molecule or antisense molecule or other nucleic acid molecule of the invention under conditions suitable for such administration. The method of administration can be in the presence of a delivery reagent, for example a lipid, cationic lipid, phospholipid, or liposome.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

4A Transfected with Mock (siRNA 7 and 8). Arrowhead indicates cells firmly adhered to the substratum and growing normally.

4B—siRNA 3 transfected cells. Arrowhead indicates cells assuming spherical shape before detaching from substratum and disintegrating.

Figure 5:
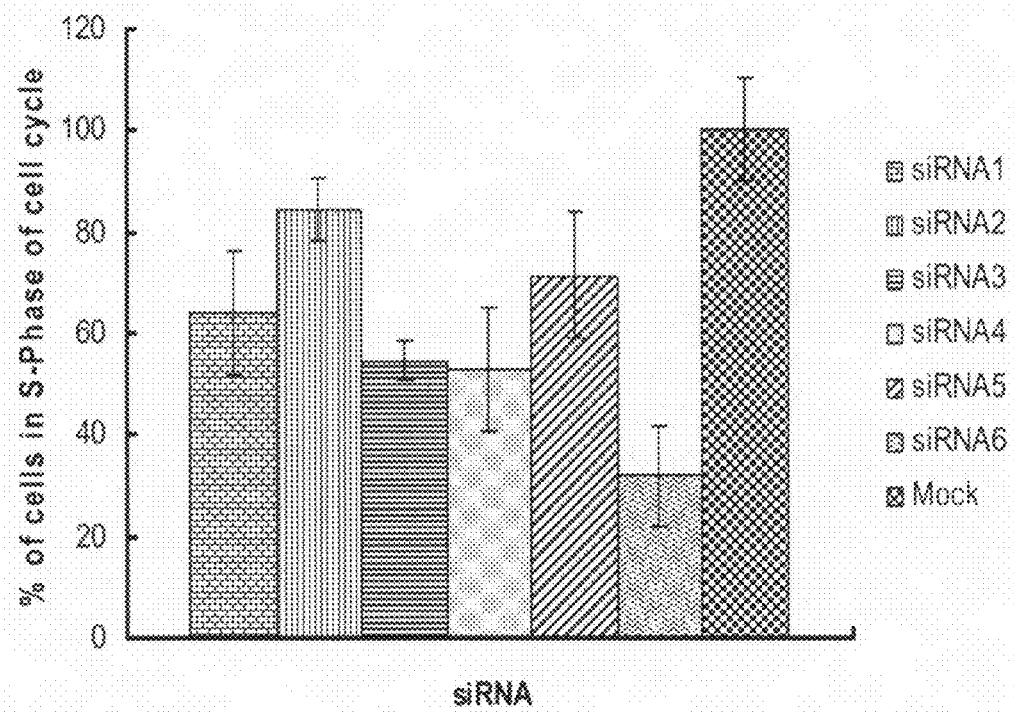

FIG. 5. BrdU incorporation into PC3 (prostate cancer cell line) treated with siRNA of different lengths. Statistical significance (two tailed t-test, $P \leq 0.05$) was found between mock treated and all siRNA treated cells, between siRNA 2 and 3, between siRNA 4 and 5, between siRNA 5 and 6, as well as between siRNA 4 and 6.

Figure 6:
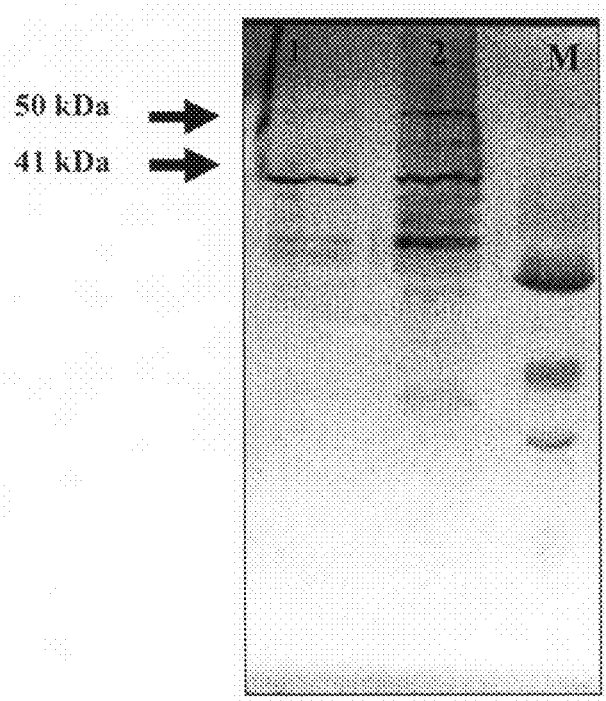

FIG. 6. Inhibition of AurkB expression after transfection with siRNA 3. Lane 1. siRNA 3 transfected A549 cell line where arrow head indicates faint band of AurkB, a 41 kDa protein. Lane 2. Mock treated sample where AurkB protein was detected in fairly good quantities over the siRNA treated samples. Lane 3. Rainbow low molecular weight markers.

Figure 7:
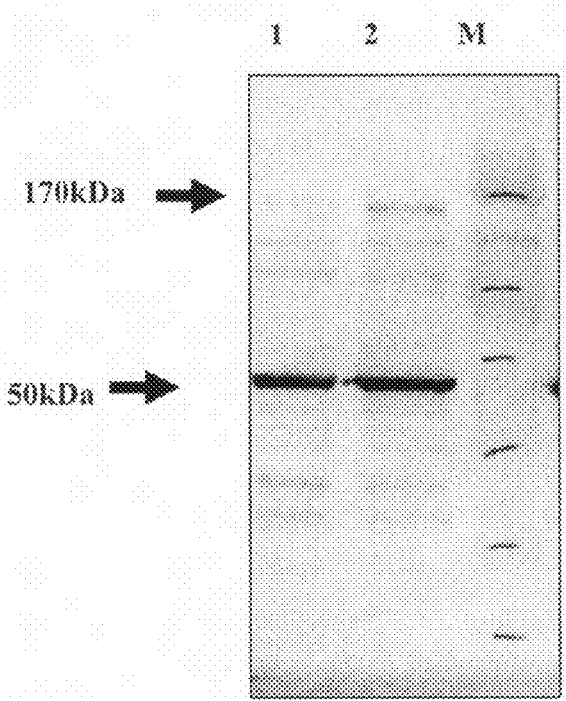

FIG. 7. Inhibition of EGFR expression after transfection with siRNA 6. Lane 1. siRNA 6 transfected A549 cell line where arrow head indicates missing band of EGFR, a 170 kDa protein. Lane 2. Mock treated sample where EGFR protein was detected in fairly good quantities over the siRNA treated samples. Lane 3. Rainbow high molecular weight markers.

Figure 8:
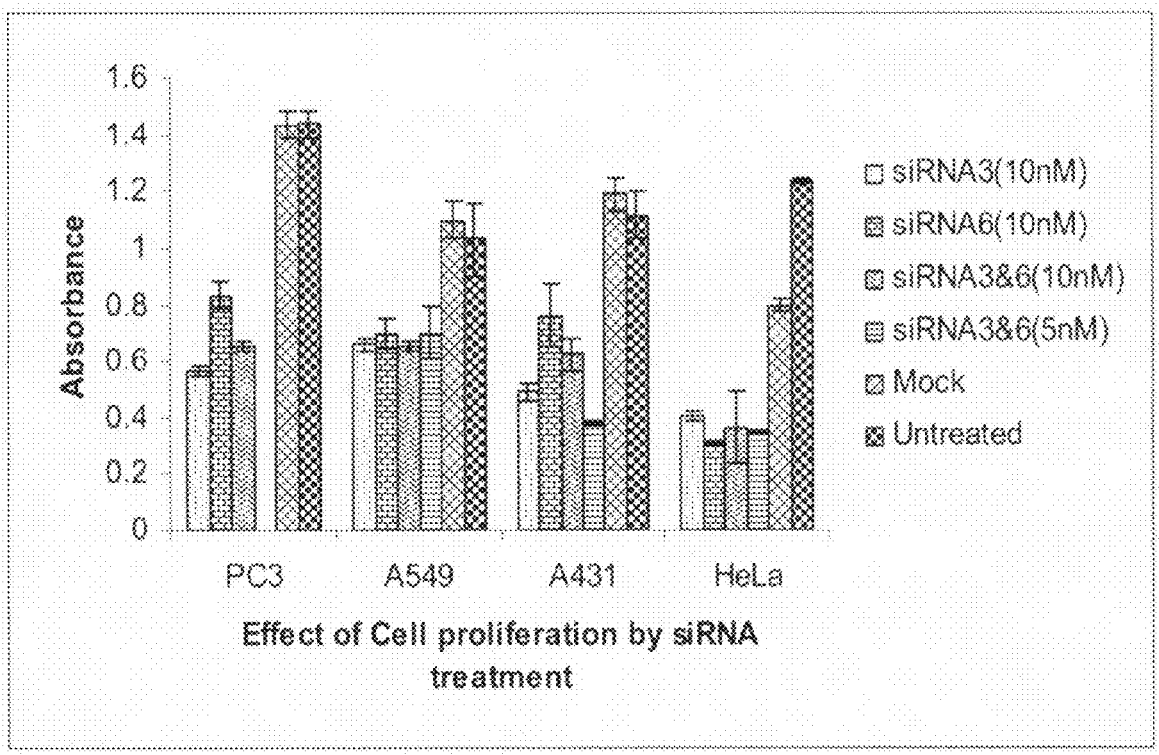

FIG. 8. Metabolic activity of different cell lines treated with different siRNA. Statistical significance was determined between mock treated cells vs siRNA transfected cells by paired two tail t-test where $P \leq 0.05$.

Figure 9:
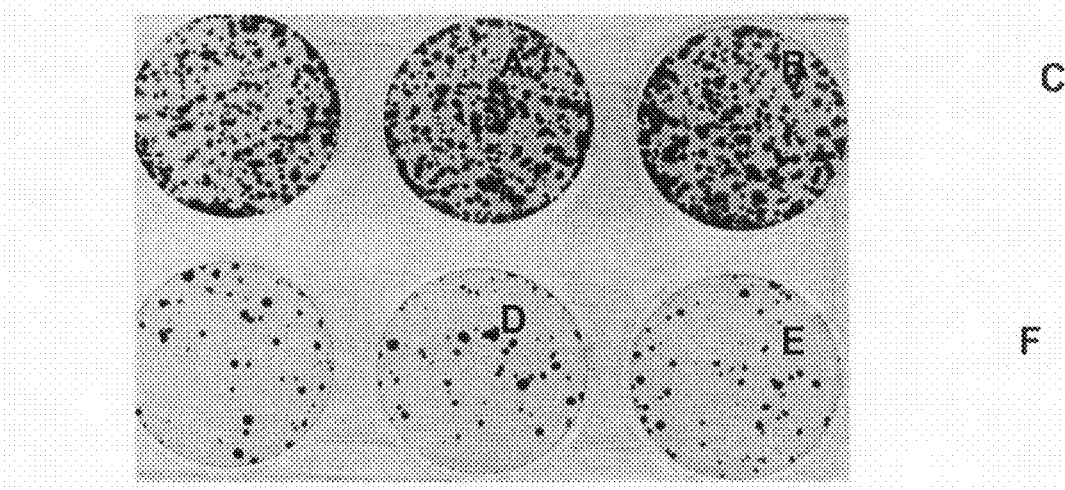

FIG. 9. Colony formation assay of PC3 cells transfected with mock (A-C) or siRNA 3 and 6 (D-F)

Figure 10:
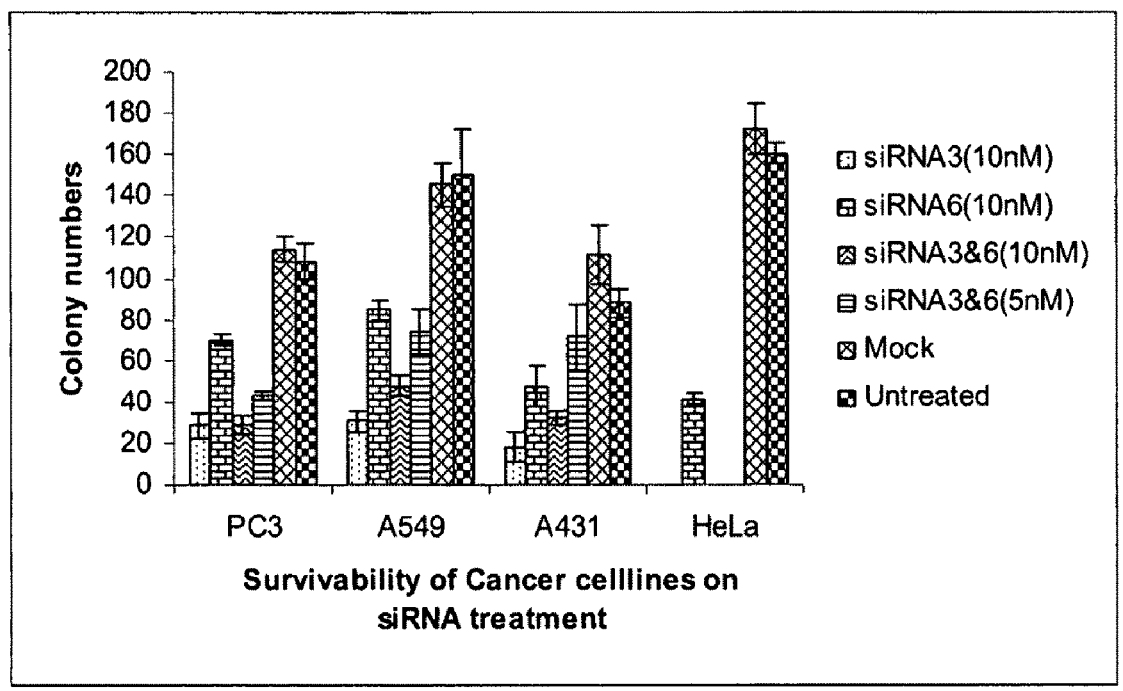

FIG. 10. Colony forming efficiency of different cell lines treated with siRNA 3 (10 nM), siRNA 6 (10 nM) and a combination of siRNA 3 and 6 at 10 nM and 5 nM concentrations each. Significant inhibition (two tail t-test, $P \leq 0.05$) of colony forming ability was observed in all the cells treated with siRNA in comparison with that of mock treated cells.

Figure 11:
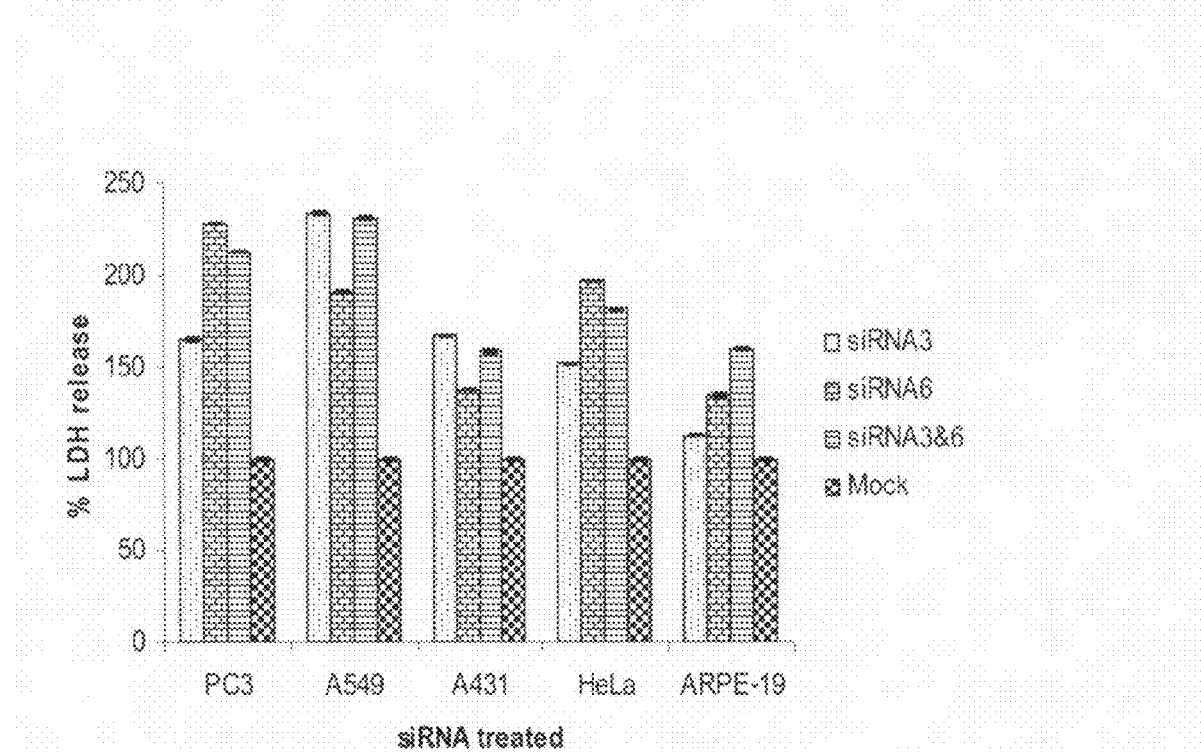

FIG. 11. LDH release following repression of AurkB and/or EGFR.

Figure 12:
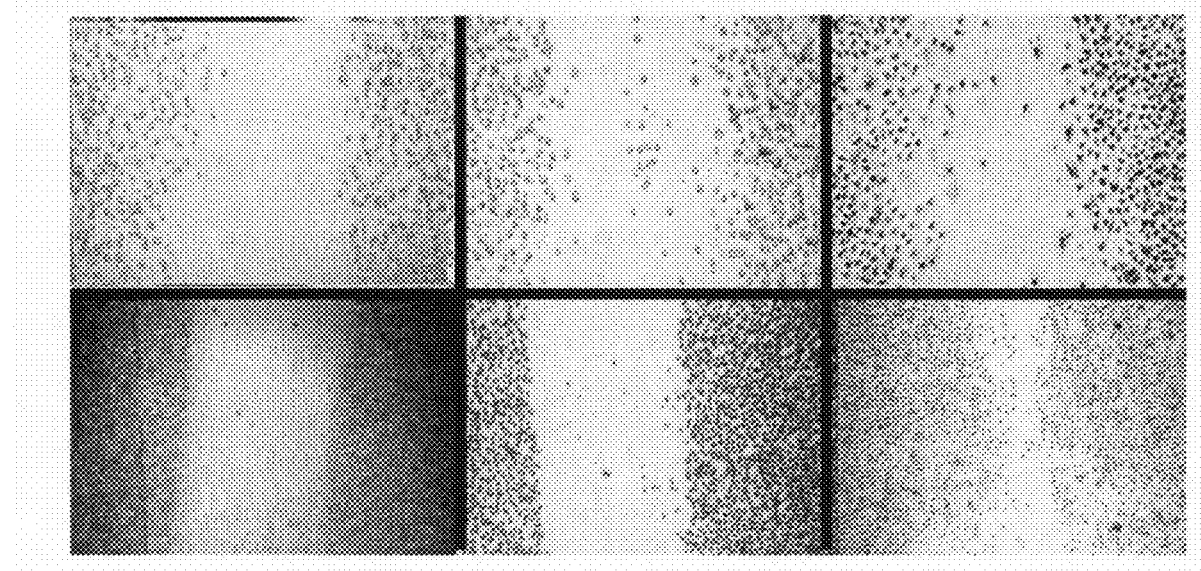

FIG. 12. Scratch assay showing migration of cells from periphery of scratch, over time, in A549 cell line transfected with SIRNA 3 and 6 combination. A-C: siRNA 3 and 6 transfected A549 cell line. D-F: Mock transfected cell line. A and D: 0 h of scratch infliction. B and E: 8 h of scratch infliction. C and F: 24 h of scratch infliction.

Figure 13:
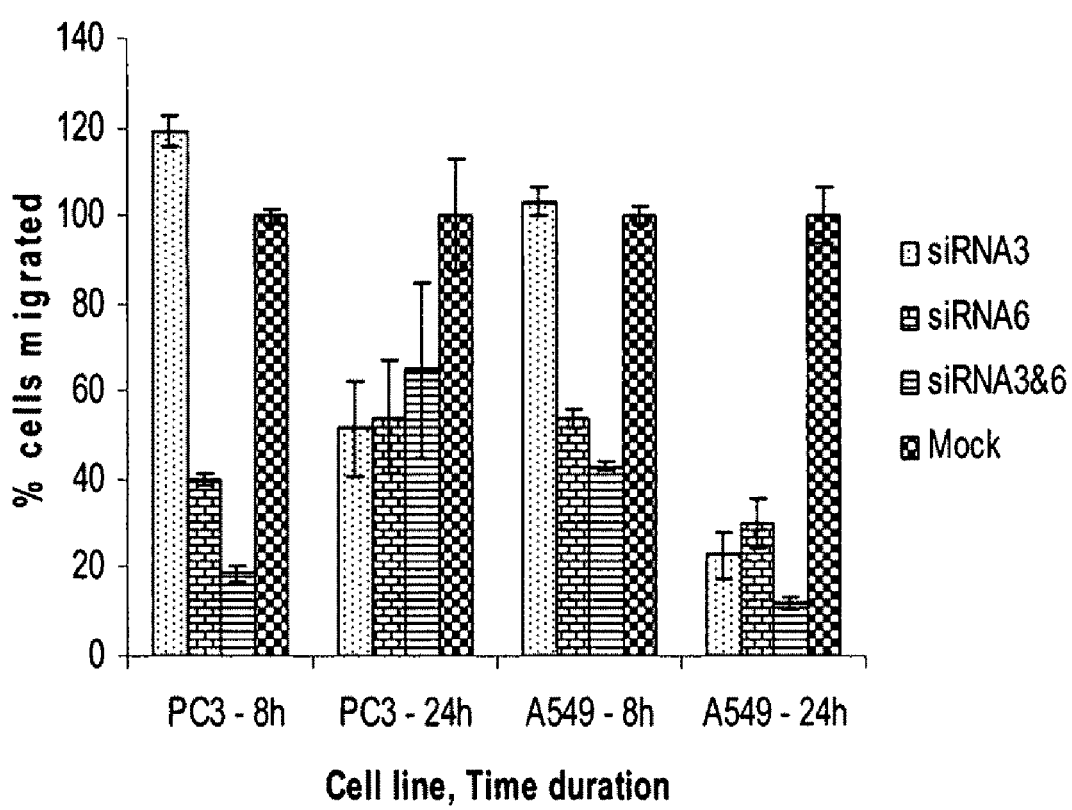

FIG. 13: Effect of siRNA on cell migration as determined by scratch assay.

Figure 14:
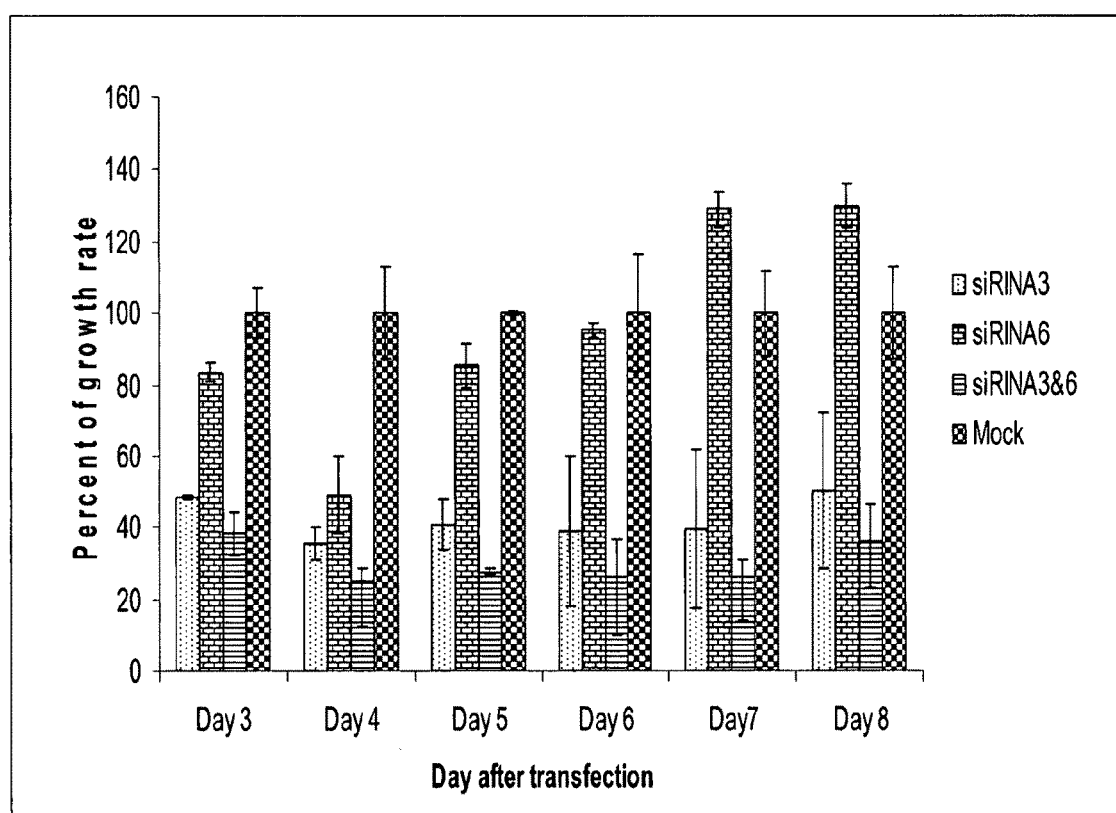

FIG. 14. Growth rate of epidermoid carcinoma cell line A431 over a period of 8 days from the date of transfection (with siRNA 3, 6 or 3 & 6), as determined by MTS.

Figure 15:
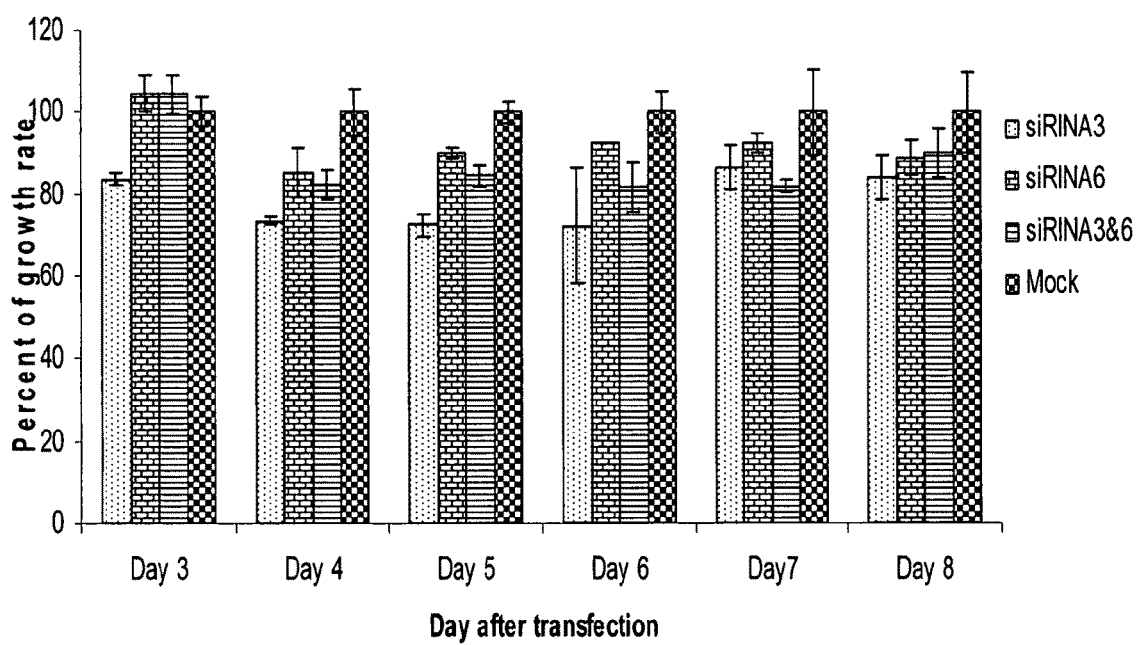

FIG. 15. Prostate cancer cell line PC3 growth rate over a period of 8 days from the date of transfection (with siRNA 3, 6 or 3 & 6) was compared with that of mock treated cells, as determined by MTS assay.

Figure 16:
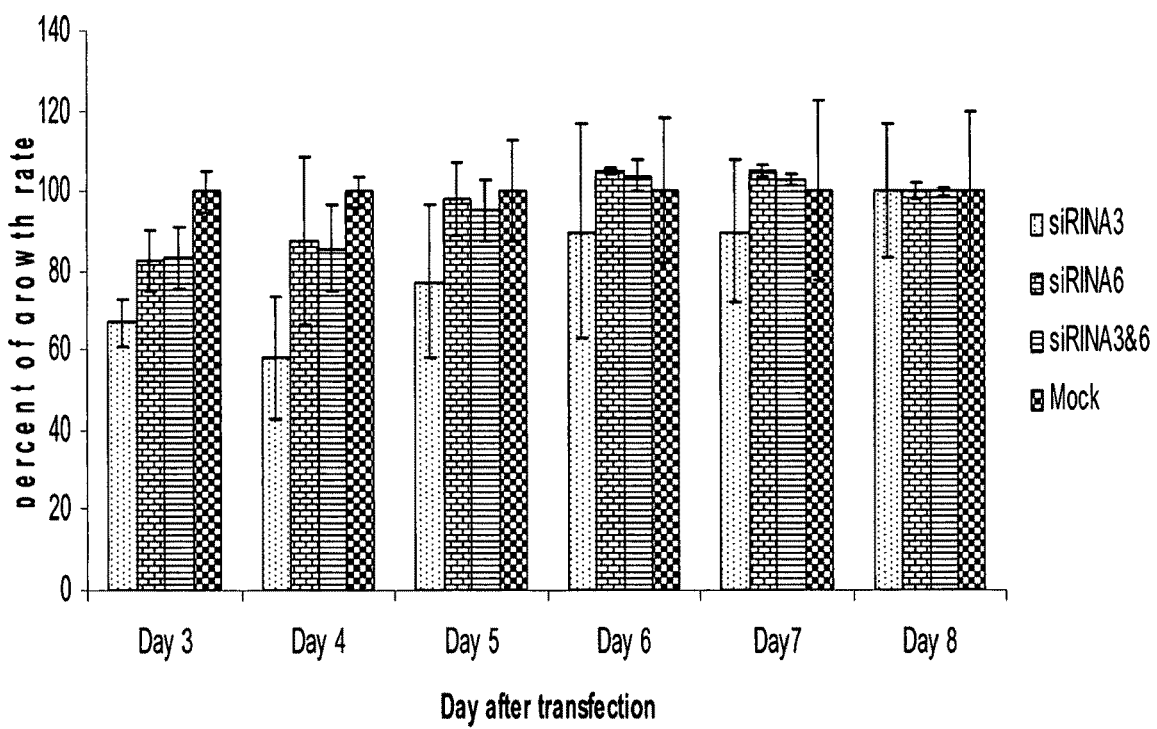

FIG. 16. Non-small cell lung cancer cell line A549 growth rate over a period of 8 days from the date of transfection (with siRNA 3, 6 or 3 & 6) compared with that of mock treated cells, as determined by MTS assay.

Figure 17:
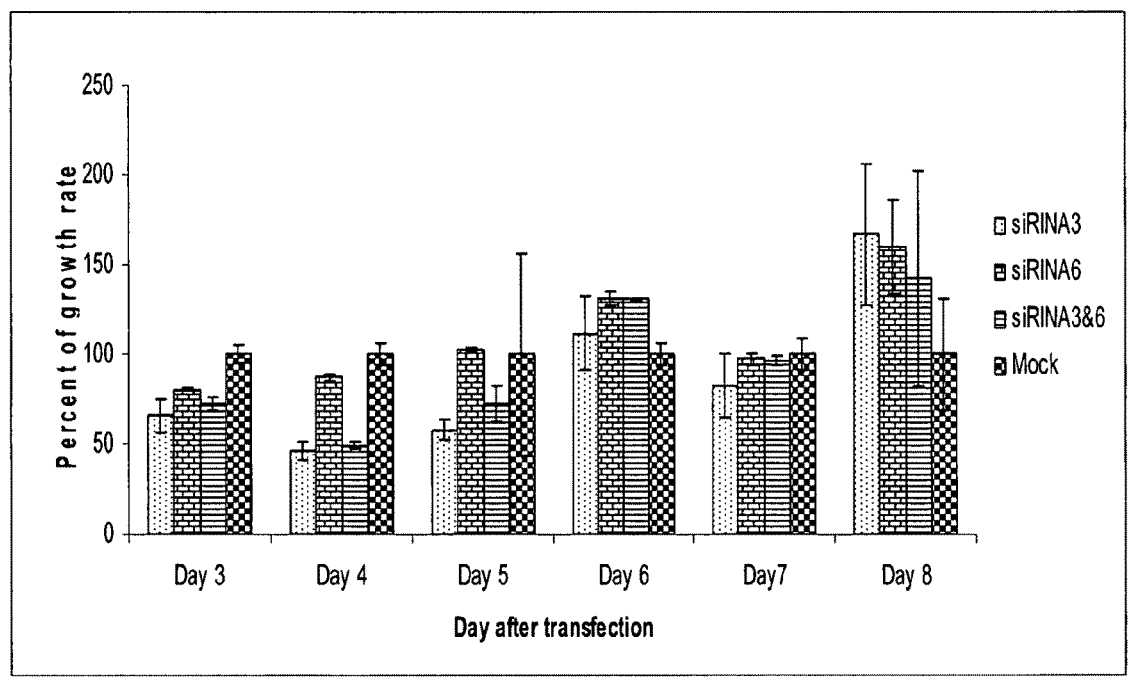

FIG. 17. Normal diploid retinal pigmented epithelial cells ARPE-19 growth rate over a period of 8 days from the date of transfection was compared with that of mock treated cells, as determined by MTS assay.

Figure 18:
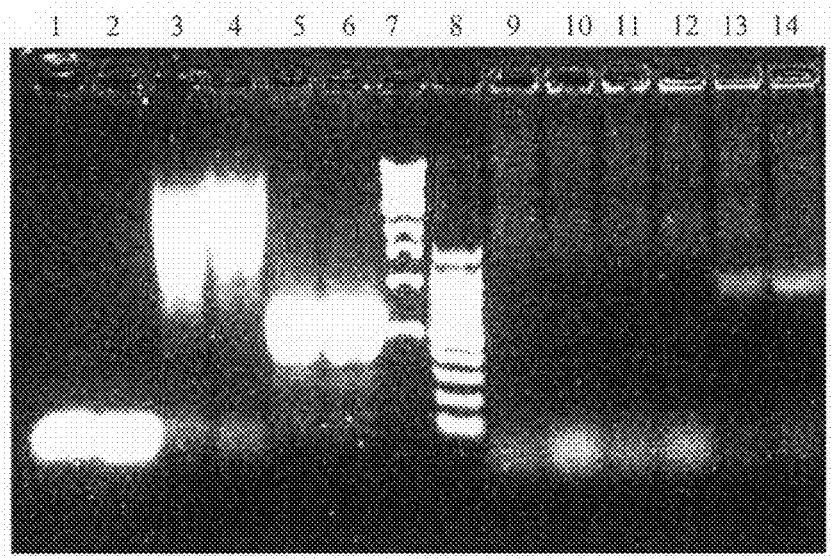

FIG. 18. Serum stability of siRNA 3 after 48 h of incubation at 37° C. was derived by resolving serum-siRNA mixture over a 2.5% agarose gel electrophoresis followed by ethidium bromide staining of the gel. siRNA 3 alone, siRNA 3 conjugated with 3'-cholesterol at antisense strand and siRNA 3 conjugated with 3'-cholesterol on sense strand.

Lane 1 & 9. siRNA 3 alone at 0 and 48 h respectively.

Lane 2 & 10. siRNA 3 complexed with Hiperfect transfection agent at 0 and 48 h respectively.

Lane 3 & 11. siRNA 3 antisense strand with cholesterol at 0 and 48 h respectively.

Lane 4 & 12. siRNA 3 antisense strand with cholesterol and complexed with Hiperfect transfection agent at 0 and 48 h respectively.

Lane 5 & 13. siRNA 3 sense strand with cholesterol at 0 and 48 h respectively.

Lane 6 & 14. siRNA 3 sense strand with cholesterol and complexed with Hiperfect transfection agent at 0 and 48 h respectively. Arrowhead indicates siRNA 3 remained even after incubation with 100% serum at 37° C. for 48 h.

Figure 19:
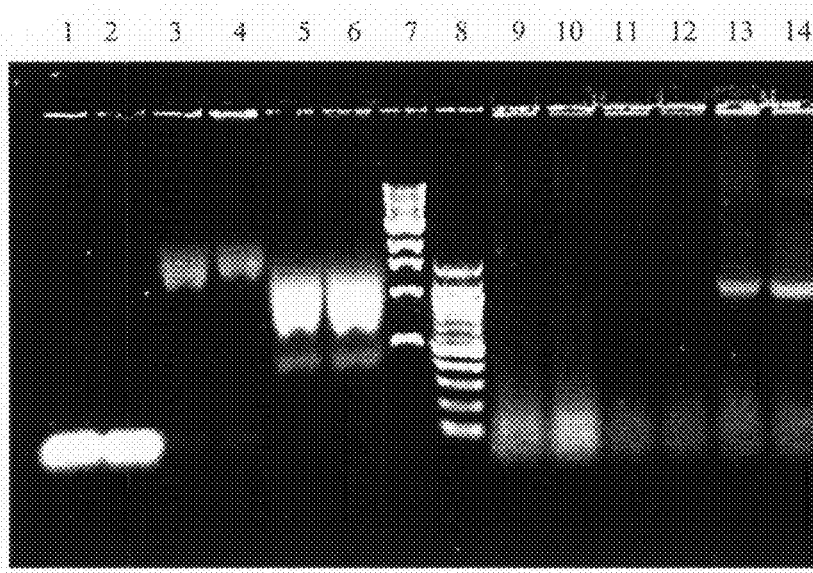

FIG. 19. Serum stability of siRNA 6 after 48 h of incubation at 37° C. was derived by resolving serum-siRNA mixture over a 2.5% agarose gel electrophoresis followed by ethidium bromide staining of the gel. siRNA 6 alone, siRNA 6 conjugated with 3'-cholesterol at antisense strand and siRNA 6 conjugated with 3'-cholesterol on sense strand.

Lane 1 & 9. siRNA 6 alone at 0 and 48 h respectively.

Lane 2 & 10. siRNA 6 complexed with Hiperfect transfection agent at 0 and 48 h respectively.

Lane 3 & 11. siRNA 6 antisense strand with cholesterol at 0 and 48 h respectively.

Lane 4 & 12. siRNA 6 antisense strand with cholesterol and complexed with Hiperfect transfection agent at 0 and 48 h respectively.

Lane 5 & 13. siRNA 6 sense strand with cholesterol at 0 and 48 h respectively.

Lane 6 & 14. siRNA 6 sense strand with cholesterol and complexed with Hiperfect transfection agent at 0 and 48 h respectively. Arrowhead indicates siRNA 6 remained even after incubation with 100% serum at 37° C. for 48 h.

Figure 20:
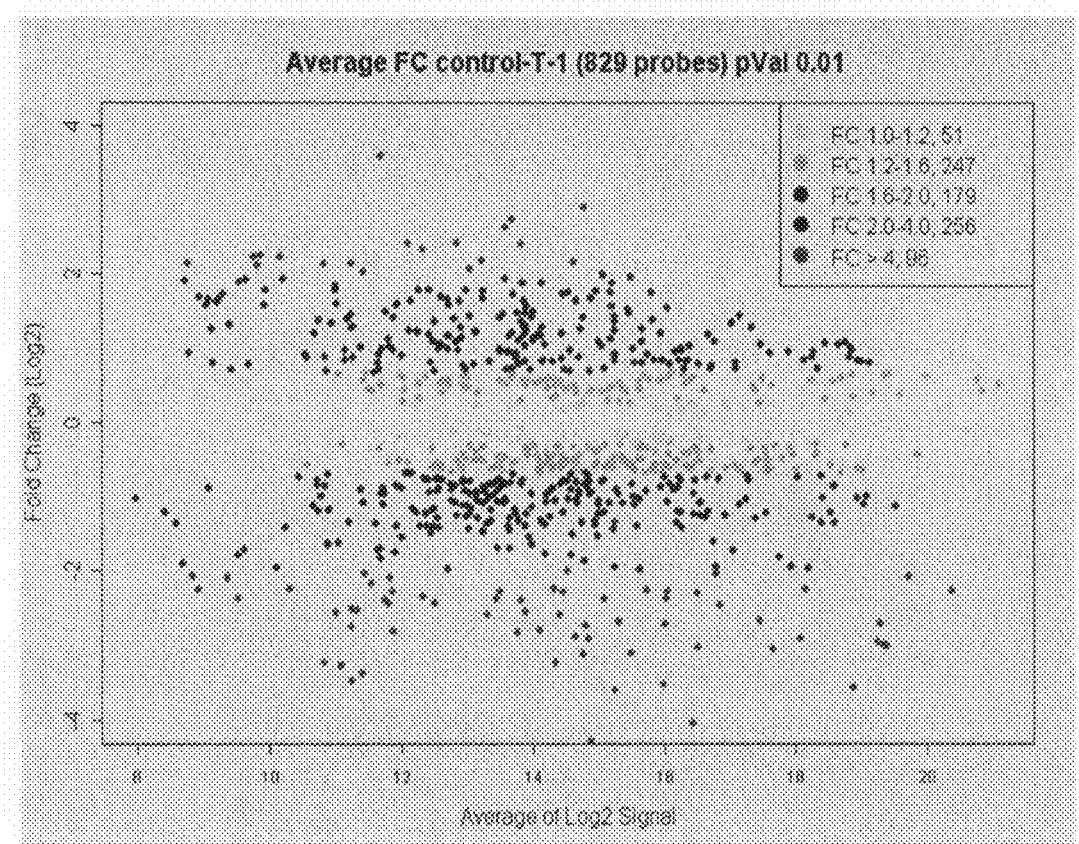

FIG. 20. Effect of repression of AurkB by siRNA 3 in prostate cancer cells PC3 by microarray analysis. Microarray analysis has identified a total of 829 genes either upregulated or down regulated as depicted in the figure.

Figure 21:
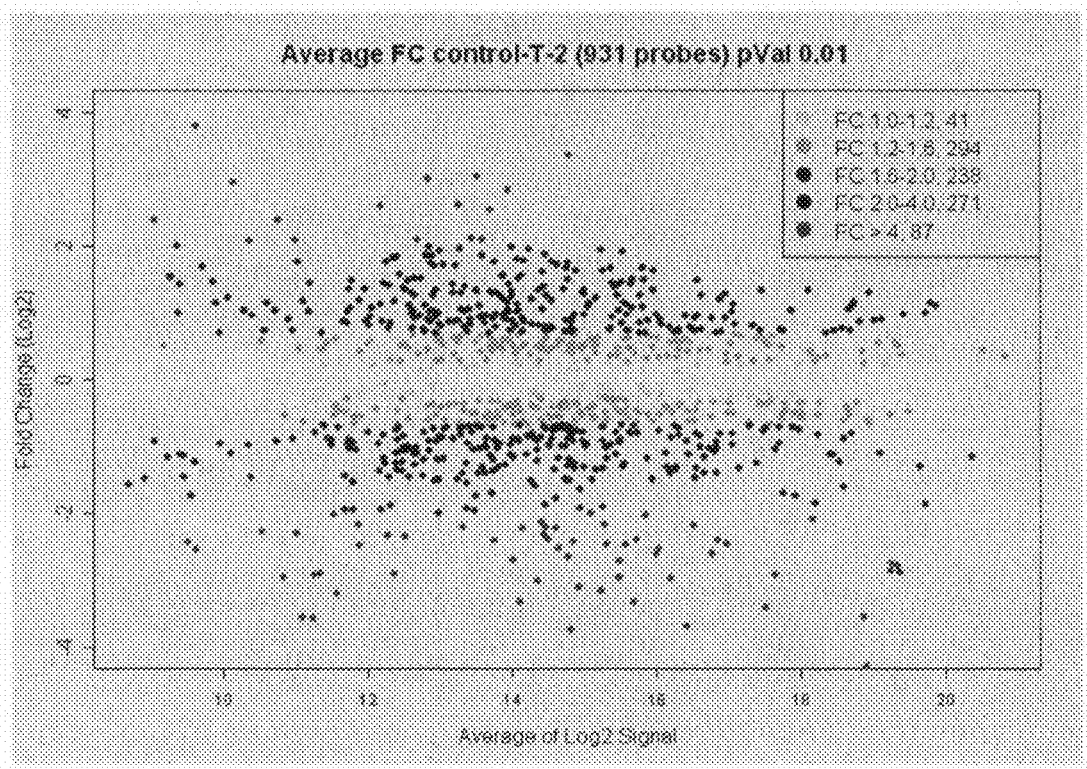

FIG. 21. Effect of repression of EGFR by siRNA 6 in prostate cancer cells PC3 by microarray analysis. Microarray analysis has identified a total of 931 genes either upregulated or down regulated as depicted in the figure.

Figure 22:
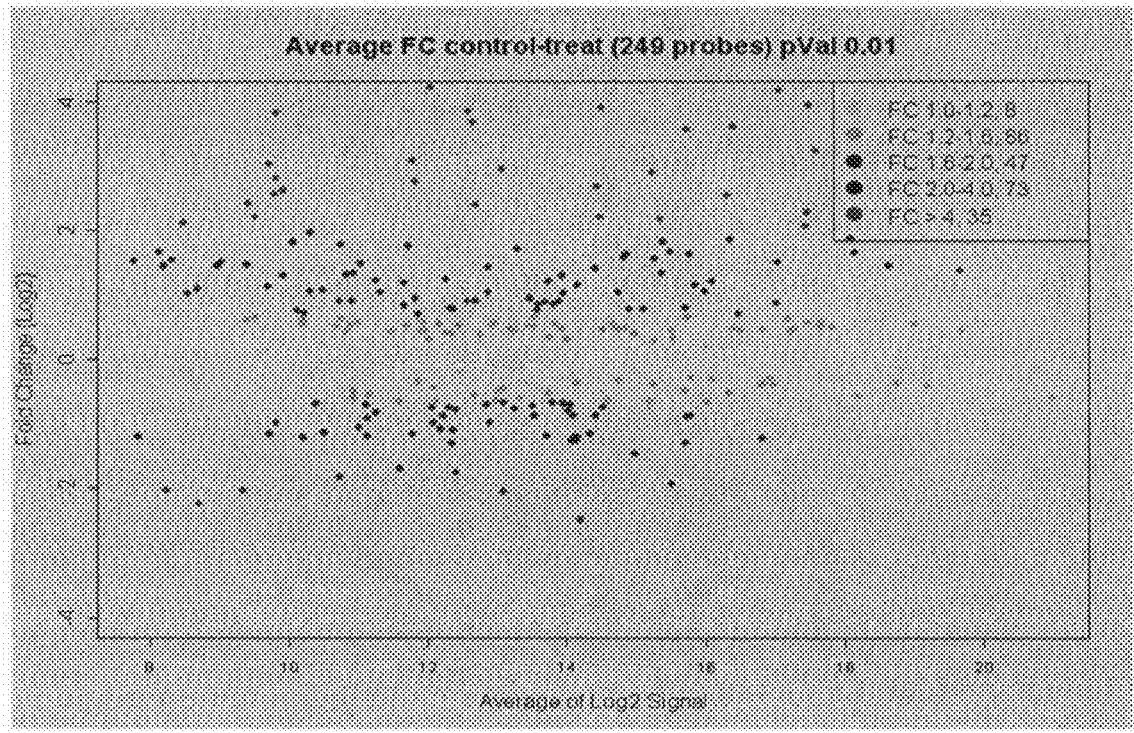

FIG. 22. Effect of simultaneous repression of AurkB and EGFR by siRNA 3 and 6 in prostate cancer cells PC3 by microarray analysis. Microarray analysis has identified a total of 249 genes either upregulated or down regulated as depicted in the figure.

Figure 23:
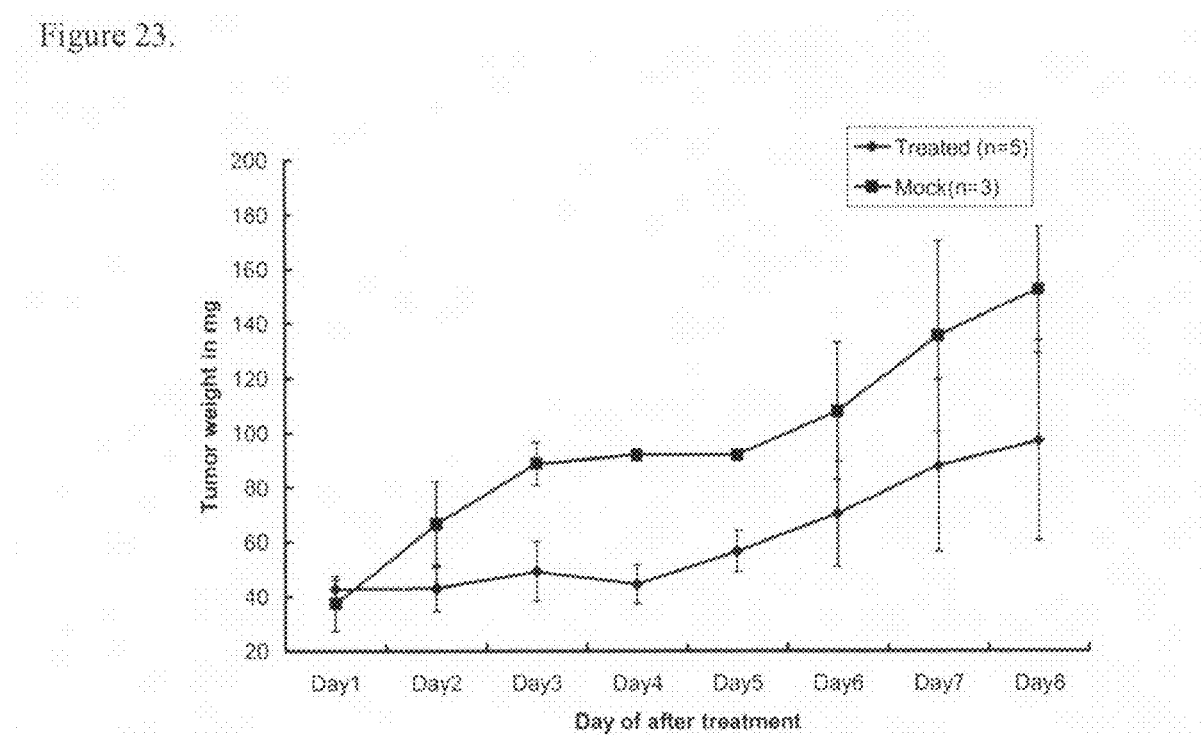

FIG. 23. Xenografted prostate cancer male SCID mice treated with combination of siRNA3 and 6 by intratumoral delivery.

Figure 24:
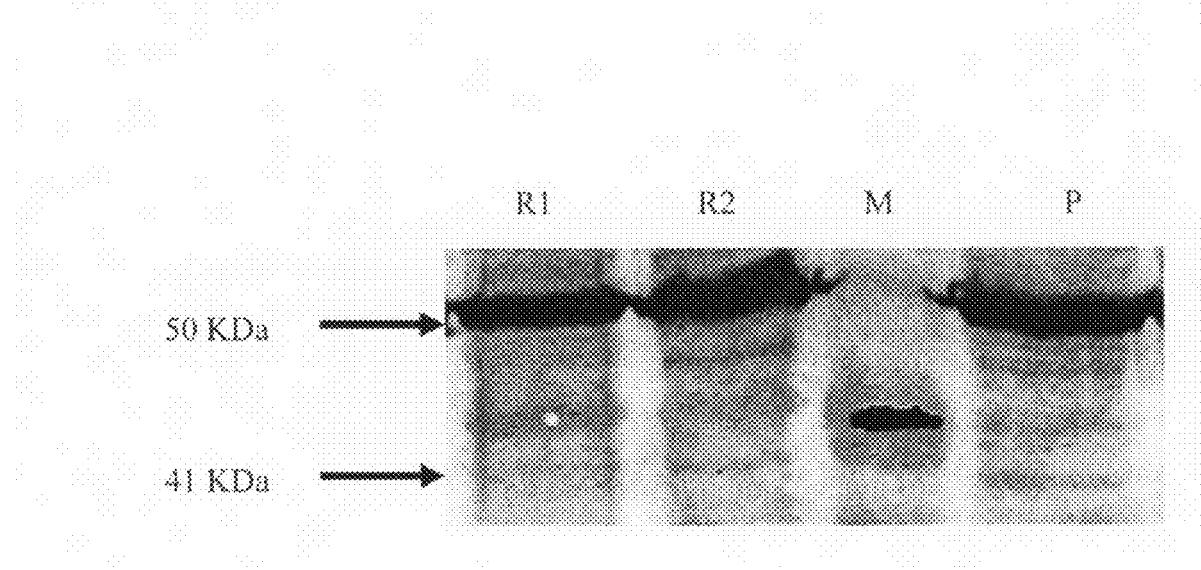

FIG. 24. Western blot of tumors. R1 represents animal 1 treated with siRNA 3 and 6 combination while R2 represents animal number 2 treated with siRNA 3. P represents placebo treated animal. M represents molecular weight markers. Arrowheads indicates 41 KDa AurkB and 50 KDa tubulin.

Figure 25:
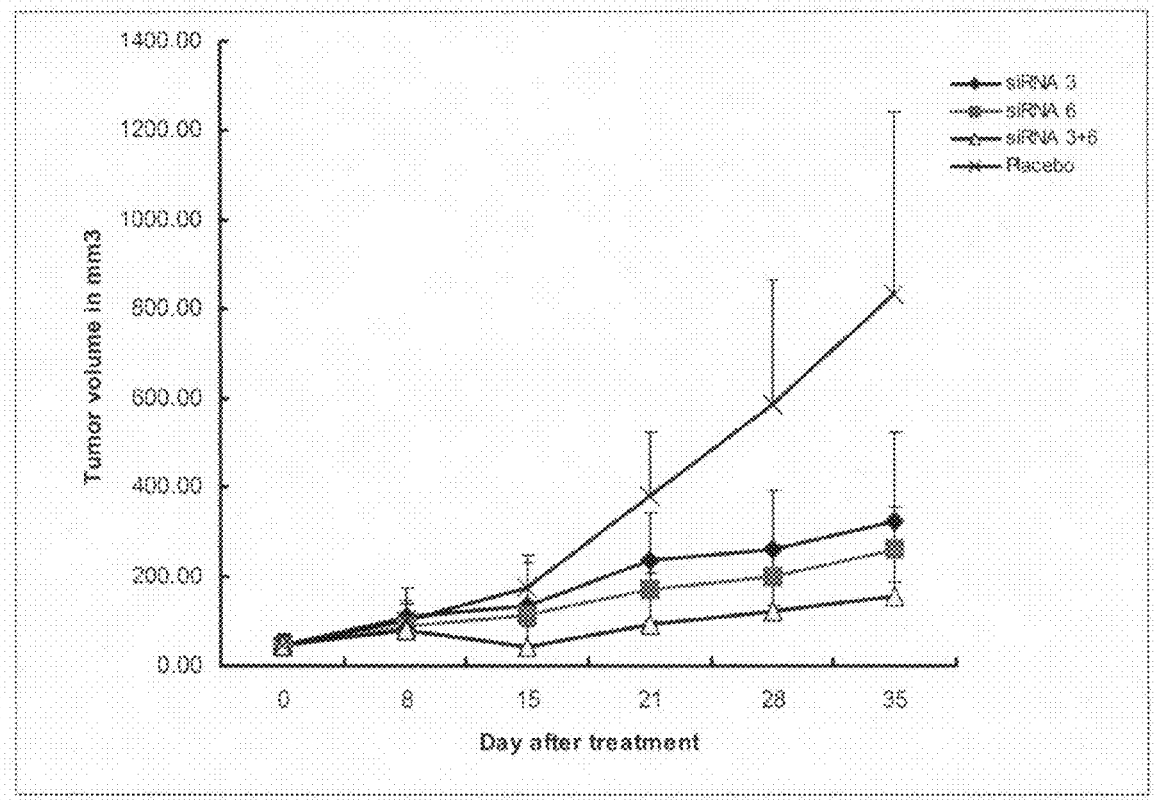

FIG. 25. Tumor volume from prostate cancer xenografted male athymic nude mice treated with siRNA 3 (Group A, n=6), siRNA 6 (Group B, n=6) siRNA 3 and 6 combination (Group C, n=5) and Placebo (Group D, n=7). In the figure mean tumor volumes were represented along with their standard deviations. All data represented was statistically validated by determining F factor using homology of variance, followed by two pair t-test where P≦0.05. Bars represent S.E. of the mean.

Figure 26:
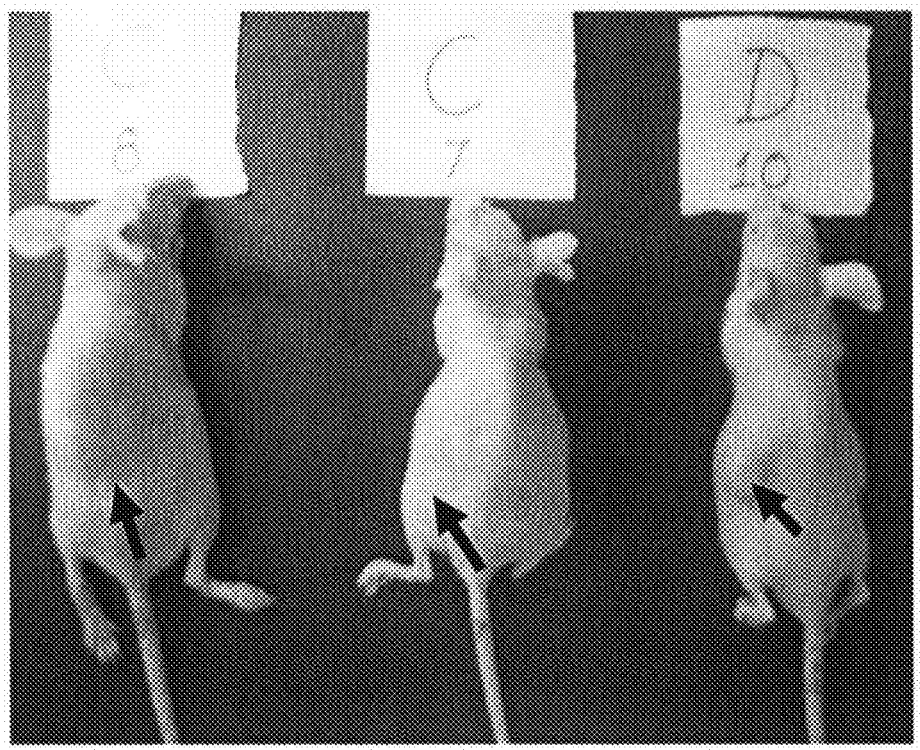

FIG. 26. Prostate cancer xenografted male athymic nude mice treated with a combination of siRNA 3 and siRNA 6 (Group C) and Placebo (Group D). Arrowheads indicate the complete regression of prostate tumors after 35 days of treatment initiation in animals C8 and C7, while placebo-treated animal D10 was showing presence of xenografted tumor.

Figure 27:
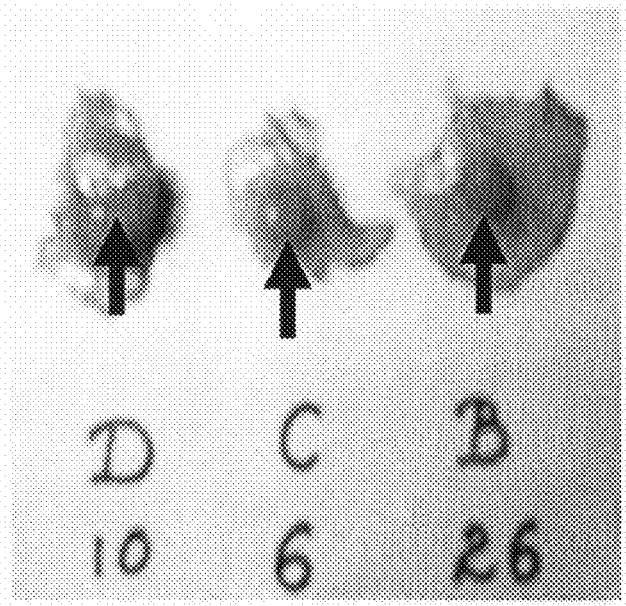

FIG. 27. Prostate cancer xenografted male athymic nude mice treated with siRNA 6 (Group B, Animal 26), siRNA 3 and 6 combination (Group C, Animal 6) and Placebo (Group D, Animal 10) were retrieved after 35 days treatment. Arrowheads represent tumor tissues retrieved.

Figure 28:
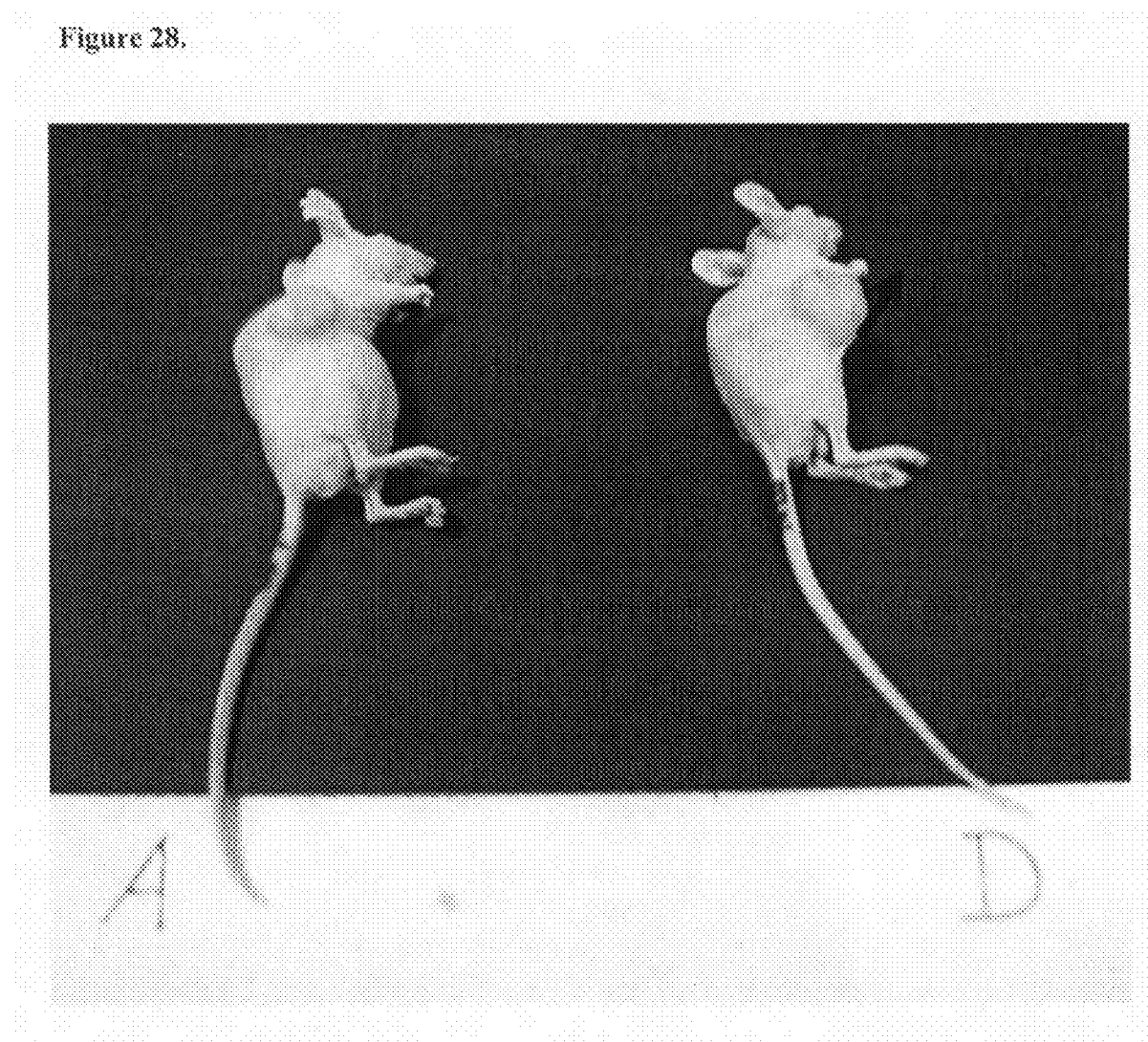

FIG. 28. Prostate cancer xenografted male athymic nude mice treated with siRNA 3 (Group A) and Placebo (Group D). Arrowheads indicate the vascularization of the prostate tumor after 35 days of treatment initiation.

Figure 29:
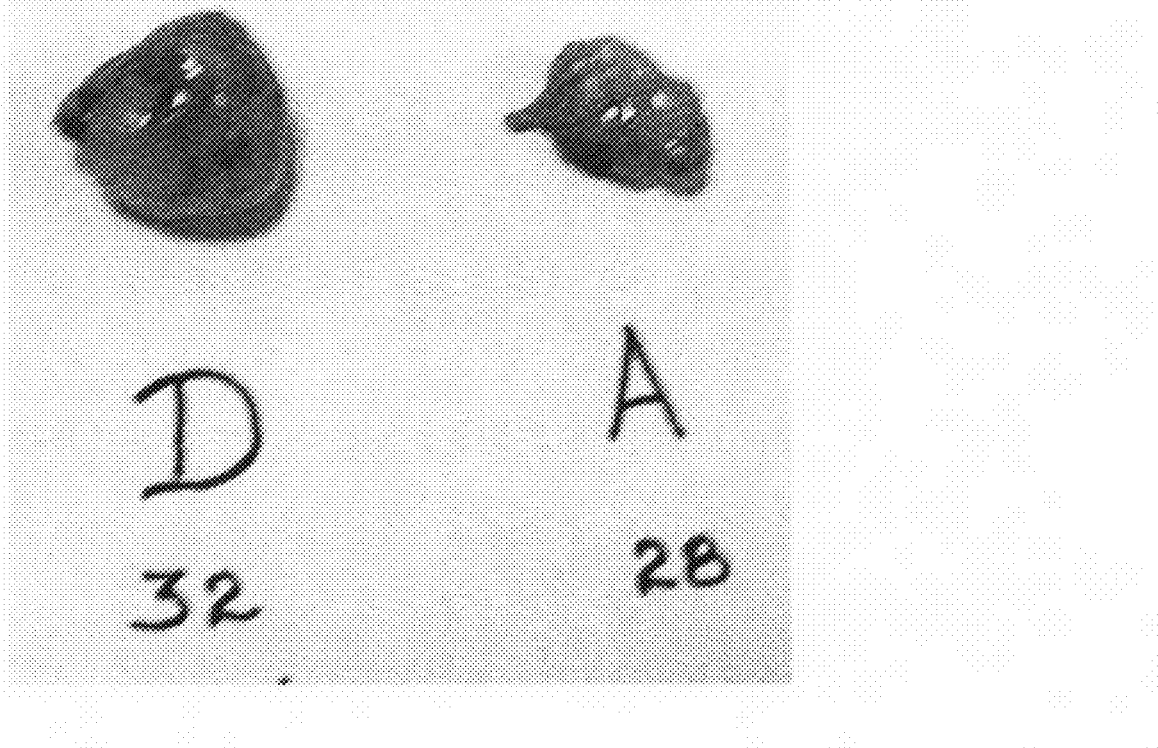

FIG. 29. Prostate cancer xenografted male athymic nude mice treated with siRNA 3 and Placebo. At the end of 35 days of treatment tumors were retrieved and compared for gross pathology. "D" represents placebo treated animal 32. "A" represents siRNA 3 treated animal number 28.

Figure 30:
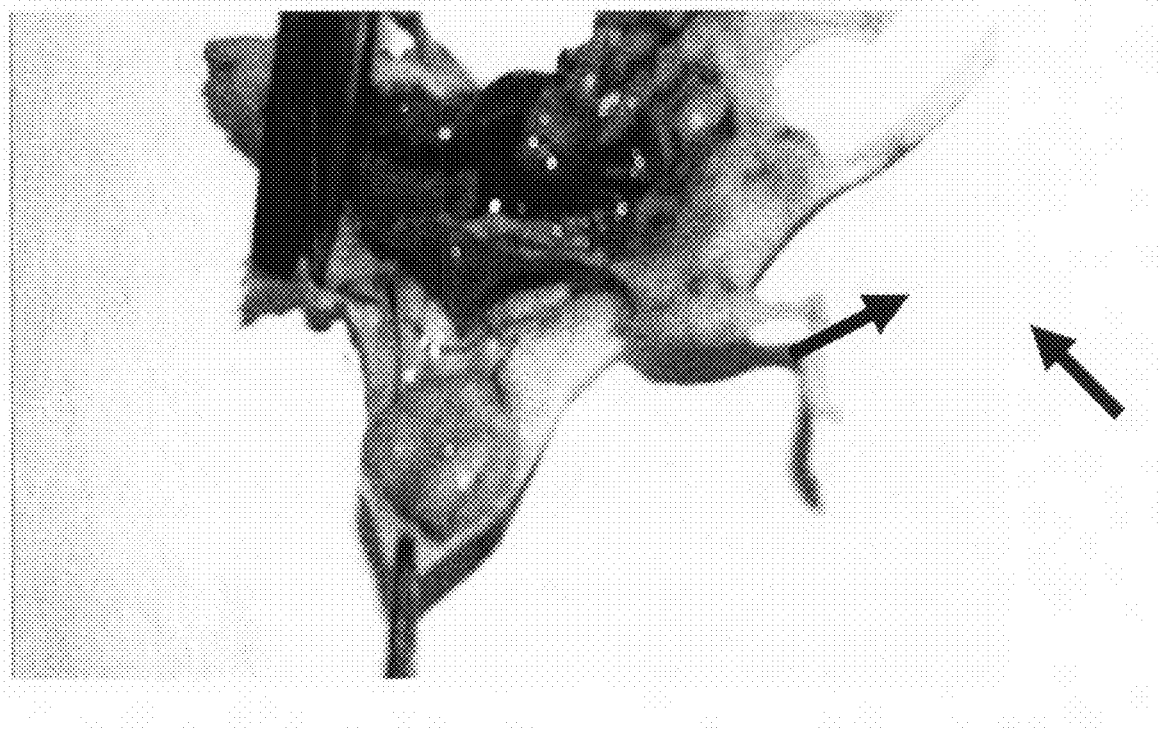

FIG. 30. Prostate cancer xenografted male athymic nude mice treated with placebo. Arrowheads indicate the vascularization of the prostate tumor after 35 days of treatment initiation.

Figure 31:
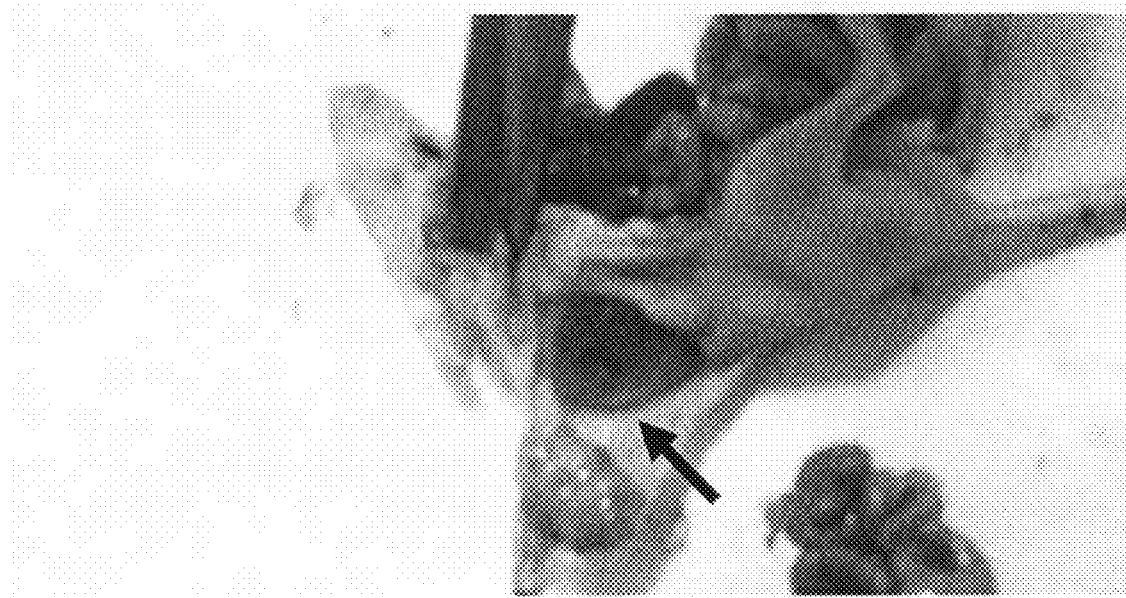

FIG. 31. Prostate cancer xenografted male athymic nude mice treated with siRNA 3. Arrowhead indicates absence of vascularization of the prostate tumor after 35 days of treatment initiation.

Figure 32:
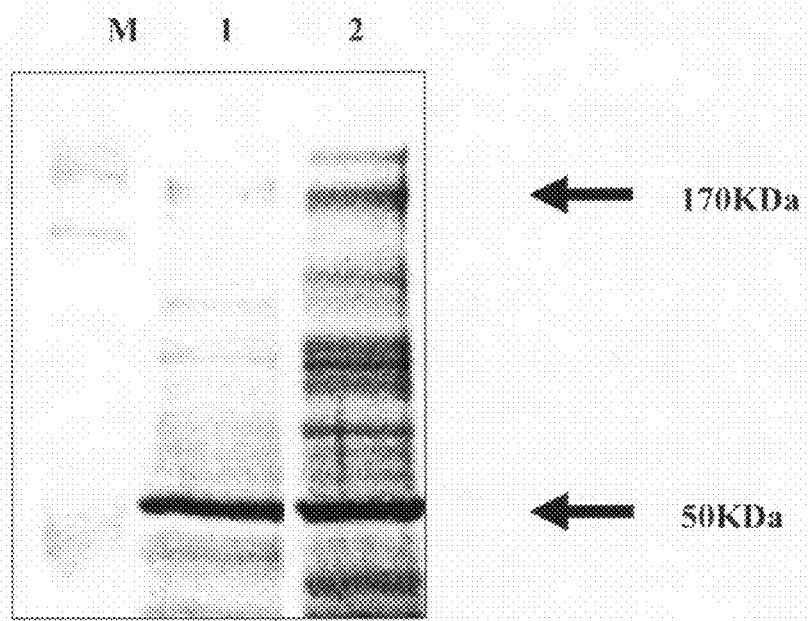

FIG. 32: Western blot of EGFR expression (170 kDa) in breast cancer cell line SKBR3, 72 h after transfection with siRNA 6 (Lane 1) or mock (Lane 2). Endogenous control tubulin (50 kDa). Lane M: Rainbow high molecular weight markers.

Figure 33:
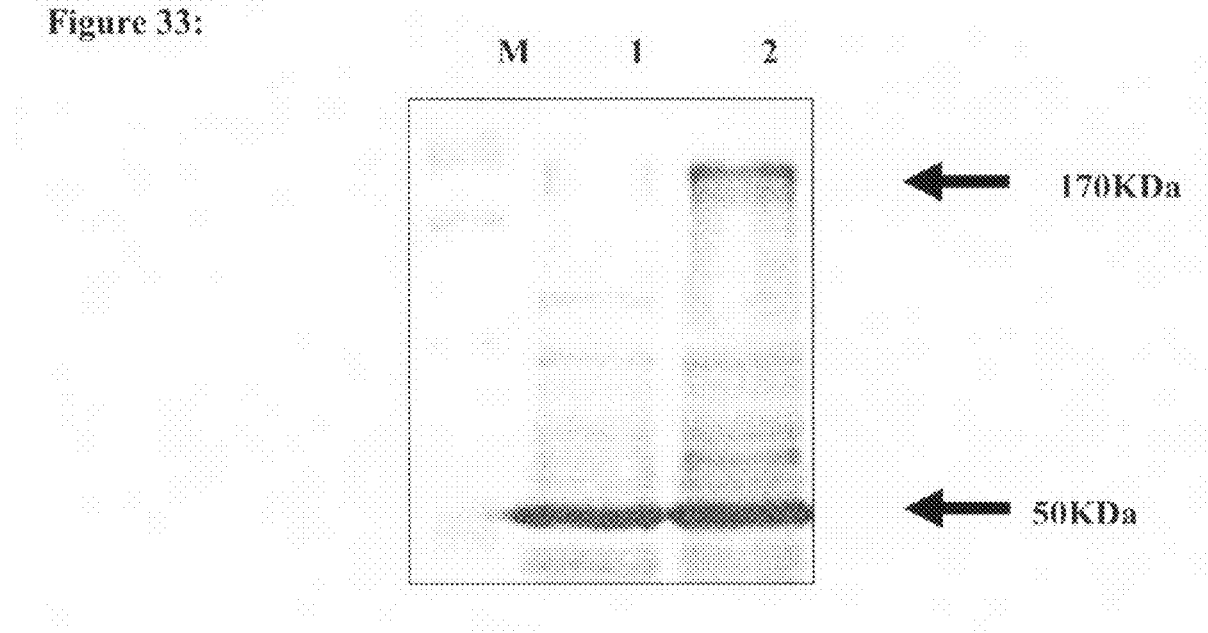

FIG. 33: Western blot of EGFR expression (170 kDa) in breast cancer cell line MCF-7, 72 h after transfection with siRNA 6 (Lane 1) or mock (Lane 2). Endogenous control tubulin (50 kDa). Lane M: Rainbow high molecular weight markers.

Figure 34:
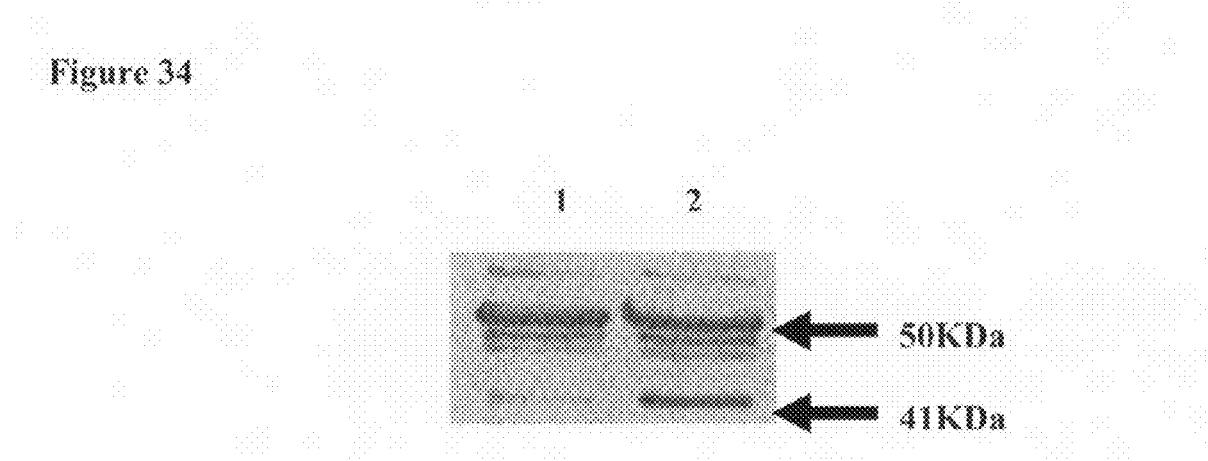

FIG. 34. Western blot of AurkB expression in breast cancer cell line MCF-7, 72 h after transfection with siRNA 3 (Lane 1) or mock (Lane 2).

Figure 35:
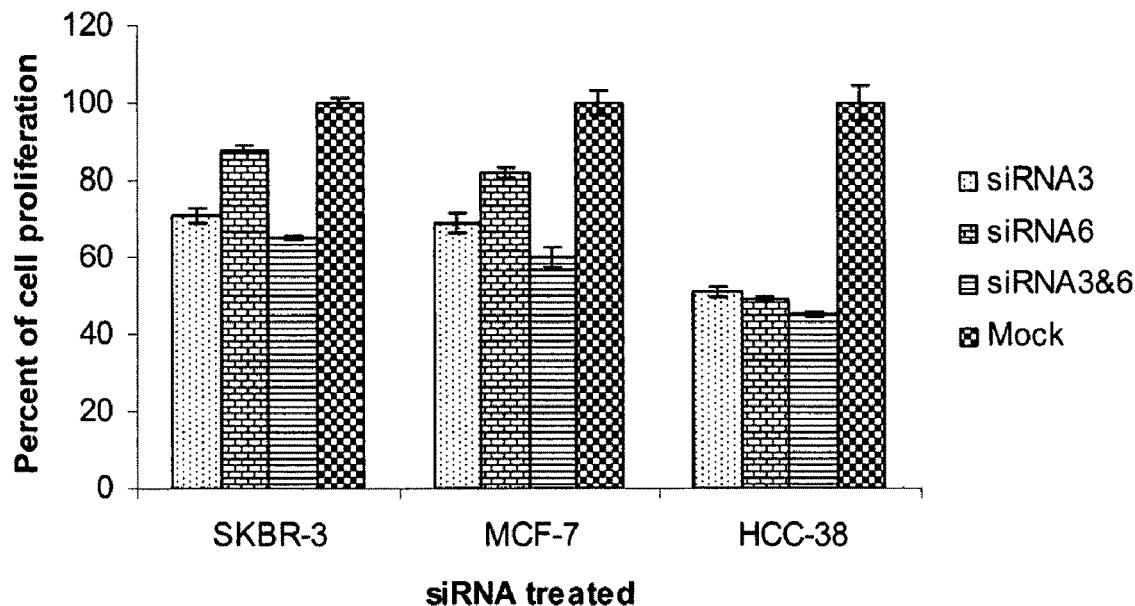

FIG. 35. Metabolic activity, determined by MTS assay, of breast cancer cell lines SKBR-3, MCF-7 and HCC-38 treated with siRNA 3 (10 nM), siRNA 6 (10 nM), combination of siRNA 3 and 6 at 10 nM each concentration. 10 nM of siRNA7 was provided as mock control. Statistical significance was determined between mock treated cells vs siRNA transfected cells by paired two tail t-test where P≦0.05.

Figure 36:
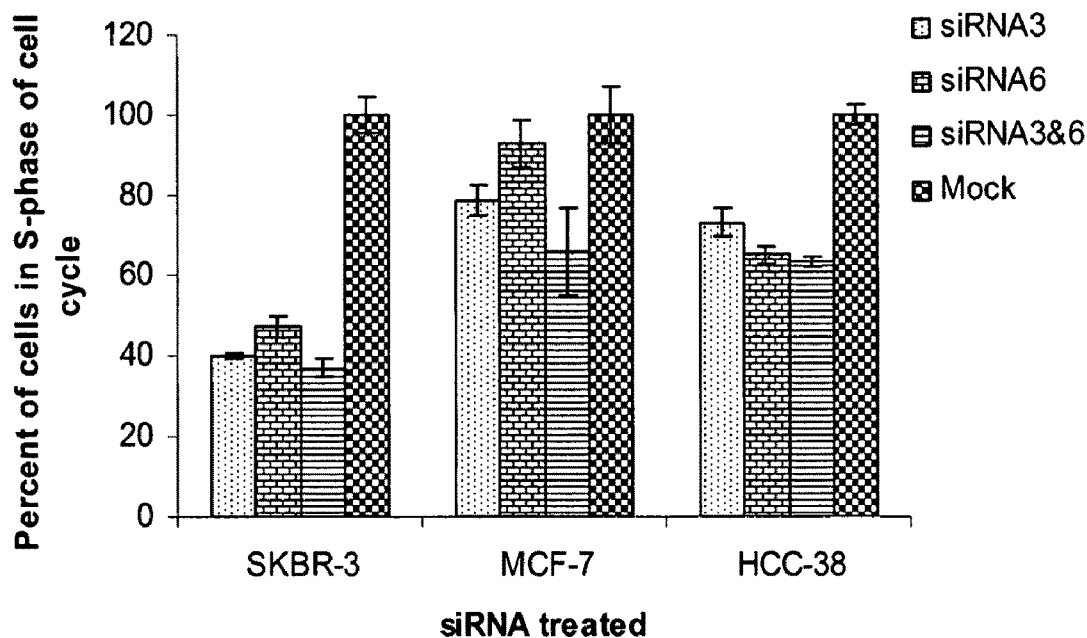

FIG. 36. BrdU incorporation into breast cancer cell lines (SKBR-3, MCF-7 and HCC-38) treated with siRNA (3, 6 or combination of 3 & 6). 10 nM of siRNA7 was provided as mock control.

Figure 37:
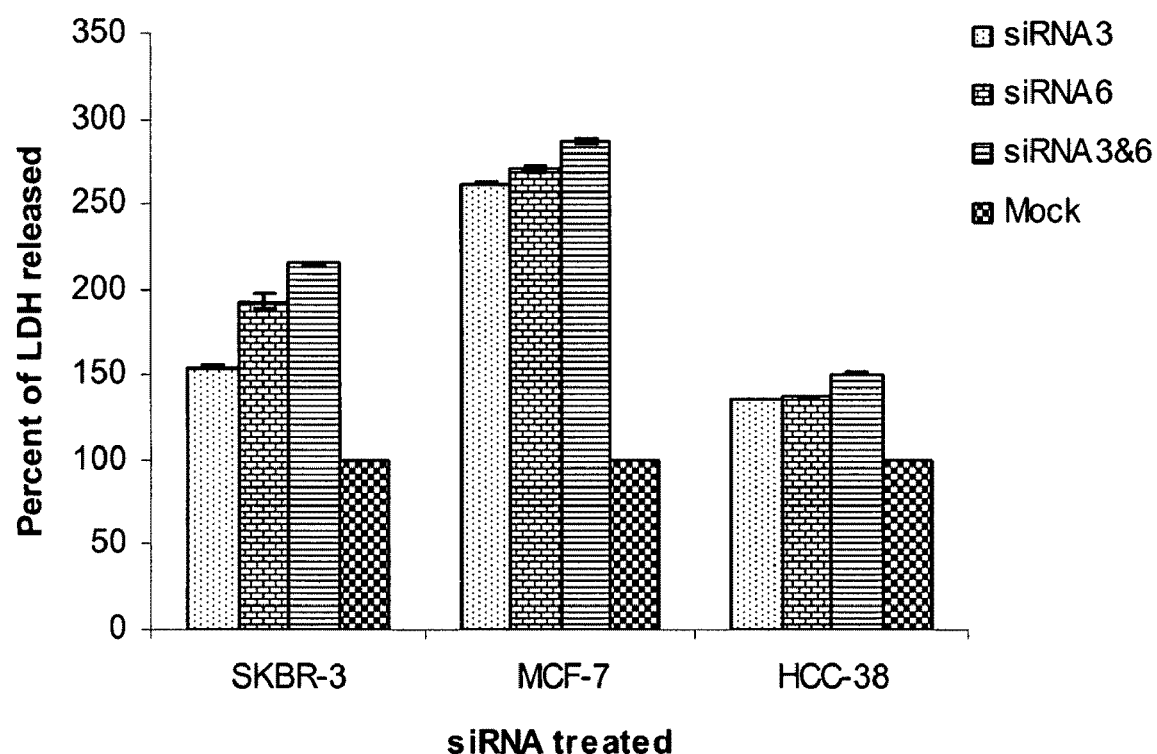

FIG. 37. LDH release by breast cancer cells treated with siRNA3 and/or siRNA6, against mock treatment. 10 nM of siRNA7 was provided as mock control.

Figure 38:
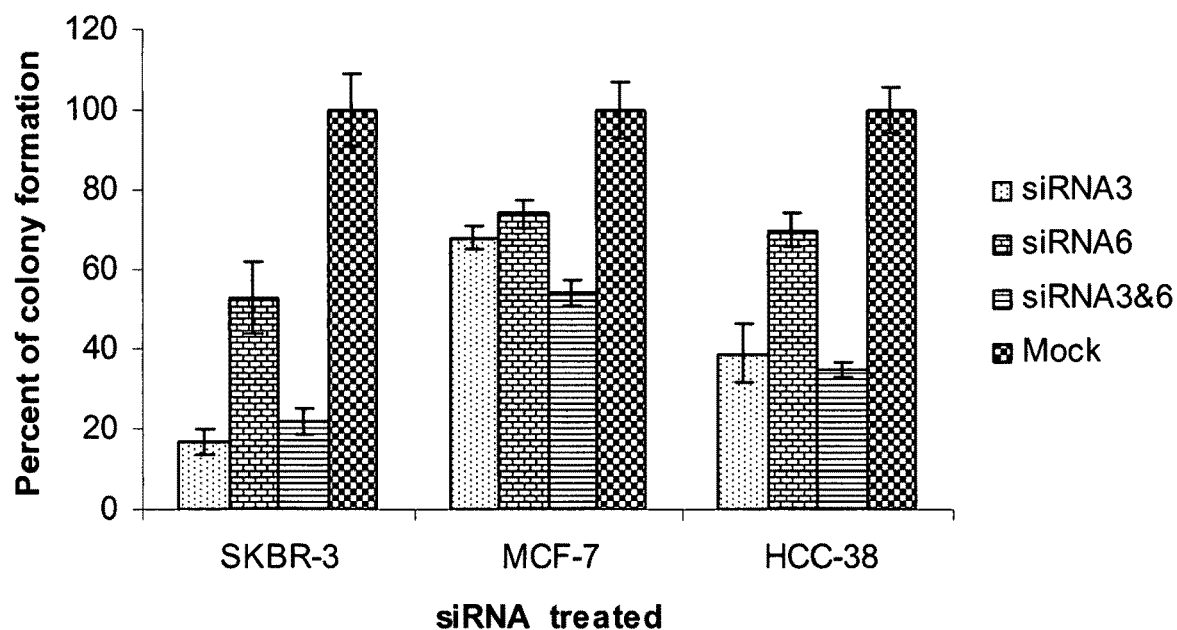

FIG. 38. Colony forming efficiency of breast cancer cell lines treated with siRNA 3 (10 nM), siRNA 6 (10 nM) or a combination of siRNA 3 and 6 at 10 nM concentration, against mock. 10 nM of siRNA7 was provided as mock control.

FIG. 39. Cell cycle analysis of HeLa cervical cancer cells transfected with siRNA 3 (for AurkB) or mock siRNA 7. A: siRNA 3 (for AurkB) transfected cells—77% were in G2 phase, 6% were in S phase and 16% were in G1 phase. B: mock siRNA 7 transfected cells—17% were in G2 phase, 36% were in S phase and 46% were in G1 phase.

Figure 40:
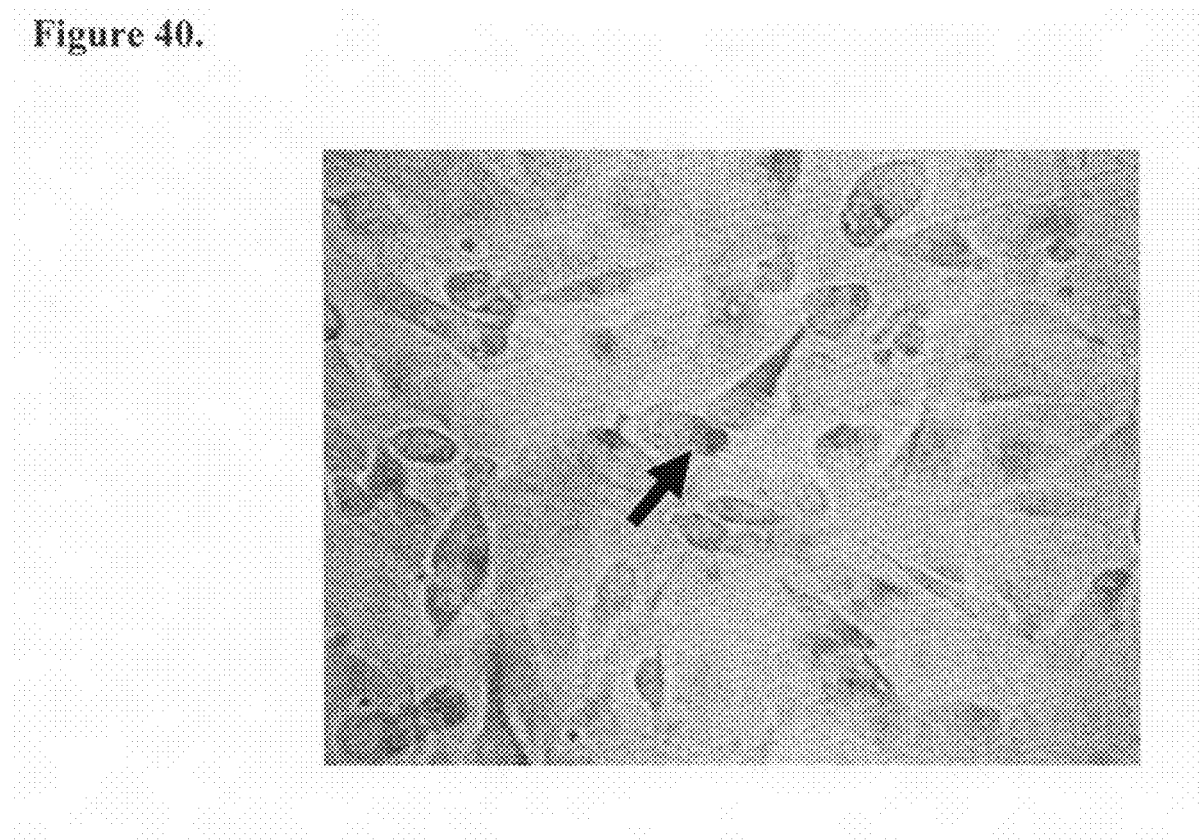

FIG. 40. HeLa cervical cancer cells were transfected with siRNA 3 and 6 simultaneously and stained for senescence induction 72 h after transfection. Detection of β-glycosidase activity in cells (via staining) corresponded to activation of the senescence pathway. The arrowhead points to one example of a cell blue in color, indicating β-glycosidase activity. Images present 200× magnification.

DETAILED DESCRIPTION OF THE INVENTION

Definitions

The term "short nucleic acid molecule" refers to any nucleic acid molecule capable of modulating gene expression. The terms "short interfering nucleic acid", "siNA" or "siNA molecules, "short interfering nucleic acid molecule", "short interfering oligonucleotide molecule" refer to any nucleic acid molecule capable of inhibiting or down-regulating gene expression.

Typically, short interfering nucleic acid molecules are composed primarily of RNA, and may be referred to as "short interfering RNA" or "siRNA." A siNA may, however, include nucleotides other than RNA, such as in DNAi (interfering DNA), or other modified bases. Thus, the term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA such as analogs or analogs of naturally occurring RNA.

The term "modulate" or "modulates" means that the expression of the gene or level of RNA molecule or equivalent RNA molecules encoding one or more protein or protein subunits or peptides, or activity of one or more protein subunits or peptides is up regulated or down regulated such that the expression, level, or activity is greater than or less than that observed in the absence of the modulator. The term "modulate" includes "inhibit"

The term "mock treated" refers to samples to which is applied siRNA 7 and 8, which are scrambled siRNAs for the gene AurkB, and EGFR respectively. Because of the scrambling of the sequence, these siRNA do not target any gene of interest. Mock treatment is the standard negative control herein.

The term "gene" as used herein means a nucleic acid that encodes a RNA sequence including but not limited to structural genes encoding a polypeptide.

The term "AurkB" as used herein refers to any AurkB protein, peptide, or polypeptide having Aurorakinase or AurkB family activity such as encoded by genbank accession number NM_004217: It also refers to any nucleic acid sequence encoding AurkB protein, peptide, or polypeptide having isoforms, mutant genes, splice variants and polymorphisms.

The term "target nucleic acid" as used herein means any nucleic acid sequence whose expression or activity is to be modulated. The target nucleic acid can be DNA or RNA.

The term "sense region" as used herein means a nucleotide sequence of a small nucleic acid molecule having complementary to a target nucleic acid sequence. In addition, the sense region of a small nucleic acid molecule can comprise a nucleic acid sequence having homology with a target nucleic acid sequence.

The term "antisense region" as used herein means a nucleotide sequence of a small nucleic acid molecule having a complementarity to a target nucleic acid sequence. It can also comprise a nucleic acid sequence having complementarity to a sense region of the small nucleic acid molecule.

The term "complementarity" or "complementary" as used herein means that a nucleic acid can form hydrogen bonds with another nucleic acid molecule.

The term "cancer" or "proliferative disease" as used herein means any disease, condition, trait, genotype or phenotype characterized by unregulated cell growth or replication as is known in the art. It can include all types of cancer, tumors, lymphomas, carcinomas that can respond to the modulation of disease-related AurkB gene expression in a cell or tissue alone or in combination with other therapies.

siNA Design and Testing

In one embodiment, the present invention provides short interfering nucleic acid (siNA) molecules and their uses in modulation of AurkB gene expression. The main features of the studies conducted are as follows:

1. Design of siNA.

2. Preparation of siNA

3. Efficacy testing of the compounds

4. Comparative data of siRNA having 21, 22, and 27 nucleotides

5. Potency evaluation in animal models

The design of suitable siNA involved the design of the siRNA with 21, 23, and 27 nucleotides for modulation of AurkB, without chemical modification. The AurkB and EGFR target genes were screened for accessible sites and siRNA was synthesized considering the open reading frame (ORF) sequences of AurkB and EGFR. The following general requirements were considered in siNA design:

i. No runs of four or more A, T, G, or U in a row ii. The following sequences were avoided, as they can induce an interferon response. A) 5'-UGUGU-3' and B) 5'-GUC-CUUCAA-3' iii. The first 200 bases were omitted from the start codon to avoid binding to regulatory element.

iv. Each siNA duplex was checked in silico to avoid silencing of off-target effects made on BLAST search considering the following parameters:

A. Low complexity filtering was removed to avoid insignificance by BLAST resulting in limited or no query sequencer.

B. The word size was set to 7 letters, the minimal value algorithm

C. Expected value threshold was set at 1000 to avoid the probability of short sequence occurrence.

Further the target genes such as AurkB and EGFR were screened for accessible sites and siNA were synthesized considering the ORF sequences of AurkB and EGFR siNA synthesis was done by commercially available methods (e.g., Qiagen) using chemically-protected phosphoramidite monomers. Resultant oligomers were purified by PAGE, desalting, or IE-HPLC. The quality of each siNA was analyzed by MALDI-TOF and yields were determined by an integrated spectrophotometer.

Efficacy testing of the molecules were done in different cell lines. The following cell lines were obtained from ATCC and cultured as per ATCC recommendations: PC3 (prostate cancer); HeLa (cervical cancer) and SCC-4 (oral cancer); A549 (non-small lung cancer); A431 (skin cancer); SKBR-3, MCF-7 and HCC-38 (breast cancer); HFF-2 (normal diploid fibroblasts); and ARPE-19 (normal diploid retinal pigmented epithelial cells)

Confluent monolayers were transfected with siNAs and incubated, as detailed elsewhere herein. Transfection efficiencies were determined by transfection with Cy-3 labeled siNA, and counting Cy 3-labeled cells, 16 hours after transfection. Cells were also examined for morphological changes compared with untreated cells.

Effect on Proliferative Potential

The potency of different siRNAs was examined by assessing their ability to inhibit the proliferation of cancer cell lines, using different parameters.

Direct Assays on Cells

Cytotoxicity induced by siRNA was studied by analyzing the amount of LDH released into the medium due to cell necrosis.

Proliferative potential measured by colony forming assays, with respect to the concentration of siRNA. Proliferative potential was also measured by BrdU incorporation, as BrdU is incorporated only into actively proliferating cells. After transfection of siRNA for 72 hours the cells were incubated with BrdU as per the protocol of Cabiochem. The quantity of BrdU incorporated was estimated by the absorbance values, compared with mock treated cells.

Effect on mRNA and Protein Levels

Cells transfected with the siRNA were analyzed for reduction in levels of specific mRNAs using real time quantitative PCR analysis or Northern blot analysis. In real-time PCR, the preparation of the first strand cDNA for the above was carried out using the kit from Qiagen. The first strand cDNA from siRNA, mock and untreated samples were used as templates and mRNA quantity were detected by normalizing against internal control. The fold change in mRNA levels was determined by the protocol of Kenneth J L and Thomas D S ("Analysis of relative gene expression data using real-time quantitative PCR and $2^{-\Delta\Delta Ct}$ method" *Methods* 2001; 25: 402-408).

The proliferative and metastatic potential of cancer cell lines treated with siRNA was also examined by measuring levels of Cyclin 1 or pCNA (proliferative cell nuclear antigen) mRNA using real-time quantitative PCR. These markers are indicators of proliferation and metastasis in head and neck, oral, and lung cancer, among others.

Protein

The protein levels of AurkB were analyzed by western blot. Although transfections of siRNA resulted in decreased mRNA levels, cells have various mechanisms by which they can cope up with the loss of mRNA levels.

The quantity of AurkB localised at centromers and kinetochores was also examined to determine the difference between treated and mock-treated cells. This provides insight into whether repression of AurkB is sufficient to interfere with cell division.

siNA Compositions

The present siNA may be used with or without additional factors. However, the present invention also provides cholesterol conjugated siNA of AurkB and EGFR complexed with PEI. The serum stability of these molecules were studied. The present invention also provides cholesterol conjugated siNAs of AurkB and EGR1 linked to thiolated F(ab)2 fragments of monoclonal antibodies of anti-EGFR. The effects of these conjugated siNAs were evaluated for their interferon responses.

Animal Models

The present invention demonstrates that siNAs compositions were able to inhibit tumor growth and cause tumor regression in animal models. Therefore the present compositions and methods are suitable and effective for therapy of cancer and proliferative diseases.

Treatment

The present invention provides methods and composition for inhibiting AurkB and/or EGFR expression, and therefore activity. Such inhibition is useful in the treatment and management of cancers and other proliferative diseases.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Design of 21, 22, 23, and 27 Nucleotide siRNA for Inhibition of AurkB and EGFR

Identification of Target Sites:

siRNA of 21, 23 or 27 nucleotides in length were designed using general methods disclosed in the literature (Henschel, A., Buchholz, F., Haberrnann, B. DEQOR: a web-based tool for the design and quality control of siRNAs *Nucleic Acids Res.* 2004; 32: W113-W120; Ui-Tei K, Naito Y, Takahashi F, Haraguchi T. Guidelines for the selection of highly effective siRNA sequences for mammalian and chick RNA interference. *Nucleic Acids Research* 2004; 32(3):936-48; Sui G., Soohoo C., el Affar B., Gay F., Shi Y., Forrester W. C. & Shi Y. A DNA vector-based RNAi technology to suppress gene expression in mammalian cells. *Proc. Natl. Acad. Sci. USA* 2002; 99: 5515-5520; Elbashir S M, Harborth J, Weber K, Tuschl T. Analysis of gene function in somatic mammalian cells using small interfering RNAs. *Methods* 2002; 26(2): 199-213; Kim D H, Behlke M A, Rose S D, M-S chang S Choi, Rosii J J. Synthetic dsRNA dicer-substrates enhance RNAi potency and efficacy. *Nat Biotechnol,* 2005; 23(2):222-6; Hornung V, Guenthner-Biller M, Bourquin C. Sequence-specific potent induction of IFN-α by short interfering RNA in plasmacytoid dendritic cells through TLR7. *Nature Medicine* 2005; 11: 263-270; Judge A D, Sood V, Shaw J R, Fang D, McClintock K. Sequence-dependent stimulation of the mammalian innate immune response by synthetic siRNA. *Nat. Biotechnol.,* 2005; 23(4):457-62.).

The following basic requirement were met when designing siRNA:

For designing 21 nucleotide siRNAs:
1. GC content is between 30-50%
2. 3'- of each siRNA has an overhang of dTdT For designing 22 & 23 nucleotide siRNAs:
1. All siRNAs start at 5'- with G or C
2. 3'- of each siRNA strand has a overhang of dTdT
3. GC content of duplex is between 40-50%
4. At least 5 A/U bases in the first 7 bases of 5'-terminal strand of antisense strand For designing 27 nucleotide siRNAs:
1. GC content of duplex is between 40-55%.
2. Sense strand is of 25 nucleotides, whereas antisense strand is 27 nucleotides resulting in a 2 nucleotide overhang at 3'- of the antisense strand.
3. Last 2 nucleotides of 3'-sense strand contains deoxysugar instead of ribosugar backbone.
4. 5'- of sense strand contains an overhang while 3'- is blunt ended.

Target Site:

The sequence of AurkB and EGFR genes were screened for accessible sites that met the above-mentioned criteria using various online available algorithms, and this analysis was supplemented with manual inspection. Based on these criteria, the following sites were taken into consideration for siRNA to AurkB (siRNA 1-3) and EGFR (siRNA 4-6). Specifically, siRNAs 1-6 (shown in Table 2 below) were generated based on target sequences in ORFs, as presented in Table 1 below.

TABLE 1

Target ORF sequences of AurkB (siRNA 1-3) and EGFR (siRNA 4-6) for which siRNA were synthesized

| siRNA | Gene ID | Target Sequence in ORF | Start site | End site |
|---|---|---|---|---|
| 1 (21mer) | NM_004217 | 5'- TTGATGACTTT GAGATTGG -3' (SEQ ID NO: 1) | 281 | 300 |
| 2 (22mer) | NM_004217 | 5'- GGAGGAGGATC TACTTTGATT -3' (SEQ ID NO: 2) | 500 | 520 |
| 3 (27mer) | NM_004217 | 5'- GAGGATCTACT TGATTCTAGAGTA -3' SEQ ID NO: 3) | 504 | 528 |
| 4 (21mer) | NM_00526 | 5'- AAGAAAGUUUG CCAAGGCA -3' (SEQ ID NO: 4) | 328 | 346 |
| 5 (23mer) | NM_00526 | 5'- GAGTGCAACCA GCAACAATTC -3' (SEQ ID NO: 5) | 3360 | 3380 |
| 6 (27mer) | NM_00526 | 5'- GCAACATCTCC GAAAGCCAACAAGG -3' (SEQ ID NO: 6) | 2494 | 2518 |

Example 2

Preparation of siRNA Molecules

The siRNA molecules were synthesized by chemical means employing commercially available machinery from various companies such as Applied Biosystems, Beckmen etc. These could be synthesized by any of the following standard chemical methods or procured from Qiagen. The chemical methods were classified based on the type of protecting group incorporated at the 2'-carbon position of the ribose sugar—

1. $2^1$-t-butyldimethylsilyl (TBDMS)
2. $2^1$-O-triisopropylsilyloxymethyl (TOM)
3. $2^1$-acetoxyethoxy chemistry (ACE)

Chemical synthesis of oligonucleotides is well known in the art, and is not detailed further.

Purification:

The siRNAs were purified by desalting, PAGE (Polyacrylamidegel electrophoresis) or IE-HPLC (Ion Exchange-High Performance Liquid Chromatography). The quality of each RNA strand was analyzed by MALDI-TOF and yields were determined by integrated spectrophotometer absorbance at 260 nm. During quality control by MALDI-TOF a difference of 4 atomic mass units was the maximum allowed difference from that predicted by theory. After obtaining comparable yields for each strand as determined by absorbance at 260 nm the sense and antisense strands were annealed and then vacuum lyophilized. At the time of experiment the lyophilized powders were suspended in RNA suspension buffer (100 mM KCl, 30 mM HEPES buffer (pH 7.5), 1 mM MgCl$_2$), heated for 1 min at 90° C. and incubated at 37° C. for 1 h to dissolve the lyophilized powder. By following these manufacturing protocols the following siRNA having different 3'-end modifications and lengths were synthesized (Table 2).

TABLE 2 siRNA synthesized and their end modifications for AurkB and EGFR genes.

| siRNA | Duplex sequence with overhangs | Yield |
|---|---|---|
| 1 SENSE ANTISENSE | 5'-r(UUG AUG ACU UUG AGA UUG G) dTdT -3' (SEQ ID NO: 7) 5'-r(CCA AUC UCA AAG UCA UCA A) dTdT -3' (SEQ ID NO: 8) | 296 µg/mL |
| 2 SENSE ANTISENSE | 5'-r(GGA GGA GGA UCU ACU UGA UU) dTdT -3' (SEQ ID NO: 9) 5'-r(AAU CAA GUA GAU CCU CCU CC) dTdT -3' (SEQ ID NO: 10) | 310 µg/mL |
| 3 SENSE ANTSENSE | 5'-r(GGA GGA UCU ACU UGA UUC UAG AG)dTdA -3' (SEQ ID NO: 11) 5'-r(UAC UCU AGA AUC AAG UAG AUC CUC CUC) -3' (SEQ ID NO: 12) | 297 µg/mL |
| 4 SENSE ANTISENSE | 5'-r(AAG AAA GUU UGC CAA GGC A) dTdT -3' (SEQ ID NO: 13) 5'-r(UGC CUU GGC AAA CUU UCU U) dTdT -3' (SEQ ID NO: 14) | 296 µg/mL |
| 5 SENSE ANTISENSE | 5'-r(GAG UGC AAC CAG CAA UUC) dTdT -3' (SEQ ID NO: 15) 5'-r(GAA UUG CUG GUU GCA CUC) dTdT -3' (SEQ ID NO: 16) | 325 µg/mL |
| 6 SENSE ANTISENSE | 5'-r(GCA ACA UCU CCG AAA GCC AAC AA)dGdG -3' (SEQ ID NO: 17) 5'-r(CCU UGU UGG CUU UCG GAG AUG UUG CUU) -3' (SEQ ID NO: 18) | 301 µg/mL |
| 7* SENSE ANTISENSE | 5'-r(GAG AGU AUC AGG GAC UUG UUC) dTdT (SEQ ID NO: 19) 5'-r(GAA CAA GUC CCU GAU ACU CUC) dTdT (SEQ ID NO: 20) | 325 µg/mL |

TABLE 2-continued siRNA synthesized and their end modifications for AurkB and EGFR genes.

| siRNA | Duplex sequence with overhangs | Yield |
|---|---|---|
| 8* SENSE ANTISENSE | 5'-r(GAC GCA UCA AUA GGC CAA UAC)dTdT (SEQ ID NO: 21) 5'-r(GUA UUG GCC UAU UGA UGC GUC)dTdT (SEQ ID NO: 22) | 325 µg/mL |

*siRNA 7 and 8 are scrambled siRNA for the gene AurkB and EGFR respectively. This means that these siRNA do not target any gene of interest. These were used as negative controls and always referred in experiments as mock treated.

Example 3

Expression Analysis of Aurk B and EGFR in Different Cancer Cell Lines

Gene Expression Analysis by Quantitative Real Time PCR—
Levels of AurkB and EGFR mRNA in different cancer cell-lines were compared with those of normal diploid cells. Expression levels of genes were compared by quantitative real time PCR. The cell-lines used in this study include PC3 (prostate cancer), A549 (non small cell lung cancer), A431 (epidermoid cancer), HeLa (cervical cancer), SCC-4 (squamous cell carcinoma of tongue); and, of normal cells, HFF-2 (normal diploid fibroblasts) and ARPE-19 (diploid retinal pigmented epithelial cells). The preparation of first strand cDNA for real time PCR analysis was carried out using Qiagen Fast lane cell cDNA kit (Cat. no. 215011) with minor modifications. Briefly 20,000 cells were pelleted, washed once, lysed, and genomic DNA contamination eliminated by the addition of gDNA wipeout buffer (Qiagen) and incubating at 42.5° C. for 30 min. First strand cDNA was synthesized by the addition of Quantiscript reverse transcriptase at 42.5° C. for 45 min followed by incubation at 95° C. for 3 min. The first strand cDNA prepared was either used immediately for quantitative real time PCR or stored till further use at −20° C.

Cancer cells (HeLa, A549, PC3 and A431) were maintained at a confluence of 60-70-%. Fresh medium was added 24 h prior to harvest. The first strand cDNA was prepared as described above from the experimental cells following protocol of the Fast lane cell cDNA kit (Qiagen). First strand cDNA from antisense, mock and untreated samples were used as template and quantified the levels of mRNA by normalizing against the internal control β-actin.

The expression of AurkB and EGFR varied by several fold in comparison with that of the normal diploid cancer cells. Except for prostate cancer cell line PC3, all other cancer cell lines tested in this study expressed more of both AurkB and EGFR mRNA than control cells, as shown in the Table 3.

TABLE 3

Relative expression of AurkB and EGFR mRNA in cancer cells compared with diploid cells

| Cell line | mRNA | Fold change over HFF-2 cells | Fold change over ARPE-19 cells |
|---|---|---|---|
| HeLa | AurkB | 2.63 fold increase | 3.41 fold increase |
|  | EGFR | 24.81 fold increase | 6.78 fold increase |

TABLE 3-continued

Relative expression of AurkB and EGFR mRNA in cancer cells compared with diploid cells

| Cell line | mRNA | Fold change over HFF-2 cells | Fold change over ARPE-19 cells |
|---|---|---|---|
| A549 | AurkB | 2.54 fold increase | 3.29 fold increase |
|  | EGFR | 5.61 fold increase | 1.53 fold increase |
| PC3 | AurkB | 1.48 fold decrease | 1.72 fold decrease |
|  | EGFR | 2.65 fold decrease | 6.27 fold decrease |
| A431 | AurkB | 2.44 fold increase | 3.15 fold increase |
|  | EGFR | 129 fold increase | 35.40 fold increase |

Western Blot Analysis of AurkB and EGFR

Cells were grown to 60-70% confluence with a change of medium 24 h prior to harvesting cells. Protein lysates were made using mammalian protein extraction reagent (MPER, Calbiochem) following the manufacturer's protocol. Based on a Bradford total protein estimation, equal quantities of proteins were resolved over 15% SDS PAGE for AurkB and 10% SDS-PAGE for EGFR. The proteins resolved over the SDS-PAGE were subjected to western blot transfer at 110 V for 70 min onto a pre-wet nitrocellulose membrane along with pre-stained rainbow molecular weight markers (Cat # RPN755, Amersham Biosciences). The transfer of proteins by electro blotting was confirmed by Ponceau S staining (Sigma). The blot was incubated in blocking solution (5% skim milk powder) for 1 h at room temperature on an rocking platform. Before incubating with rabbit anti-AurkB (Cat # A5102, Sigma) and mouse alpha tubulin antibody (Cat # T6199, Sigma) as internal control, the blot was washed over an orbital shaker three times for 5 min each, with a change of PBST (phosphate buffered saline containing 0.1% Tween 20). The blot was then incubated with primary antibodies overnight at 4° C. before washing with PBST as above to remove any non-specific bound primary antibodies. After washing with PBST the blots were incubated with secondary antibodies conjugated with alkaline phosphatase for two hours at room temperature over an orbital shaker. These secondary antibodies include rabbit anti-mouse antibody conjugated with alkaline phosphatase (Cat # A3438, Sigma) to detect tubulin while goat anti-rabbit antibody (Cat # 111-055-003, Jackson) was used to detect AurkB antibody. The blots were washed three times with PBST for 10 min each before being developed with BCIP/NBT substrate solution (Cat # B6404, Sigma). The protein bands corresponding to AurkB (41 KDa), EGFR (170 KDa) and tubulin (50 KDa) as endogenous control were detected as shown in FIGS. 1 and 2.

Figure 1:
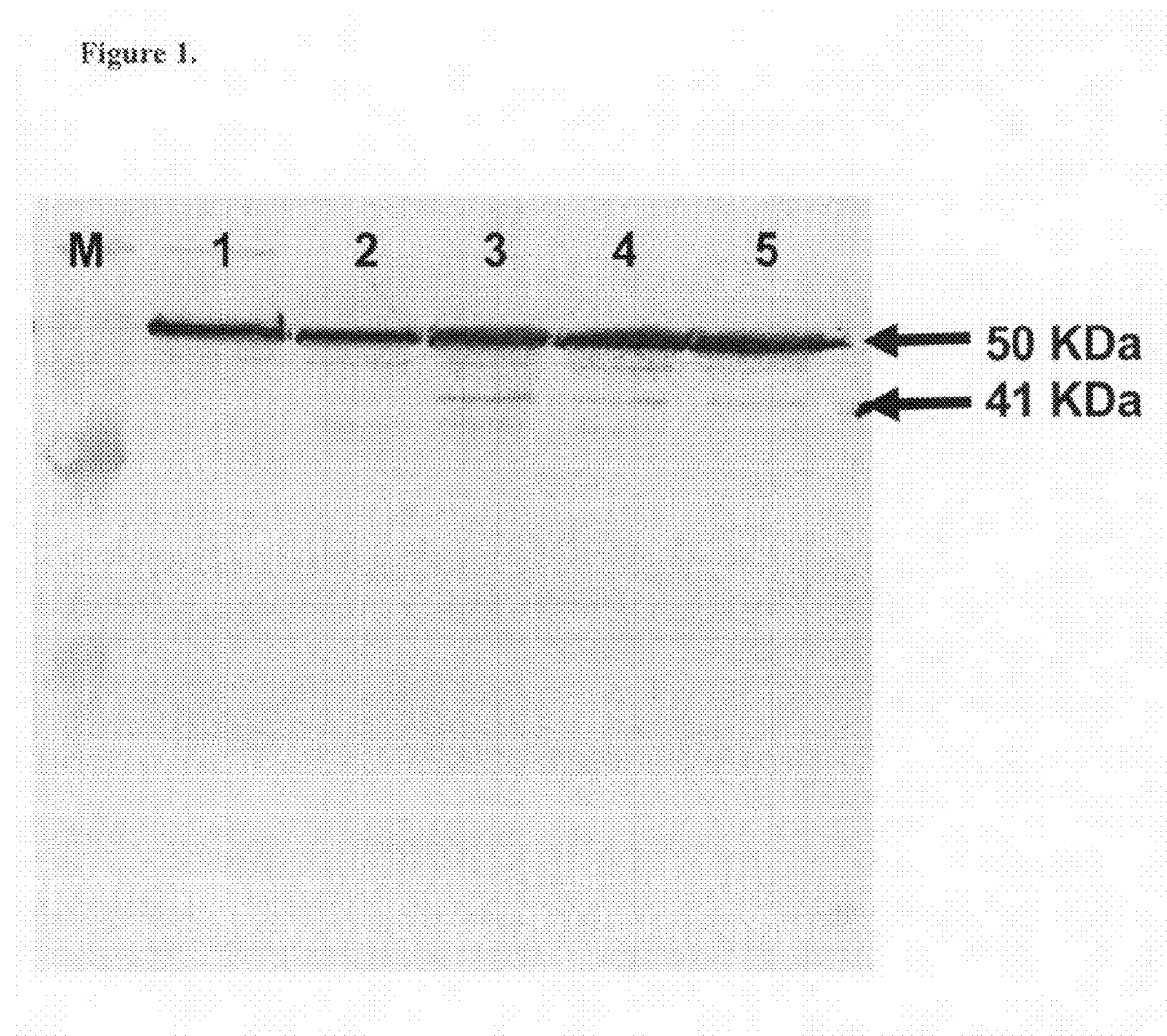
FIG. 1. Expression of AurkB in ARPE-19 (normal diploid retinal pigmented epithelial cells, Lane 1), HeLa (cervical cancer, Lane 2), A431 (epidermoid cancer, Lane 3), A549 (non small cell lung cancer, Lane 4) and PC3 (prostate cancer cells, Lane 5) were analyzed for expression of AurkB (41 KDa) and tubulin (50 KDa) as endogenous control.

In FIG. 1, Cell lines ARPE-19 (normal diploid retinal pigmented epithelial cells, Lane 1), HeLa (cervical cancer, Lane 2), A431 (epidermoid cancer, Lane 3), A549 (non small cell lung cancer, Lane 4) and PC3 (prostate cancer cells, Lane 5) were analyzed for expression of Aurorakinase B. Crude protein lysates from the respective cell lines were resolved over 15% SDS-PAGE and blotted onto nitro cellulose membrane. Membranes with transferred proteins were probed with rabbit anti-aurorakinase B antibody and mouse anti-alpha tubulin monoclonal antibody detected by goat anti-rabbit antibody ALP conjugated goat anti-mouse antibody conjugated with ALP. In blot 41 KDa represents AurkB while 50 KDa represents tubulin detected as endogenous control. AurkB is expressed in all cells.

Figure 2:
FIG. 2. Expression of EGFR in cell lines HeLa (cervical cancer, Lane 1), PC3 (prostate cancer cells, Lane 2), A549 (non small cell lung cancer, Lane 3), A431 (epidermoid cancer, Lane 4), SCC-4 (squamous cell carcinoma of tongue, Lane 5), HFF-2 (normal diploid fibro blasts, Lane 6) and ARPE-19 (normal diploid retinal pigmented epithelial cells, Lane 7). EGFR (170 KDa), tubulin (50 KDa)

In FIG. 2. Cell lines HeLa (cervical cancer, Lane 1), PC3 (prostate cancer cells, Lane 2), A549 (non small cell lung cancer, Lane 3), A431 (epidermoid cancer, Lane 4), SCC-4 (Squamous cell carcinoma of tongue, Lane 5), HFF-2 (normal diploid fibro blasts, Lane 6) and ARPE-19 (normal diploid retinal pigmented epithelial cells, Lane 7), and were analyzed for expression of epidermal growth factor receptor 1 (EGFR). Crude protein lysates from the respective cell lines were resolved over 10% SDS-PAGE and blotted onto nitro cellulose membrane. Membranes with transferred proteins were probed with rabbit anti-EGFR antibody and mouse anti-alpha tubulin monoclonal antibody detected by goat anti-rabbit ALP conjugated and goat anti-mouse antibody conjugated with ALP. In blot 170 KDa represents EGFR while 50 KDa represents tubulin detected as endogenous control. EGFR is expressed in all cells, but epidermoid carcinoma cell line A431 and squamous cell carcinoma of tongue SCC-4 expressed greater amounts.

Example 4

Testing of Efficacy

A. In Different Cell Lines:

Oligonucleotide Transfections/siRNA Transfections:

HeLa (cervical cancer), SCC-4 (oral cancer), A549 (non small cell lung cancer), A431 (epidermoid cancer), PC-3 (prostate cancer), HFF-2 (normal diploid fibroblasts) and ARPE-19 (normal diploid retinal pigmented epithelial cells) cell lines were obtained from ATCC and were maintained at 70-80% confluence with change of medium prior to 24 h of transfection in T-25 flasks (cat #156367, Nunc). Cell lines were used for all transfections of siRNA before reaching passage number ten, unless otherwise indicated. At the time of transfection cells were trypsinized and reseeded into either 24-well plate (cat #143982, Nunc), or any other standard tissue culture disposable plastic ware, at an appropriate cell density. For experiments, unless otherwise stated, all transfections were carried-out in a 24-well plate with varying cell densities depending on cell-lines used for a given experiment. Each well of 24-well plate was seeded with appropriate cell densities one hour prior to transfections with growth medium not exceeding 400 μL and incubated at 37° C. with 5% $CO_2$. To this medium diluted siRNA were added to a final concentration of 10 nM (in 97 μL of Opti-MEM I added 0.3 μL of siRNA from a 20 μM stock. 3 μL of Hiperfect (Qiagen), a transfection agent containing both anionic and cationic lipids which forms liposomes, was then added and mixed by vortexing before incubating at room temperature for 10 min. For combination of siRNAs such as EGFR and AurkB individual siRNA were mixed 10 nM each and used. In all experiments a mock control of siRNA 7 and/or siRNA 8 was used.

Figure 3:
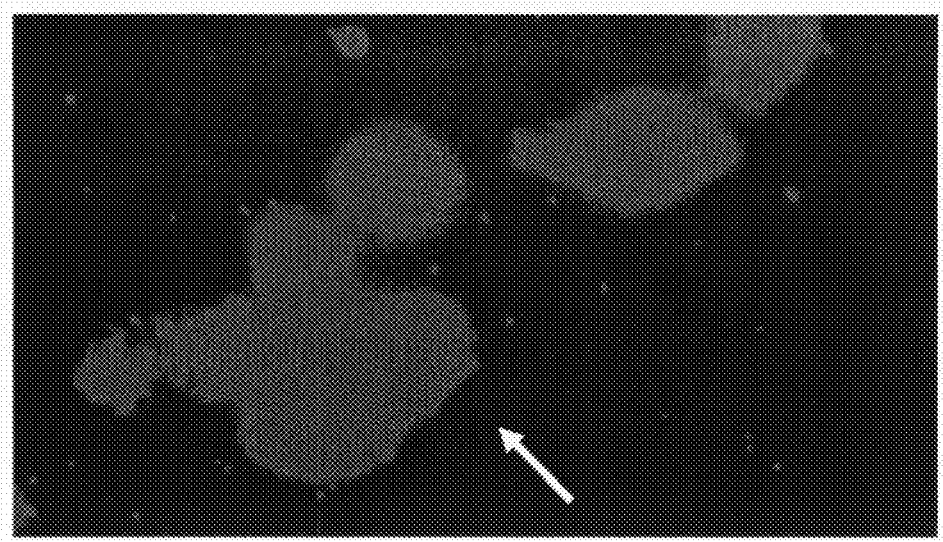
FIG. 3. HeLa cells transfected with Cy3 labeled siRNA. Arrowhead indicates Cy3 labeled siRNA at the end of 16 h of transfection distributed inside the cytosol.

At the end of incubation siRNA-liposome complexes, were mixed thoroughly and added drop wise gently to each well containing cells, mixed, then incubated at 37° C. in 5% $CO_2$. Transfection efficiencies were obtained for each cell line by counting number of cells showing Cy3 labeled siRNA 16 h after transfection. Cells were trypsinised, washed once in PBS, and suspended in PBS. Cells were observed with an inverted fluorescent microscope and the number of fluorescent cells and total number of cells were counted from 15 different fields. The percentage of Cy3 labeled cells corresponds to the transfection efficiency, and ranged from 97% for HeLa to 70% for A549 cells. See Table 4 and FIG. 3 (showing an example transfection with siRNA 7) (siRNAs 1-8 all gave similar results).

TABLE 4

Transfection efficiencies as determined by Cy3-labeled siRNA for different cell lines.

| Cell line transfected | % Transfection |
| --- | --- |
| A431 | 89 ± 3.0 |
| HeLa | 97 ± 5.0 |
| PC3 | 85 ± 3.0 |
| SCC-4 | N.D |
| A549 | 70 ± 1.0 |
| HFF-2 | 93 ± 1.0 |
| ARPE-19 | 85 ± 5.0 |

Figure 4:
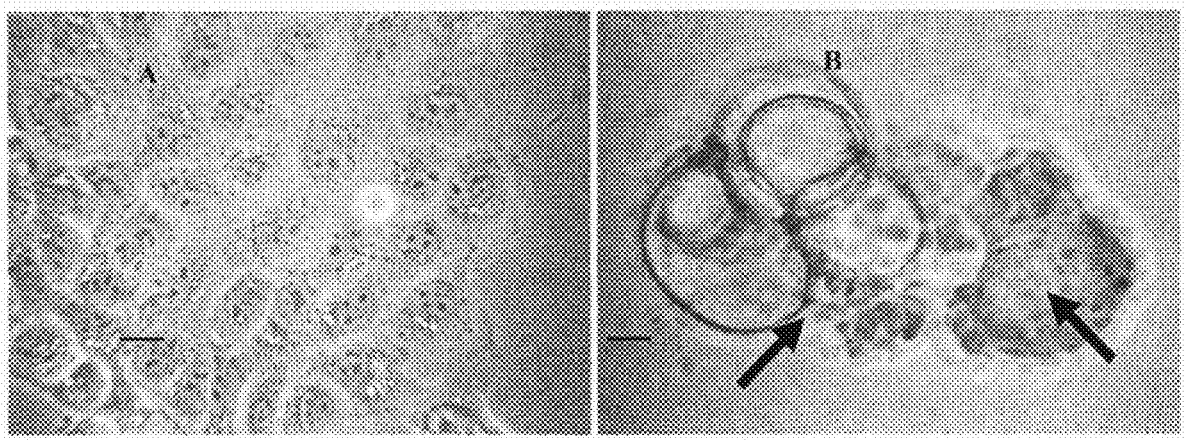
FIG. 4. Morphology of cells transfected with siRNA. Scale bar 1 cm=11 μm.

B) Morphological Features Observed Upon Transfection of Cell Lines with siRNA 48 h after transfection, cells (A431, SCC-4, A549 & HeLa) showed varied morphological features in comparison with untreated cell lines. The combination of siRNA 3 and 6 caused significant cell death and morphological changes. Significant cell death was noted in cells transfected with siRNA 6 but no morphological changes. Cells treated with siRNA 3 assumed a spherical shape and detached gradually from the culture plate by 72 h of transfection as shown in the FIG. 4.

C) Identification of Potencies of Different siRNAs Designed in Inhibiting Proliferation of Cancer Cellines:

PC3 (prostate) and HeLa (cervical) cancer cell lines were transfected with differing siRNAs (of different lengths) alone, and in combinations. Twenty four hours after transfection, cells were plated in triplicate at a density of 8000 cells per well in a 96-well plate. After 72 h, cells were incubated for three hours with BrdU according to kit instructions (cat #QIA58, Calbiochem). BrdU incorporation was stopped by the addition of a fixation reagent and cells were permeabilized to allow labeling with anti-BrdU antibody. The antibody is conjugated with horseradish peroxidase (HRP), which converts $H_2O_2$ to chromogenic product which is measured by absorbance values at 450 nm with a reference filter at 540 nm. The absorbance lead to an estimation of the proportion of cells that were in S-phase after treatment with siRNA compared with cells treated with mock. All experiments were performed in triplicate and their mean averages and standard deviations were obtained. The statistical significance was determined between mock treated cells vs siRNA treated cells by paired two tail t-test where $P \leq 0.05$. BrdU incorporation following transfection with siRNA 3 and 6 was 30 & 58%, respectively, of the incorporation in mock treated cells. Treatment of cells with siRNA 1, 2, 4 or 5 also led to decreased BrdU incorporation compared to mock, but less so than cells treated with siRNA 3 or 6 (FIG. 5). Statistical significance was found between mock treated and all siRNA treated cells, between siRNA 2 and 3, between siRNA 4 and 5, between siRNA 5 and 6, as well as between siRNA 4 and 6. These results indicate that siRNA 3 is more potent than siRNA 2, and siRNA 6 is more potent than siRNAs 4 and 5.

D) Real Time Quantitative PCR Analysis:

Without being bound by theory, it is believed that transfection of cells with siRNA results in activation of the RNAi pathway, in which mRNA complementary to the siRNA is degraded, thereby reducing levels of mRNA and the resultant protein encoded by the mRNA. The potency of a siRNA may be determined by measuring mRNA levels after siRNA transfection. Quantitative real time PCR was used to determine mRNA levels of both AurkB and EGFR among different cell lines transfected with siRNA, compared with mock transfected cells (Table 5).

TABLE 5

Fold decrease in expression of AurkB and EGFR levels after 72 h after siRNA transfection of different cancer cell-lines, as determined by real time PCR.

| Cell-line | siRNA3 Fold change in AurkB mRNA | siRNA6 Fold change in EGFR mRNA | siRNA 3 & 6 combination Fold change | |
| --- | --- | --- | --- | --- |
| | | | AurkB mRNA | EGFR mRNA |
| HeLa | 4.80 | 5.72 | 5.21 | 6.84 |
| A431 | 5.20 | 3.09 | N.D | N.D |
| PC3 | 5.13 | 1.51 | 6.8 | 3.46 |
| A549 | 1.79 | 4.47 | N.D | N.D |
| SCC-4 | 3.77 | 4.86 | 5.06 | 2.61 |

In general, the combination of siRNA 3 and 6 was more effective in reducing AurkB and EGFR mRNA than siRNA 3 or 6 alone.

E) Analysis of AurkB Protein Level:

PC3, A431, A549 and HeLa cells transfected with siRNA were subjected to total protein extraction after 72 h of transfection. siRNA treatment reduced AurkB protein expression by as much as 90% (e.g. FIG. 6) and EGFR as much as 95% (e.g. FIG. 7) compared mock treated samples. The decline in protein expression reflects the decline in mRNA levels seen with real-time PCR.

For example, in FIG. 6, lung cancer cell line A549 was transfected with siRNA 3 and analyzed for AurkB expression 72 h later, compared with mock-treated cells. Equal quantity of protein was loaded on all wells and, to ensure similar quantities of protein get transferred endogenous control protein alpha tubulin (50 kDa) was also detected in blot. Lane 1. siRNA 3 transfected A549 cell line where arrow head indicates faint band of Aurora B, a 41 kDa protein. Lane 2. Mock treated sample where Aurora B protein was detected in fairly good quantities over the siRNA treated samples. Lane 3. Rainbow low Molecular weight markers.

FIG. 7 shows a Western blot of A549 cells, 72 h after transfection with siRNA 6. Equal quantity of protein was loaded on all wells and to ensure similar quantities of protein get transferred, endogenous control tubulin (50 kDa) was also detected in blot. Lane 1. siRNA 6 transfected A549 cell line where arrow head indicates missing band of EGFR, a 170 kDa protein. Lane 2. Mock treated sample where EGFR protein was detected in fairly good quantities over the siRNA treated samples. Lane 3. Rainbow high molecular weight markers.

F) Determination of Proliferation & Metastatic Potential of Cancer Cell Lines Treated with Antisense RNA:

1) Biomarker analysis for cell proliferation efficiency: Ki-67 antigen and Proliferative Cell Nuclear Antigen (PCNA) are markers for cancer proliferation and metastasis. Expression of these antigens correlates with poor clinical prognosis.

72 h after transfection, Ki-67 expression was determined by ELISA (Sui G., Soohoo C., el Affar B., Gay F., Shi Y., Forrester W. C. & Shi Y. (2002) A DNA vector-based RNAi technology to suppress gene expression in mammalian cells. *Proc. Natl. Acad. Sci. USA*, 99, 5515-5520). Monoclonal anti-Ki-67 antigen antibody (Sigma) was used as primary antibody while goat anti-mouse IgM-μ chain-specific HRP conjugated antibody as secondary antibody. Absorbance values were obtained at 450 nm and their mean and standard deviation compared to mock treated and untreated controls. Cancer cells transfected with siRNA showed decrease in expression levels of Ki-67 antigen over untreated cells, ranging from 91.3% of untreated cells to as low as 39% of untreated (Table 6). The decrease in levels of Ki-67 supports that inhibition of AurkB, EGFR, or both, decreased the mitotic index of transfected cells.

TABLE 6

Inhibition of AurkB, EGFR or both decreases expression of Ki-67 antigen as determined by ELISA.

| Treatment | A431 | A549 | PC3 | HeLa |
|---|---|---|---|---|
| siRNA 3 | 64.7 | 78.26 | 81.81 | 42.1 |
| siRNA 6 | 64.7 | 91.3 | 39 | 68.42 |
| siRNA 3&6 | 50 | 73.91 | 39.5 | 43.85 |
| Untreated | 100 | 100 | 100 | 100 |

PCNA mRNA was measured using quantitative real time PCR in PC3, A431, SCC-4 & A549 cell lines transfected with siRNA. (Table 7) The treatment of lung cancer cell line A549 with siRNA3 significantly reduced PCNA levels. The combination of siRNA 3 and 6 showed an additive effect in reducing levels of PCNA over individually treated siRNA in SCC-4 cells. The reduced levels of PCNA expression, over mock-transfected samples, indicates that the proliferation potential of these cell lines has been considerably reduced.

TABLE 7

Fold decrease in expression of PCNA on transfection of different cell lines with siRNA against AurkB and/or EGFR

| siRNA transfected | A431 cells | A549 cells | PC3 cells | SCC-4 cells |
|---|---|---|---|---|
| siRNA3 | 1.89 | 4.09 | 1.69 | 1.62 |
| siRNA6 | 0.85 | 0.87 | 1.51 | 1.19 |
| siRNA3&6 | N.D | N.D | 1.34 | 2.33 |

F) Cell Proliferation Assay:

siRNA 3 and 6 successfully reduced respective mRNA as well as protein levels, relative to their mock or untreated samples. The affect of such inhibition on cellular metabolism was determined by measuring the ability of transfected cells to reduce NAD or NADP to NADH or NADPH, respectively. 24 h after siRNA transfection, cells (HeLa, A431, A549 & PC3) were trypsinized, counted and replated at a concentration of 1000 cells per well in a 96-well plate. Cells were incubated for another 48 h before measuring cell metabolic status following the protocol of the Cell-titer 96 aqueous non-radioactive assay kit from Promega (cat #G5421). Briefly, 100 µL of growth medium was withdrawn from 96 well plates, to which was added 20 µL of Cell titer 96 aqueous solution, and incubated for 4 h at 37° C. in 5% $CO_2$. Plates were read at 490 nm with a reference filter of 630 nm. The mean and standard deviation of the absorbance value from triplicate was determined and the percentage of metabolically active cells or cell proliferation was estimated with respect to mock treated cells. The proliferation efficiencies varied depending on cell line, siRNA identity, and siRNA concentration. Transfection with the siRNA 3 and 6 combination greatly reduced metabolic activity, as shown in FIG. 8.

FIG. 8 shows different cell lines treated with siRNA 3 (10 nM), siRNA 6 (10 nM) and combination of siRNA 3 and 6 at 10 nM as well as 5 nM concentrations each. The statistical significance was determined between mock treated cells vs siRNA transfected cells by paired two tail t-test where $P \leq 0.05$. Significant proliferation inhibition was obtained in all cell lines (PC3, A549, A431 and HeLa) in which AurkB, EGFR or both were targeted. However the there was no additive effect found in any of the cell lines when both mRNAs were inhibited simultaneously using siRNAs 3 and 6 in combination.

E) Colony Forming Assay:

Colony forming assays were used to assess the ability of siRNA-treated cells to initiate and develop a tumor. 24 h after transfection of cells (HeLa, A431, A549 and PC3) in 24 well plates, the cells were trypsinized, counted, and replated at a concentration of 300 cells per 6-well plate, in triplicate. Controls of mock treated and untreated cell-lines were also prepared. After 10 days of incubation, cells were washed once with PBS and stained with 300 µL of 0.1% crystal violet for 5 min. before washing three times with PBS. This can be seen readily in FIG. 9, which shows prostate cancer cell line PC3 transfected and seeded in triplicate at a density of 300 cells/well in a six well plate. In FIG. 9, A-C represent mock treated cells while D-F represent siRNA 3 and 6 treated cells.

The number of colonies of containing at least 50 cells were counted with an inverted microscope. Standard deviation was derived from triplicates and the percentage of colony formation inhibition was obtained using the following formula:

Rate of colony formation inhibition=(Control colony forming rate−experimental colony forming rate)/control colony forming rate×100.

Treatment of different cancer cell-lines inhibited colony forming ability from 100-57%, in a dose dependent manner. FIG. 10 shows colony forming efficiency of different cell lines treated with siRNA 3 (10 nM), siRNA 6 (10 nM) and a combination of siRNA 3 as well as 6 at 10 nM and 5 nM concentrations each. All cell lines treated with siRNA 3 and 6 showed different levels of inhibition to form colonies in comparison with that of mock treated and untreated cell lines. Cell line HeLa showed 100% colony forming inhibition when treated with siRNA 3 which suggests 100% dependency of cervical cancer on AurkB proteins. In cell lines PC3, A549 and A431, AurkB inhibition resulted in significant inhibition of colony forming ability over mock treated cells. EGFR repression also resulted in a decrease in colony forming ability. The statistical significance was determined between mock treated cells vs siRNA transfected cells by paired two tail t-test where $P \leq 0.05$. Significant inhibition of colony forming ability was observed in all the cells treated with siRNA in comparison with that of mock treated cells. However there was no significant results obtained in colony inhibition between mock treated and untreated cells. And also there was no additive effect observed by simultaneous repression of AurkB and EGFR.

F) Effect of siRNA Transfection on Cancer Cell Death and/or Membrane Integrity.

LDH release was used to determine the cytotoxicity of reduced levels of AurkB and EGFR on transfected cells. Cell-lines (PC3, A431, A549, HeLa, ARPE-19 and HFF-2) were transfected with siRNA and plated at a density of 20,000 cells/well in a 24-well plate, in triplicate. After 72 h, cells were briefly centrifuged to clear dead floating cells and 100 µL of spent medium was withdrawn into a separate 96-well plate to assess LDH, following the protocol of Sigma LDH assay kit (Cat. # TOX-7). The absorbance values were measured at 490 nm with a reference filter of 690 nm. The mean and standard deviation was calculated from triplicate wells and compared against untreated cell-lines. As shown in FIG. 11, LDH was released following inhibition of AurkB and/or EGFR mRNA, indicating cellular necrosis and/or compromise of membrane integrity. Normal diploid cell line ARPE-19 remain only partially effected in comparison with that of the cancer cell lines tested. Inhibition of AurkB in A549 and A431 resulted in 150% and 60% release of LDH over mock treated cells respectively whereas PC3 and HeLa showed 65% and 52% release of LDH. By comparison, repression of EGFR has resulted in 150%, 90%, 47% and 100% release of LDH from PC3, A549, A431 and HeLa cells, respectively, over their mock treated samples. Repression of both EGFR and AurkB simultaneously did not cause any additive affect on release of LDH. All siRNA treated cells showed statistically significant (at $P \leq 0.05$) release of LDH in comparison with that of mock treated cells except in case of ARPE-19 cells where no significance was found following AurkB inhibition. Limited quantities of LDH released from the normal cells in comparison over cancer cells shows that there is an inherent instability in case of cancer cells to cope-up with the loss of AurkB or EGFR.

G) Effect of AurkB and/or EGFR Inhibition on Apoptosis.

To determine whether siRNA transfection induces apoptosis, Annexin V was examined in transfected PC3, A549, A431, HeLa, HFF-2 and ARPE-19 cells. Following Calbiochem's Annexin V-PE Apoptosis detection kit, cells were trypsinized, suspended in buffer and stained with PE labeled Annexin V at different time intervals (8 h, 16 h, 24 h, 48 h and 72 h) after siRNA transfection. The number of cells showing binding to Annexin V was recorded from a total of 150 cells per sample. Apotosis induction was not observed.

Example 5

In Vitro Testing of Combinations

A) Cancer Cell Invasion Assay:

The ability of cancer cells to metastasize is enhanced by their secretion of matrix metalloproteinases, and expression of E-cadherin. Cell-lines (A549 and PC-3) were plated in a collagen IV coated 24-well plates at a density of $3 \times 10^4$ cells/per well immediately after transfection in triplicate. Twenty Four hours after plating in 24-well plate a scratch was inflicted using a 10 μL pipette tip across the well where a monolayer of cells have been established. The number of cells that migrated into the scratched area was counted at 8 h and 24 h after scratching. This can be seen in FIG. 12, showing the scratch assay-showing invasibility of lung cancer cell line A549. Cells were seeded at a density of $3 \times 10^4$ per well in collagen (0.3 mg/mL) coated 24-well plate. siRNA 3 and 6 transfections were performed in triplicate as explained earlier with 5 nM of each siRNA. At 24 h after transfection scratch was inflicted with pipette tip and growth medium was added replacing spent medium. Number of cells migrated into the scratched area (denoted by rectangular dotted black colored boxes) were counted at 8 h and 24 h after infliction of scratch.

A-C: siRNA 3 and 6 transfected A549 cell line. D-F: Mock transfected cell line.

A & D: 0 h of scratch infliction. B & E: 8 h of scratch infliction. C & F: 24 h of scratch infliction.

This effect was quantified, as shown in FIG. 13. Cell lines PC3 and A549 were transfected with siRNA in a 24-well plate. At the end of 24 h of transfection a scratch was made across each well of 24-well plate with the aid of 10 μL pipette tip. Wells were washed once with PBS and fresh growth medium was added to remove detached and dead cells while making scratch. Cells were observed after 8 h of scratch as well as at 24 h of scratch infliction. Numbers of cells that have migrated into the scratched are were recorded. Of the cell lines PC3 and A549 showed 60% and 47% inhibition in migration of cells respectively. At 24 h, only 45% and 17% of cells exposed to siRNA 3 (AurkB knockdown cells) have migrated in case of PC3 and A549 cells respectively. In case cells exposed to siRNA 6 (EGFR knockdown cells), 47% and 23% cells have migrated for PC3 and A549 cells respectively. Whereas the cell migrations stood at 57% and 9% when exposed to both siRNA 3 and 6, i.e., when both AurkB and EGFR were knocked down for PC3 and A549 cells respectively. This indicates that there was an additive effect on inhibition of cell migration by simultaneous knockdown of AurkB and EGFR in case of A549 cell line. The results obtained were found to be statistical significant between mock treated cells vs. siRNA treated cells at 24 h by paired two tail t-test where $P \leq 0.05$.

Overall, transfection of siRNA 3 resulted in 70% and 50% inhibition of migration of PC3 and A549 cell-lines, respectively. siRNA 6 transfection inhibited cell migration to the extant of 40% and 70%, respectively, for cell-lines PC3 & A549. Transfection with siRNA 3 and 6, inhibiting both AurkB and EGFR, inhibited cell migration into the scratched by 85% and 80% for cell-lines A549 and PC3, respectively.

B) Growth Kinetics of Different Cancer Cell-Lines Treated with siRNA:

Cancer cell-lines as well as normal diploid cell-lines were transfected with siRNA 3 and/or 6 in a 24-well plate. 24 h after transfection, the cells were trypsinized and seeded at a density of 1000 cells/well, in triplicate, in a 96-well plate. 48 h later, the number of cells that were metabolically active was determined using Cell-titer 96 aqueous solution kit from Promega for every 24 h until 8 days after transfection. The number of cells present at every 24 h was determined and thus the growth rate of siRNA transfected cells was by MTS assay indicating the metabolic status of the cells. The statistical significance was determined by paired two tail t-test where $P \leq 0.05$. The results are summarized in FIGS. 14 to 17.

FIG. 14 shows the growth rate epidermoid carcinoma cell line A431 over a period of 8 days from the date of transfection (with siRNA 3, 6 or 3 & 6), as determined by MTS. Statistically significant data was obtained for the following: Day 3 and 4—between siRNA (3, 6 as well as 3 & 6) treated and mock treated samples. Further among siRNA 3, siRNA 6 and siRNA 3 & 6 combination treated cells. Day 5, 6, 7 and 8—between siRNA (3 as well as 3 & 6) treated and mock treated samples. Further among siRNA 3 and siRNA 3 & 6 combination treated cells. Inhibition of both AurkB and EGFR showed the lowest growth rate.

FIG. 15 shows prostate cancer cell line PC3 percent growth rate over a period of 8 days from the date of transfection (with siRNA 3, 6 or 3 & 6) compared with that of mock treated cells. Statistically significant data was obtained for the following: Day 3–between siRNA 3 treated and mock treated cells; Day 4, 5 and 6—between siRNA 3 as well as combination of siRNA 3 and 6 treated and mock treated cells; Day 7 and 6—combination treated cells and mock treated cells.

FIG. 16 shows non-small cell lung cancer cell line A549 growth rate over a period of 8 days from the date of transfection (with siRNA 3, 6 or 3 & 6) compared with that of mock treated cells. Statistically significant data was obtained for the following: Day 3 & 4—between siRNA 3 treated and mock treated cells.

FIG. 17 shows normal diploid retinal pigmented epithelial cells ARPE-19 growth rate over a period of 8 days from the date of transfection compared with that of mock treated cells. Statistically significant data was obtained for the following:

Day 4 & 5—significant growth inhibition has been observed between siRNA 3 and siRNA 3 & 6 combination treated cells vs mock treated cells. With siRNA 6 treated cells there was no significant decrease in growth rate on any of the days. The increase in growth rate of siRNA treated cells has been observed on Day 8 was due to confluence in mock treated cells. siRNA treated cells slowly reach confluence due to inhibition in growth of these cells observed during until the fourth day of transfection.

Of all the cells treated, cancer cells A431 (epidermoid cancer) showed maximum inhibitory effect even after 8 days of transfection. However normal diploid cells ARPE-19 showed very limited effect on inhibition in growth of cells. This indicates that siRNA selectively inhibited cancer cells.

C) Effect of siRNA Transfection on Cell Cycle of Cancer Cell-Lines:

Because cancer cells always remain in a state of proliferation, the number of cells that remain at a given time in S-phase of cell cycle determines the growth potential of a tumor. siRNA transfected cells (from cell lines PC-3 and HeLa) were plated at a density of 8000 cells per well in a 96-well plate to determine the effect of siRNA 3 and/or 6 on the cell cycle and, thus, their ability to control the growth index of the tumor cell-lines. 72 h after transfection, cells were subjected to BrDu incorporation to determine the number of cells that were in the S-phase of cell cycle as described above. From the absorbance values the percent of cells that were in S-phase of the cell cycle was obtained with reference to the mock treated cells. All the experiments were performed in triplicate and their mean averages and standard deviations were obtained. With prostate cancer cell line PC3, transfection with siRNA 3 and/or 6 and inhibited the ability of cells to progress through the S-phase of the cell cycle. Inhibition was greatest with PC3 (25% of control), while HeLa cells were 75-80% of mock-treated control, indicating much less inhibition. The data also indicated an additive effect of transformation on PC3 with both siRNA 3 and 6.

D) Serum Stability of siRNA Conjugated with Cholesterol and Complexed with Hiperfect Transfection Agent:

Cholesterol was conjugated to the 3'-end of either sense or antisense strand of siRNA 3 or 6. The cholesterol conjugated siRNA was compared with unconjugated siRNA for serum stability as well as for the ability to inhibit AurkB and EGFR expression in vitro.

Serum stability was tested on 1 µg of siRNA, incubated with 10 µL of 100% human serum at 37° C. for 24 h, 48 h and 72 h. At the end of the incubation, siRNAs were examined over 1% agarose gel electrophoresis. A mobility shift observed in the siRNA conjugated with cholesterol was due to binding of various serum proteins and thus protecting siRNA from degradation by serum nucleases. As seen in FIGS. 18 and 19, sense strands conjugated with cholesterol were more stable than conjugated antisense strands or unconjugated siRNA. In addition, the complexation of siRNA with the Hiperfect transfection agent did not enhanced serum stability. siRNA conjugated with cholesterol at 3'-end of sense strand was found to be more stable and could be detected even after 48 h of incubation at 37° C. in 100% serum conditions. Of the two siRNA, siRNA 6 was found to be more stable over the siRNA3. This could be due to an increase in GC content and a resulting high Tm.

The ability to inhibit mRNA was examined in HeLa cells. Cholesterol-conjugated siRNA 3 and 6 were three and four fold more potent in inhibition of AurkB and EGFR mRNA, respectively, compared with unconjugated siRNA.

E) Induction of Interferon-α Response by siRNA Transfection of Various Cancer Cell Lines:

Cholesterol-conjugated siRNA 3 (AurkB) and siRNA 6 (EGFR) transfected either in combination or singly into different cancer cell lines (PC-3, A431, A549 and HFF-2) as described elsewhere and incubated for 72 h in 24-well plates. At the end of 72 h, plates were centrifuged to remove dead cells, and 100 µL of supernatant was recovered. The supernatants were incubated overnight at 4° C. in round bottom ELISA plate. Wells were then briefly washed with PBST (phosphate buffered saline containing 0.1% Tween 20) to remove unbound antigen, incubated with 5% skim milk powder for 30 min at room temperature, washed 5 min each for three times in PBST, before incubating with anti-rabbit anti-interferon alpha antibodies for 1 h at room temperature. Wells were then washed as before three times with PBST and incubated with HRP-conjugated goat anti-rabbit antibodies for additional 1 h at room temperature. At the end of the incubation time, HRP substrate was added. Absorbance values were recorded at 450 nm with a reference filter of 560 nm. Based on the absorbance values with respective to the mock treated and untreated samples the interferon response was obtained. Their standard deviation values were measured from triplicates and results were showed in Table 8. siRNA transfection is often associated with IFN alpha production. However, there was no statistically significant release of IFN alpha either in treated or untreated cells, indicating that siRNA 3 and 6 did not elicit any IFN alpha response.

TABLE 8

Effect of siRNA transfection on induction of Interferon α response

| siRNA | PC3 | A431 | A549 | HFF-2 |
|---|---|---|---|---|
| *3 | 0.131 ± 0.008 | 0.294 ± 0.00 | 0.131 ± 0.00 | 0.243 ± 0.01 |
| *6 | 0.196 ± 0.033 | 0.285 ± 0.01 | 0.196 ± 0.03 | 0.332 ± 0.01 |
| *3&6 | 0.185 ± 0.021 | 0.300 ± 0.00 | 0.185 ± 0.02 | 0.270 ± 0.00 |
| Untreated | 0.197 ± 0.027 | 0.280 ± 0.00 | 0.197 ± 0.02 | 0.217 ± 0.00 |
| BSA | 0.089 ± 0.016 | 0.094 ± 0.00 | 0.089 ± 0.01 | 0.094 ± 0.00 |
| IFNα (25 ng) | 2.588 ± 0.011 | 2.58 ± 0.011 | 2.58 ± 0.011 | 2.58 ± 0.011 |

*Indicates statistically no significance was observed at $P \leq 0.05$.

G) Effect on Transcription

The specificity of siRNA for the target mRNA was tested in prostate cancer cells (PC3), transfected with siRNA as described earlier. 72 h after transfection, total RNA was prepared following the protocol of Qiagen total RNA isolation kit (RNeasy Mini kit), and a total of 2 µg RNA was suspended in 10 μL of water. The quality of RNA was checked on denaturing formaldehyde gels and the OD ratio was determined using Perkin Elmer Spectrophotometer. One μg of total RNA was converted into DIG-labeled cRNA following the protocol of Nano In-vitro Transcription amplification kit from Applied Biosystems. Fourteen micrograms of the resulting amplified RNA was hybridized to the Human Genome Survey array, which contains a series of 60 bp probes for interrogation of 29,098 genes. The arrays were hybridized at 55° C. for 17 h and subsequently washed and bound to antibody against DIG coupled with alkaline phosphatase. After the addition of chemiluminescent detection substrate, the arrays were scanned. Autogridding was performed by the imaging software and the result file was created that transforms the intensity of each gene into a numeric value, higher the signal-higher the numeric value and higher is the amount of gene present in the sample.

Controls were added for each and every step of the assay starting from reverse transcription (RT), in vitro transcription (IVT), hybridization and chemiluminescence detection. A quality report is generated for these controls that help to ascertain the success of the microarray experiment. Once satisfied with the QC report we proceeded with secondary analysis using Spotfire. The software normalized the data and performed a "t test" to determine the differentially expressed genes between two conditions. It also averaged the replicates and determined a fold change value for the two conditions. The probe IDs that were differentially expressed were sorted through a Panther database to determine which pathways or biological processes were affected amongst the differentially expressed genes, number of genes either down regulated or unregulated. The change in transcription expression levels ranging from a fold change of minimum 1 to above 4.5 was depicted in FIGS. 20-22 where the prostate cancer cells were inhibited for AurkB (siRNA 3) (FIG. 20), EGFR (siRNA 6) (FIG. 21) or both (siRNA 3 and 6) (FIG. 22). The figures indicate the number of mRNAs that have either been upregulated or down regulated with respect to the untreated controls. The transcription changes observed indicates that there was no general gene repression when both AurkB and EGFR were knocked down simultaneously rather individually. The down stream targets for AurkB, Histone H 3 and EGFR down stream targets, AKT were inhibited. Further the profile of the transcription in AurkB and EGFR knocked down cells indicate that there was an over all activation of Tissue Inhibitors of Metallic proteases (TIMPS), Caspases (for induction of apoptosis) and inhibition of matrix metallo proteases (MMPs) required for angiogenesis.

Example 6 siRNA was Effective Against Prostate Tumors In Vivo

1. Efficacy Studies in SCID Mice

To test the efficacy of siRNA in vivo, xenograft prostate cancer tumors were induced in 6-8 week old male SCID mice by subcutaneously injecting, into one flank, human prostate cancer cell-line PC3 at a density of $3\times10^6$ cells $mL^{-1}$ in 100 μL volume of PBS. Mouse developed tumors of approximately 40-50 $mm^3$ by the end of three weeks. Mouse were divided into two groups. Group R consisted of five animals treated with the combination of siRNA 3 and 6. Group C consisted of 3 animals that received only transfection agent in PBS. 8 days after siRNA treatment, the size of the tumors was evaluated and their standard deviations were observed as indicated in FIG. 23. Of the two groups tested, the siRNA 3 and 6 combination treated animals showed approximately 50% reduction in tumor growth in comparison with that of the placebo treated animals. The statistical significance was determined by paired two tail t-test where P≦0.05. Statistical significance in terms of causing tumor regression was observed between treated animals and placebo animals on Day 3, 4 and 5.

Tumor tissue was retrieved from the animals, total protein was extracted and subjected to western blot analysis. Total protein lysates from cancer tissues were resolved over 15% SDS-PAGE and probed with anti-AurkB antibody as well as anti-tubulin antibody as endogenous control. As shown in FIG. 24, treatment with the siRNA 3 and 6 combination resulted in complete inhibition of AurkB expression, while mice treated with siRNA 3 alone showed partial inhibition of AurkB expression.

2. Efficacy Studies in Nude Mice—

To test the efficacy of siRNA on xenograft prostate cancer, tumors were induced in forty 6-8 weeks old male athymic Nude mice by injecting prostate cancer cell-line PC3 at a density of $3\times10^6$ cells $mL^{-1}$ in 100 μL volume of PBS subcutaneously in one of the flanks. Mice developed tumors of approximately 50-100 $mm^3$ by the end of three weeks. Mice which developed tumors were divided into following four groups—

1. Group A—Mice treated with 100 μg siRNA 3
2. Group B—Mice treated with 100 μg siRNA 6
3. Group C—Mice treated with combination of 100 μg siRNA 3 and 100 μg siRNA 6
4. Group D—Mice treated with Placebo 100 μg siRNA, conjugated with cholesterol at the sense strand and complexed with Hiperfect transfection agent, was injected intratumorally into each mouse. Weekly doses of 100 μg siRNA were continued for four weeks. The delivery of the cholesterol conjugated siRNA in complexation with mixture of cationic and anionic liposome formulation involved direct intra tumoral delivery as well as by subcutaneous delivery at the site of xenografted tumor in equal quantities. Placebo treated animals in Group D have received all the formulation lacking siRNA. Tumor measurements were taken for twice weekly using a digital Werner caliper scale. The volume of tumors was derived employing the following formula. Volume of tumor=$(W^2 \times L)2$ where W is width of the tumor; L is length of the tumor as determined by the digital caliper scale. Animals were sacrificed at the end of 35 days and observed for gross pathology. The gross pathological observations were:

1. Placebo-treated animals have showed very high vascularization of xenografted prostate tumors.
2. Placebo treated animals showed pale kidneys. Metastasis/outgrowth of the tumors to the lymphoid system was observed.
3. Placebo treated animals were weak and unhealthy from the behavioral observations in comparison over siRNA treated animals.

At the end of 35 days the tumor regression values for each group were obtained as shown in FIG. 25. In FIG. 25: Prostate cancer xenografted male athymic nude mice treated with siRNA 3 (Group A, n=6), siRNA 6 (Group B, n=6) siRNA 3 and 6 combination (Group C, n=5) and Placebo (Group D, n=7). Statistically significant tumor regression was seen in mice treated with siRNA 3 and/or 6 as well over the placebo. Of all the groups tested, the combination of siRNA 3&6 showed the best results, with 80% tumor regression over the placebo; siRNA 3-treated animals showed 67% regression;

and siRNA 6 showed 70% tumor regression over placebo treated animals. The results obtained were significant with respective to the placebo as well as with others groups of animals at the following day of measurement and continued so till the end of experiment:

Day 21: Data was significant for Group C (Tumor regression) vs Group D
  Data was significant for Group B (Tumor regression) vs Group D Day 28: Data was significant for Group C (Tumor regression) vs Group D
  Data was significant for Group B (Tumor regression) vs Group D
  Data was significant for Group A (Tumor regression) vs Group D Day 35: Data was significant for Group C (Tumor regression) vs Group D
  Data was significant for Group B (Tumor regression) vs Group D
  Data was significant for Group A (Tumor regression) vs Group D
  Data was significant for Group C (Tumor regression) vs Group A The summary of the data presented in FIG. 25 can be further understood by the pathology observed of nude mice containing the xenograft prostate cancer, as shown in FIGS. 26-31. In FIG. 26 it can be seen that treatment of mice with the combination of siRNA 3 and siRNA 6 affected complete regression of prostate tumors after 35 days of treatment initiation in animals C8 and C7, while the tumor was clearly present in placebo-treated animal D10. In FIG. 27, it is clear that prostate tumors, isolated after 35 days, from placebo (Group D, Animal 10) were much larger than those isolated from animals treated with siRNA 6 (Group B, Animal 26) or siRNA 3 & 6 combination (Group C, Animal 6). Similar results are also seen in FIG. 29.

siRNA treatment also decreased vascularization of the xenografted prostate tissue. This phenomenon was not due solely to inhibition of EGFR, as it was also observed in mice treated with siRNA3, targeting AurkB. For example, FIG. 28 shows that mice treated with placebo had an observably vascularized tumor (Group D), compared with those treated with siRNA 3 (Group A). In FIG. 30, arrowheads indicate the vascularization of the prostate tumor in placebo-treated mice after 35 days of treatment. By comparison, there is an absence of vascularization in mice treated with siRNA 3 (FIG. 31).

Results obtained shows that, for regression of the prostate tumors, there exists a critical volume and dosage of the tumors. Of all the siRNA tested combination of siRNA 3 and 6 caused an 81% tumor regression (FIGS. 25-27). On the other hand, Group A (siRNA3, AurkB) animals showed 67% of regression in comparison with that of the placebo treated animals (FIGS. 25, 28 and 29). Group B (siRNA6, EGFR) animals showed 70% regression over placebo treated animals (FIGS. 25 and 27). Observations of gross pathology suggest that targeting AurkB was associated with inhibition of angiogenesis, as observed in FIGS. 30 and 31.

The results also indicate that the initial volume of prostate tumor and dosage quantity required need to be determined for the effective application of siRNA 3, 6 and their combination as therapeutic drugs. The tumor regressions obtained, gross pathological observations and general behavior patterns of the siRNA treated and untreated animals indicate that indeed these siRNA have potential to be applied as therapeutic drugs under clinical conditions.

Example 7 siRNA was Effective Against Breast Cancer Cells

Protocols used for breast cancer cells are as described above for other cancers, unless otherwise indicated. Breast cancer cell lines SKBR3 and MCF-7 were transfected with siRNA 6 and, 72 h later, analyzed by Western Blot for EGFR protein expression. As a control, cells were transfected with mock, i.e. cells transfected with siRNA 7. Equal quantity of protein was loaded into all wells and, to ensure similar quantities of protein were transferred, blots were also examined for alpha tubulin as an endogenous control. As shown in FIG. 32 (SKBR3) and FIG. 33 (MCF-7), siRNA 6 transfection strongly repressed EGFR expression (170 kDa band)

Transfection of MCF-7 with siRNA 3 (targeting AurkB) repressed AurkB expression. As shown in FIG. 34, transfected cells expressed barely detectable AurkB protein, while AurkB was readily observed in mock treated cells. The principal aim of using siRNA 3, 6 or 3 & 6 is to inhibit the expression levels of the respective protein AurkB, EGFR or both together. If there is no visible band in siRNA transfected cells, it indicates efficiency of siRNA in knocking down expression of the proteins of interest. Again, equal quantities of protein were loaded onto the gel, and protein alpha tubulin (50 kDa) was also detected as a control.

The results obtained with Western blots was confirmed by examination of the mRNA levels using real time PCR, as described earlier. Table 9 below shows that mRNA were repressed in cells transfected with siRNA 3 and/or siRNA 6.

TABLE 9

Fold decrease in expression of AurkB and EGFR levels after 72 h after siRNA transfection of different cancer cell-lines

| Cell-line | siRNA 3 Fold change | siRNA 6 Fold change | siRNA 3 & 6 Combination Fold change | |
|---|---|---|---|---|
| | | | siRNA 3 | siRNA 6 |
| SKBR-3 | 8.17 | 32.81 | 4.60 | 4.70 |
| MCF-7 | 2.24 | 5.00 | 1.44 | 4.33 |

The metabolic activity of different cell lines treated with siRNA 3 (10 nM), siRNA 6 (10 nM) and combination of siRNA 3 and 6 at 10 nM concentration each was determined by MTS assay. As shown in FIG. 35, all cell lines treated with siRNA 3 and 6 show inhibition, compared with mock treated and untreated cell lines. Cell line HCC-38 showed significant proliferation inhibition at 10 nM concentration which suggests optimum concentration required for maximum gene repression may vary between cells. The statistical significance was determined between mock treated cells vs siRNA transfected cells by paired two tail t-test where $P \leq 0.05$. Significant proliferation inhibition was obtained in all cell lines (SKBR-3, MCF-7 and HCC-38) inhibited for AurkB, EGFR or both simultaneously. Repression of AurkB and EGFR expression simultaneously inhibited proliferation more than repression of either AurkB or EGFR expression alone.

BrdU incorporation was examined in SKBR-3, MCF-7 and HCC-38 cell lines, after transfection with siRNA (3, 6 and combination of 3 & 6) or mock, siRNA 7, as shown in FIG. 36. 48 h after transfection cells were incubated with BrdU over night and analyzed for BrdU incorporation by measuring absorbance values at 450 nm. All the experiments were done in triplicates and their mean absorbance values were presented as percent of cells in S-phase of cell cycle, which is an indicator of cell proliferation/growing potential of tumor. The statistical significance was determined between mock treated cells vs siRNA treated cells by paired two tail t-test where P≦0.05. Statistical significance was found between mock treated and all siRNA treated cells, as well as between AurkB, EGFR and their combination treated cells.

Repression of AurkB, EGFR or both simultaneously, also results in induction of necrosis or the compromise on membrane integrity resulting in release of LDH into the medium. FIG. 37 shows release of LDH from siRNA treated cells against mock treated cells. Of all the cell lines tested, simultaneous repression of both AurkB and EGFR resulted in more LDH release compared with AurkB or EGFR alone. Of the cell lines tested, MCF-7 showed maximum LDH release of 150-300% over mock, SKBR-3 showed between 50-150%, while HCC-38 showed 20-70% respectively over mock treated samples. All the experiments were done in triplicate and statistical significance (at P≦0.05) was found with respective to the mock treated and siRNA treated cells; between siRNA 3 treated, siRNA 6 treated, and siRNA3 and 6 treated cells. However, in HCC-38 cells, there was no significant difference between siRNA 3 and 6 treatments.

Colony forming efficiency was also examined in breast cancer cell lines treated with siRNA 3 (10 nM), siRNA 6 (10 nM), a combination of siRNA 3 and 6 at 10 nM concentrations each, and mock at 10 nM. Statistical significance was determined between mock treated cells versus siRNA transfected cells by paired two tail t-test where P≦0.05. As shown in FIG. 38, significant inhibition of colony forming ability was observed in all the cells treated with siRNA 3, siRNA 6, or both siRNA 3 and 6, as compared to with that of mock treated cells. However, there was no significant difference seen in MCF-7 cells treated with siRNA 3 and those treated with siRNA 6. In the SKBR-3 cell line, siRNA 3 alone was able to inhibit colony formation by 80%.

Example 8

Aurk B siRNA Caused Cancer Cells to Arrest in G2 Phase of Cell Cycle

Cancer cell lines (HeLa, A549 and PC3) transfected with siRNA 3 for AurkB and siRNA6 for EGFR, either independently or simultaneously, were harvested after 72 h. The cells were washed with PBS and fixed in 70% ice-cold ethanol at 4° C. for 60 min. Cells were then washed with PBS and treated with propidium iodide (5 g/mL of propidium iodide and 0.2 mg/mL$^{-1}$ RNase in 0.1% sodium citrate) for 30 min at 4° C. Propidium iodide stained cells were subjected to flow analysis using (FACScaliber, Becton Dickinson, San Jose, Calif.). Data were acquired for 10,000 gated events using Cell Quest software and analyzed using ModFitLT2.0 (Verity Software House, Topsham, Me.).

AurkB Knock Down Results in Arrest of Cancer Cells at G2 Phase of Cell Cycle:

Knock down of AurkB (using siRNA 3) resulted in arrest of cells at G2 phase of cell cycle, as shown in FIG. 39A. For example, in HeLa cervical cancer cells transfected with siRNA 3, 77% of cells were in G2 phase, while A549 and PC3 transfected cells showed 22% and 37% of cells in G2 phase, respectively, as shown in Table 10. Similar results were reported earlier when Aurora kinases were inhibited by small molecule inhibitors (Rojanala S, Han H, Munoz R, Browne W, Nagle R, Von Hoff D and Bearss D. The mitotic serine kinase, Aurora-2, is a potential target for drug development in human pancreatic cancer. Mol. Cancer. Therapeutics 2004; 451-457). No G2 arrest was noted, however, in EGFR knockdown cells (transfected with siRNA6). Further no additive effect on induction of G2 arrest in cells was noted in cells transfected with both siRNA 3 and siRNA 6, i.e., where both AurkB and EGFR were knocked down. None of the cell lines tested in the present study exhibited apoptosis.

TABLE 10

Knock down of AurkB (via transfection with siRNA3) results in arrest of cancer cells in G2 phase of mitotic cell division, as determined by propidium iodide staining followed by Flowcytometry analysis.

| Cell line & Apoptosis | Phase of cell cycle at 72 h | AurkB knocked down cells in % | Mock treated cells in % |
|---|---|---|---|
| HeLa | G0/G1 | 16.54 | 46.0 |
|  | S | 6.15 | 36.10 |
|  | G2/M | 77.31 | 17.86 |
| Apoptosis |  | 0.00 | 0.27 |
| A549 | G0/G1 | 44.08 | 52.10 |
|  | S | 33.69 | 38.63 |
|  | G2/M | 22.23 | 9.27 |
| Apoptosis |  | 0.21 | 3.92 |
| PC3 | G0/G1 | 40.11 | 42.21 |
|  | S | 22.18 | 37.24 |
|  | G2/M | 37.71 | 20.55 |
| Apoptosis |  | 0.10 | 0.00 |

HeLa cells were transfected with siRNA 3 (for AurkK) and mock siRNA 7. After 72 h, the cells were trypsinsed and labeled with propidium iodide for analysis of cell cycle using a flow cytometer. As shown in FIG. 39A, in siRNA 3 (for AurkB) transfected cells, 77% were in G2 phase, 6% were in S phase and only 16% were in G1 phase. By contrast, as shown in FIG. 39B, in mock siRNA 7 transfected cells, only 17% were in G2 phase, 36% were in S phase, while 46% were in G1 phase. This demonstrates that cells knocked down for AurkB go into G2 arrest, are less likely to go into S-phase, and exhibit no apoptosis induction.

These results indicate that cell death is induced by arrest of cells at G2 phase upon knockdown of AurkB (using siRNA 3) whereas there is no effect on cell cycle by EGFR knockdown (using siRNA 6). This might be the reason for the release of LDH into the medium by cells undergoing membrane integrity compromise in case of AurkB knockdown.

Example 9

Aurk B and EGFR siRNAs, Either Alone or Together, Induce Senescence in Cancer Cells HeLa and A431 cells were transfected in a 24-well plate with siRNA 3 and 6, either independently or simultaneously, as described above. After 72 h, transfected cells were subjected to a senescence assay following the protocol of Chemicon's senescence assay kit. Briefly, cells were washed twice with PBS and fixed in a fixative solution for 30 min. at room temperature. After fixation, cells were washed twice with PBS and incubated with X-gal solution overnight at 37° C. After incubation, cells were observed using a light microscope at 200× total magnification. Images were collected at 10 different fields for each well of a 24-well plate using a digital camera. Digitally captured images were analyzed by counting number of cells showing blue color and the total number of cells in a given image. The percentage of cells showing senescence was derived from total number of cells. All experiments were performed in triplicate; statistical significance was determined by t-test where P≦0.05.

Knock Down of AurkB, Alone or with EGFR Knock Down, Induces Senescence in Cancer Cells:

Knock down of AurkB (by transfected cells with siRNA 3) induced senescence in 27% of HeLa cervical cancer cells, as compared to mock treated cells (using siRNA 7). No significant induction of senescence was seen in cells transfected with siRNA 7 (mock) or siRNA 6 (for EGFR). On the other hand, when both AurkB and EGRR were knocked down simultaneously (via transfected cells with both siRNA 3 and 6), enhanced induction senescence was observed, as shown in Table 11 and FIG. 40. Data will indicate that similar results occur in A431 epidermal cancer cells.

TABLE 11

Knock down of AurkB, alone or with knock down of EGFR, results in induction of senescence in cervical cancer cells.

| Cell line | siRNA | % of cells showing senescence |
|---|---|---|
| HeLa | siRNA3* | 27.58 ± 3.7194 |
|  | siRNA6 | 6.935 ± 1.0677 |
|  | siRNA3x6* | 36.685 ± 3.1749 |

*Statistically significant over mock where $P \leq 0.05$.

Most cancer cells show stimulation of senescence pathways after 72 h of knockdown of either AurkB or EGFR or both simultaneously, as compared to mock treated cells. This indicates that apart from G2 arrest, activation of senescence pathway is an additional mechanism of cell death induced by AurkB siRNAs.

Example 10 siRNA Treatment is Effective Against Breast Cancer Tumors In Vivo

Having shown that siRNA 3 and/or siRNA 6 were effective against various cancers in vitro, and that in vitro results also reflected results in in vivo experiments with prostate tumors, the efficacy of siRNAs is tested against human breast cancer. Protocols for breast cancer cells are as described above for other cancers, unless otherwise indicated.

Breast cancer cell lines SKBR-3, MCF-7 and HCC-38 are all able to form tumors in nude mice. Following the protocol used with PC3 prostate cancer cells described in Example 6, breast cancer cells are injected into mice and allowed to form a tumor. siRNA are then injected weekly into the tumor. Mice are then examined for general health, tumor size, tumor vascularization and gross pathology.

Results will indicate that statistically significant breast tumor regression occurs in mice treated with siRNA 3 and/or 6, as compared to placebo. Results will indicate that siRNA 3 and/or 6 also decreases vascularization of xenographed breast tissue, and this phenomenon is not be due solely to inhibition of EGFR. Initial volume of breast tumor and required dosage quantity should be determined for the effective application of siRNA 3, 6 and their combination as therapeutic drugs. In addition to other cancers, these siRNA have potential to be applied as therapeutic drugs against breast cancer under clinical conditions.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention.

What is claimed is:

1. A composition comprising a short nucleic acid molecule that modulates AurkB expression, wherein the short nucleic acid molecule comprises a nucleotide sequence that is complementary to the entire sequence of SEQ ID NO: 3 and is up to 30 nucleotides in length.

2. The composition of claim 1, wherein the short nucleic acid molecule comprises a sense strand and an antisense strand, wherein the sense strand comprises SEQ ID NO: 11 and the antisense strand comprises SEQ ID NO: 12.

3. The composition of claim 1, further comprising a second short nucleic acid molecule that modulates the expression of EGFR.

4. The composition of claim 3, wherein the second short nucleic acid molecule comprises a nucleotide sequence that is complementary to SEQ ID NO: 6.

5. The composition of claim 3, wherein the second short nucleic acid molecule comprises a sense strand and an antisense strand, wherein the sense strand comprises SEQ ID NO: 17 and the antisense strand comprises SEQ ID NO: 18.

6. The composition of claim 1, further comprising a pharmaceutically acceptable earner.

7. The composition of claim 1, further comprising a lipid.

8. The composition of claim 1, wherein the short nucleic acid molecule is conjugated to cholesterol.

9. The composition of claim 3, further comprising a pharmaceutically acceptable carrier.

10. A composition comprising a short nucleic acid molecule that modulates AurkB expression, wherein the short nucleic acid molecule is 22-30 nucleotides in length, wherein at least 22 consecutive nucleotides in the molecule are 100% complementary to at least 22 consecutive nucleotides in SEQ ID NO: 3.

* * * * *